United States Patent [19]
Ohba et al.

[11] Patent Number: 6,028,250
[45] Date of Patent: Feb. 22, 2000

[54] PLANT PROMOTER AND METHOD FOR GENE EXPRESSION USING SAID PROMOTER

[75] Inventors: Toshiharu Ohba, Kusatsu; Shuichi Takahashi, Muko; Yoshiko Anma, Shizuoka; Kiyozo Asada, Shiga; Ikunoshin Kato, Uji, all of Japan

[73] Assignee: Takara Shuzo Co, Ltd., Kyoto, Japan

[21] Appl. No.: 08/913,842

[22] PCT Filed: Mar. 26, 1996

[86] PCT No.: PCT/JP96/00777

§ 371 Date: Sep. 30, 1997

§ 102(e) Date: Sep. 30, 1997

[87] PCT Pub. No.: WO96/30509

PCT Pub. Date: Oct. 3, 1996

[30] Foreign Application Priority Data

Mar. 30, 1995 [JP] Japan ..................................... 7-073043

[51] Int. Cl.⁷ .............................. C12N 15/29; C12N 5/04; A01H 4/00; A01H 5/00
[52] U.S. Cl. .......................... 800/287; 536/24.1; 800/278; 800/295; 800/313; 800/317.3; 800/317.4; 800/320.3
[58] Field of Search ........................... 536/24.1; 800/278, 800/287, 295, 313, 317.3, 317.4, 320.3

[56] References Cited

U.S. PATENT DOCUMENTS 4,407,956  10/1983  Howell .
5,516,694   5/1996  Nishitani et al. .

FOREIGN PATENT DOCUMENTS 0562836  9/1993  European Pat. Off. .
07779778  3/1995  Japan .

OTHER PUBLICATIONS

Kim et al. Plant Molecular Biology. vol. 24: 105–117, 1994.
Park et al. Plant J. 1996. vol. 9: 183–194.
Napoli et al. The Plant Cell. 1989. vol. 2: 278–289.
Giovannoni et al. The Plant Cell. 1989. vol. 1: 53–63.
Cornejo et al. Plant Molecular Biology. 1993. vol. 23: 567–581.
de Silva et al. Plant Journal. 1993. vol. 3: 701–711.
Wei Xu et al., "Arabidopsis TCH4, Regulated by Hormones and the Environment, Encodes a Xyloglucan Endotransglycosylase"; *The Plant Cell*, 7: 1555–1567, Oct. 1995.
Z. Schwarz–Sommer et al., "Genetic Control of Flower Development by Homeotic Genes in Antirrhinum Majus", Science, vol. 250, p. 931–936, Nov. 16, 1990.
J.P. Nap et al., "Development Biology of a Plant–Prokaryote Symbiosis: The Legume Root Nodule", Science, vol. 250, p. 948–954, Nov. 16, 1990.
D.M. Zurek et al., "Molecular Cloning and Characterization of a Brassinosteroid–Regulated Gene From Elongating Soybean (Glycine max L.) Epicotyls", Plant Physiology, vol. 104, p. 161–170, 1994.

J.I. Medford et al, "Molecular Cloning and Characterization of Genes Expressed in Shoot Apical Meristems", The Plant Cell, vol. 3, p. 359–370, Apr. 1991.
J. de Silva et al., "Molecular Characterization of a Xyloglucan–Specific Endo–(1→4)–β–$_D$–glucanase (Xyloglucan Endo–Transglycosylase) from Nasturtium Seeds", The Plant Journal, vol. 3, No. 5, p. 701–711, 1993.
K. Kato et al., "Liquid Suspension Culture of Tobacco Cells", Fermentation Technology Today, p. 689–695, 1972.
J. Gielen et al., "The Complete Nucleotide Sequence of the TL–DNA of the Agrobacterium Tumefaciens Plasmid pTi–Ach5", The EMBO Journal, vol. 3, No. 4, p. 835–846, 1984.
A. Depicker et al., "Nopaline Synthase: Transcript Mapping and DNA Sequence", Journal of Molecular and Applied Genetics, vol. 1, No. 6, p. 561–573, 1982.
A. Crossway et al., "Integration of Foreign DNA Following Microinjection of Tobacco Mesophyll Protoplasts", Molecular & General Genetics, vol. 202, p. 179–185, 1986.
F.A. Krens et al., "In Vitro Transformation of Plant Protoplasts with Ti–plasmid DNA", Nature, vol. 296, p. 72–74, Mar. 4, 1982.
T.M. Klein et al., "High–Velocity Microprojectiles for Delivering Nucleic Acids Into Living Cells", Nature, vol. 327, p. 70–73, May 7, 1987.
R.T. Fraley et al., "Liposome–Mediated Delivery of Tobacco Mosaic Virus RNA Into Tobacco Protoplasts: A Sensitive Assay for Monitoring Liposome–Proplast Interactions", Proceedings of the National Academy of Sciences of the U.S.A., vol. 79, p. 1859–1863, Mar. 1982.
M. Fromm et al., "Expression of Genes Transferred Into Monocot and Dicot Plant Cells by Electroporation", Proc. Natl. Acad. Sci. USA, vol. 82, p. 5824–5828, Sep., 1985.
A. de la Peña et al., "Transgenic Rye Plants Obtained by Injecting DNA Into Young Floral Tillers", Nature, vol. 325, p. 274–276, Jan. 15, 1987.
C.A. Rhodes et al., "Genetically Transformed Maize Plants From Protoplasts", Science, vol. 240, p. 204–207, Apr. 8, 1988.
K. Shimamoto et al., "Fertile Transgenic Rice Plants Regenerated From Transformed Protoplasts", Nature, vol. 338, p. 274–276, Mar. 16, 1989.
A. Hoekema et al., "A Binary Plant Vector Strategy Based on Seperation of vir–an T–region of the Agrobacterium Tumefaciens Ti–Plasmid", Nature, vol. 303, p. 179–180, May 12, 1983.

(List continued on next page.)

*Primary Examiner*—Lynette R. F. Smith
*Assistant Examiner*—Ousama M-Fait Zaghmout
*Attorney, Agent, or Firm*—Browdy and Neimark

[57] ABSTRACT

A plant promoter capable of inducing the expression specifically at the site and stage wherein the reconstitution of plant cell wall xyloglucan is necessary, namely, a plant promoter originating in a gene which encodes an endo-xyloglucan transferase or a gene which encodes a substance having a function equivalent thereto; and a method for modifying the function of a plant with the use of the plant promoter and a method for cloning the plant promoter.

27 Claims, 29 Drawing Sheets

OTHER PUBLICATIONS

K. Skriver et al., "Cis–Acting DNA Elements Responsive to Gibberellin and its Antagonist Abscisic Acid", Proc. Natl. Acad. Sci. USA, vol. 88, p. 7266–7270, Aug., 1991.

S. Ohta et al., "Construction and Expression in Tobacco of a β–Glucuronidase (GUS) Reporter Gene Containing an Intron Within the Coding Sequence", Plant Cell Physiol., vol. 31, No. 6, p. 805–813, 1990.

R.E. Sheehy et al., "Molecular Characterization of Tomato Fruit Polygalacturonase", Molecular & General Genetics, vol. 208, p. 30–36, 1987.

T. Minamikawa, "Regulation of the Maturation–Specific Expression of Seed Storage Protein Genes", Shokubutsu Saibo Kogaku, vol. 3, No. 7, p. 568–576, 1991.

K. Nakamura et al., "Tuber Formation and Regulation of the Expression of Genes Coding for Major Tuber Proteins in Sweet Potato and Potato", Shokubutsu Saibo Kagaku, vol. 3, No. 7, p. 577–587, 1991.

SEQUENCE LISTING (1) GENERAL INFORMATION:

(iii) NUMBER OF SEQUENCES: 75

(2) INFORMATION FOR SEQ ID NO:1:

(i) SEQUENCE CHARACTERISTICS:
        (A) LENGTH: 1875 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

| | | | | |
|---|---|---|---|---|
| AAGCTTTTTG | CACATATTTG | CAGCAGTAGA | CAATGCCACT | CGCTGAAAAA TATGATCTCC | 60 |
| CAGAATTTTG | GCACAAAAAA | TATATCCTAA | CTAATATTTG | ACTCTATCTA AGATACCACC | 120 |
| TGACATCAAA | TGTTTCAATT | TTATAGTCTT | TAGCACGAGA | AGATGTATAT TAGATATAAA | 180 |
| CCTTATCTTA | TTTAATTAAT | TTAGTAAGAT | TGAATTAGAG | GTAAATTTTA TTACTTAATA | 240 |
| TAATTAGACT | ACTCATAAAT | ATATAAATTT | AAATTTTAAG | TGTTCATTCC AATATATGAA | 300 |
| ATCTATTGAA | AATATCACGT | CAACTAATAA | TATAACAAAA | CTATAATATA AAAATAAGTA | 360 |
| TAAATTTTAT | ATTTATAAAC | AATTTTGACA | TTAAATTAAA | CTTAAATTTA TCTCTATTAA | 420 |
| TAATAATATT | ATAAGACAAA | TTACTCTGCT | AAAATACAGA | AAACAATATA TTTTTTTGAA | 480 |
| ACTTTGAAAT | ATTATATTGT | TGGATGATGT | TGGATAATTA | GAAAGGACAT ATTATATATA | 540 |
| TGTCACGTTG | AGATGAGTGG | CCCATTGCAC | TGAAAATGAC | TGACAAATGG TACTCTCAAT | 600 |
| CCCATCTTAT | TCTCTGTTCA | ATTTTTTTCA | CTTGAAAACT | CTTTTTCCCT ATGGAAAATA | 660 |
| GCAATAACTA | CAATATCCTC | GTTTCTTCTT | GTTAGCTCTT | GGCTACAACT GTGTTCATCT | 720 |
| TCTCCACTTT | CATCAATACA | ATTCCAAACA | GAATATACTT | AGACCCTTCT GCTATTTCAA | 780 |
| GAAAGTAGCT | TGCAAATTTG | CTTTGTTTCC | GACATACACT | TCAATATGAA AAAAAAAAA | 840 |
| AAAACACTTT | GAGAACTTTT | TAAAAAGTAT | TAAGTAGGAT | TTGACGGCAG AATTTTGTTT | 900 |
| CCATATTTAG | TTGAAAATAC | ATACAAAACG | TATTTGAAAG | TTATATTCGA TTGAATTTGG | 960 |
| TTTTAACATA | GAAAAAATTC | AACCAAATTA | AGTCCATACT | TAAGCATTAA TATAAATATT | 1020 |
| TCAGTTATTC | GACTTCGGTT | TCACGTCTTG | CCATTGTTTT | ACATGTGTAA TACTTCAATT | 1080 |
| AATTTTTTAT | GTTTTCATGT | CTCTTTATCC | ACTCCCTTTA | TTTTTACATT ATAATACCAC | 1140 |
| ATTCCTCCAA | TACTATAATT | CTTAAGATAT | ATGTGAACAT | TAATATCTAA TGATACATAA | 1200 |
| GGTAAGTTGT | AAATATTCAT | AGAAAAAATA | AAATGACTTT | TCAAGAAAAC CAACAACTAA | 1260 |
| ATATAAAATA | TAGAAAAGTT | ATTTACAATT | TTGTCCGTTA | ACATGTCCAG ATATTACACT | 1320 |
| CTCAAAAGAA | AAAGTGTTAG | AAAAATCATA | TAAAATAGAG | TTCAAATTCT TTGTTAGATT | 1380 |
| TTTTTTACTG | AACATTTAAA | ATATATATTG | ATATTGATTA | TTCATTTTTA TAAATATATT | 1440 |
| TTAAAATTAA | CATTCAATAT | ATATATTTTA | AAATTAACAT | TCAATATATA TATTTTAAAG | 1500 |
| ACACAGAAGA | AACAACAAAT | TCCATAAAAT | TGTGAGATAA | TATTTAACCC TAACTTTCTT | 1560 |
| ATGAACTGAG | AGATTTTACA | TTTATGAGAA | ATGATTGTCC | TGTGTTAATT ATCCATGTCA | 1620 |
| GCTACCTAAT | CACTAGAAAA | GCTAATCAGA | ATTCTGTGAT | CTAGTCCTAC TATTCAAACA | 1680 |
| CTTTTAGGCC | AAAGAAAATT | GAAACACAAA | ATACCAGTTC | TCAAATACAA TGAACATTAT | 1740 |
| TAATTATAAT | TCAGTTAAAA | GTCATTGATC | AGAACAGCAG | TGAAGGTTAG CTATAAGCGC | 1800 |
| GTTATAGGTG | CAGGCAGAGT | GTCGTGCCTA | TATATACCCT | TGGAATGCA CAAGTTGAAA | 1860 |
| CACAAAGAA | AAATG | | | | 1875 |

(2) INFORMATION FOR SEQ ID NO:2:

(i) SEQUENCE CHARACTERISTICS:

(A) LENGTH: 1965 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

```
AAGCTTCAAG TAAGTCTCTG TGATATGTAT GCAAGGGTTC GAAATGAGAA GAAGGCCCTT      60

CAAATTCTAG GTGTACTGGA ATCTAGGAAG GATGAATTAG GAAAAGCTGA TTTTGAGAGA     120

ATTATAAGTG GCCTTATTGA TGGTGGGTTT CGGCAAGATG CCCAACGAAT ATGTGGGATC     180

ATGGAGGCGC AGGATTTCGA TGCATCAAAG GTTAAGGTCA ACCTTATGAA GCCTGTCTCT     240

AGAGGACCTC GTATGAGATA GTTTAGTGGT CATGAATTGG GACATTTTAG TCTTTCTCTG     300

CAAGTGAGTT ACAAATGTAT TACCTTATAT AGGAAGCAAT GTCTGCATGA TTTATCATAC     360

CATGTAACAA ATAAGAATGA ATTTGTTTAT GGATTTTTCC ATTGCTCAGA TTCTGAATTT     420

ACGCAATTTT TTTTTTCTTT TGAACTTTAG TTGTTTGTAT ATACAAATGT CTTCTGTGGC     480

ATGTTCATGG AATTTTCATT TCCAATTATT CAATATTCTT GTGGTGTGAT CATCACTTTT     540

GTTAGGCAAA TCTGACAGCA CTGATGCCCC CTATCAGGAT TTTTAAACTT GTATGCGGTA     600

TACTATACTG ATCACAAGAT ACAAACTAAT ATAAATGGAT AGGAAATGCA GATGGGATGG     660

TTCAAGCTAG TCTTTAATAT TGAGATAGTA CAGAAAATGC AATGCCCAAA GTAAACAACG     720

CTGATATTTC AAAATCACAT ATTAAAGCTA AAGTTGGTAG CAACTAGCGT GAGAGCATCC     780

TAGTCTAGAC TGTGAATGCA GTATTTATAC ACTACAATGA TCTAAATAAG ATGCTACTAA     840

TGCAATCATG CTTAATGTAA TATGAATTGA CTCTAAAGTAG CTTGCAAATT TGCTTTGTTT     900

CCGACATACA CTTCAATATG AAAAAAAAAA AAAACACTTT GAGAACTTTT TAAAAAGTAT     960

TAAGTAGGAT TTGACGGCAG AATTTTGTTT CCATATTTAG TTGAAAATAC ATACAAAACG    1020

TATTTGAAAG TTATATCCGA TTGAATTTGG TTTTAACATA GAAAAAATTC AACCAAATTA    1080

AGTCCATACT TAAGCATTAA TATAAATATT TCAGTTATTC GACTTCGGTT TCACGTCTTG    1140

CCATTGTTTT ACATGTGTAA TACTTCAATT AATTTTTTAT GTTTTCATGT CTCTTTATCC    1200

ACTCCCTTTA TTTTTACATT ATAATACCAC ATTCCTCCAA TACTATAATT CTTAAGATAT    1260

ATGTGAACAT TAATATCTAA TGATACATAA GGTAAGTTGT AAATATTCAT AGAAAAAATA    1320

AAATGACTTT TCAAGAAAAC CAACAACTAA ATATAAAATA TAGAAAAGTT ATTTACAATT    1380

TTGTCCGTTA ACATGTCCAG ATATTACACT CTCAAAAGAA AAAGTGTTAG AAAAATCATA    1440

TAAAATAGAG TTCAAATTCT TTGTTAGATT TTTTTTACTG AACATTTAAA ATATATATTG    1500

ATATTGATTA TTCATTTTTA TAAATATATT TTAAAATTAA CATTCAATAT ATATATTTTA    1560

AAATTAACAT TCAATATATA TATTTTAAAG ACACAGAAGA AACAACAAAT TCCATAAAAT    1620

TGTGAGATAA TATTTAACCC TAACTTTCTT ATGAACTGAG AGATTTTACA TTTATGAGAA    1680

ATGATTGTCC TGTGTTAATT ATCCATGTCA GCTACCTAAT CACTAGAAAA GCTAATCAGA    1740

ATTCTGTGAT CTAGTCCTAC TATTCAAACA CTTTTAGGCC AAAGAAAATT GAAACACAAA    1800

ATACCAGTTC TCAAATACAA TGAACATTAT TAATTATAAT TCAGTTAAAA GTCATTGATC    1860

AGAACAGCAG TGAAGGTTAG CTATAAGCGC GTTATAGGTG CAGGCAGAGT GTCGTGCCTA    1920

TATATACCCT TTGGAATGCA CAAGTTGAAA CACAAAAGAA AAATG                    1965
```

(2) INFORMATION FOR SEQ ID NO:3:

(i) SEQUENCE CHARACTERISTICS:

(A) LENGTH: 2960 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
AAGCTTGATA GATACAATTT GTATGTACCA ACTTGAGAGG AGTGTTAAAT ATATTATTTT      60

TATTTTATAT TTATCTTTTA TTTTTAGTTA GTTTGTTATT ATTTATTATT TGTATTTTGG     120

GCTTAGTACA TATTTCTTCT ATTATAAATA AAAGACTCTA CGTGTATATT CAACATAAAG     180

GAGATTAATC TTATACATAA TTTTCACTAT ATTCAACAAC TATCATAAAA AACATGTAAA     240

AAGAGGCAAT TACCATTGCA TCTTTAACAA CAATTGTGAC TTTAAACTAT CGTTATTACT     300

AGTAACAAAA TCCTATTTTT ATACATGTAA ATATTTAGGA TGAAAATTAT CTCTTTCCAT     360

TGAATAATAA TAAACTTTGG ATAAATAAAA TTTGATCCTG TATTATTAAT TTTATTTTTG     420

AAAAGAATGA AAATTTTAAT TTAATTTTTC ATTACATACA AATTTTCAAA TTCATTAGTA     480

ATTATAAAAT AGTTTCATGT TTTTGTTAAA TTAGTTGTCA AAACATATTT TTAATAAAAT     540

ATCTCGAAAA AAATGTTAAC AATAAAAAAT AGGACCTTTT GACACTCCAT AAAAAAACAT     600

GTTTTTTTAA TCAGAAAAAC ATGTTATAAT AATCGATAAT ACTATTCTTC ATATATCAAT     660

GTATACATGT TAGAAATACT ATATATGTTA CTCAAACTAA TATAATATAT ACTTATATTT     720

CAAAAATAAA AGAAGATAAA ATTATCCTAC ATATTGTTTC TTTAAATTTA CATATAAAGT     780

CATATTATCG TTTTGAGTAC TCACTTAAAT AATCAAACAT GGTATATCAT ACAACATATA     840

CATATATTAG TTTACAGATA AAATTATAAC AAAATCTATC TAATTCACTT TTTAAGAACA     900

CAAATATTTA ATTACATTTC AATATTCAAA GTAATTTGTT ATTGATATAT TTAGAGGATT     960

CATATTAAAC ACATGTAACA AGGAAAATAT ATAGAAAATA TCGTCTTATT TCAAAGTTAG    1020

ATAATTCATT TAACATAAGT CTTTTCTATT CTTGTCACCT AATATCTTAA TGCTTATAAT    1080

CTATAACCCC CCCAACAATA TATCATATTT ACATAATGAT TTATACTATC AATAATATCA    1140

TGACTCTTGA GACATAATAT CATCTCTCAC CATACACTCC CAAAATAACA ATATCATATA    1200

TAACATCATA AAAGTATCCA CATGAAATAT ACATCATCAT AATACCACAC ATTTTCATCA    1260

TAAACATACA CATATTACAT ACATGAATAC TAATCTTTCA ACACAATACC GTCACATGGG    1320

AGAACTTAAT TTGCCTCTCG TCCCAAAGGA GAAAACCTAA AATAACAAAC AAATTTTTTT    1380

TTTTGTGTTA GTAAACATAC ACACTTTTTT AACACTCATA CAATTCACAT ATCTAAAATA    1440

ATATTTAATG AAATAAATGT AAGTAATTA AGTGCCAGTT ATCTAAAAGT GATATGCCTA    1500

CTAGTCAATG GATTAGAAC ACCAAATATC CCAATTAAGT TATTAAAACA CCTTAGTTTA    1560

AACCTTTATA TCATTAGCAC CATTATAATA AGAAAATTTG AATAACAGGA AATTAAACAA    1620

TTACATTTGA TCAATAATAT ATTTAAACTG CCTTGATATT TTTACCTGCT ATCTCTTTGC    1680

ATAAAATATA TATTTGATTG TAATTTTAGA TTTTATATAT TATAAAAAAA TTAGTTTTAG    1740

TTCTTAATTT TTTTTATTTA AATTTGACTT CTTTAATTTT TAATCATTCG TAACTTTAAT    1800

CTTTGAATTT CTTGAATAAT TACTAAAGTT TTAATTATAT GCAACTTTAT TCAATTTTCA    1860

ATTTTGAAAT TATACTGAAG CACTATTTTA TTACATTTAC ATTAAAGTCC TGCATTCTAT    1920

TCTTCTCAAT TTTCTAAAAG ACCACGCACA TTATATACTT TACCCAATCT TATTATATTA    1980

TGTTTAATGT AACCCAAATT ATAGATAATT GATCTTAAAA TTGAACAACA TTATGATCGT    2040

TAAAAACTAA AATATACAAA TTGGGTAAAA GAAAATCCAC AGACCCAAAT AATGAATATT    2100
```

-continued

```
ATAAAATGAG GGACTAAAAA CTACATAAAA TAATATGGAC CCAAAAAAAT ACATATTTTA    2160

TAAAATATAA ATTCCAGAAT TACAATTAAG TAAAAAGATA TTAAAAGATA AGATAATAAA    2220

TTATTTATCA AATATTTTTA ATTTAATTAT AAAATTTGTT ATTTAAATTT TATTTTTCTA    2280

AAATTTAAAA AAAAAACTTA TAATTAATAA GTTTAGCATA CAGGTGAGCA TGTCAGTATT    2340

ATATAAATTA AATATGTCAA TAGTCCATTT AGTATTAGGT GTATTGTCAT ATATCAACAT    2400

GAAAGCAACA TGATTTAAAG AATAATAAAC TAATACATGA TTAAAACCGT TTAAATTTAG    2460

AAATTAAGAA ACCAAGCGTA CAGAATTTAA AAGTAAATAA AAATCACATT GGAAATTTTA    2520

AGAGGATAAA AAATACAATT AAATCTAAAT GGTTTCTAGT TAATATGTTT TCATACACAT    2580

AAATATCAAG AAGCAATTCA TTTTACTTGT TTATAGAATT CGGTTCTTAT CCAAATTAAA    2640

AAGAAAATTT CTTAGGCATA CTAAATTATA TATTTGATTG AATTTAACAT TCATTTAAAA    2700

ATCATGTCTA TTAGGTACAA AATGATTGCT AATTAGCGAG CCCCAAGGTG TAATAAACGC    2760

GTAATATCAT GATGACACCT GTTACTTCTA GCTTTCGAAG ATCATAATCA TGAACAGAAA    2820

TATACCTAAT GAACAGAAAG AAAACTCCTG TGGCAGAGAT GAACGAAGAA GCAAACTTCC    2880

AAAGCACGGT GATGTGTCTA TATATATATT CCCATTAGCC TCAAAGACTT TCACAACACT    2940

TTCATCTTTC CCTTGTTAAC                                                2960
```

(2) INFORMATION FOR SEQ ID NO:4:

(i) SEQUENCE CHARACTERISTICS:
        (A) LENGTH: 3300 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
CCACCGCGGT GGCGGCCGCT CTAGACATAA TGATCTCTTT CAATGATCAC CATTAAATAT      60

AGACACAAAA TAGATTTGAA CTTAAGATTT ATCAAATTAA GTTAACAAC TAAAATCCAA     120

CCAGAGAACC ATGATCTCTA TCCACAAGTT ATTTTAGAAT GATTTGAGAA TGAAATTCTA    180

CTAATTAAGT CATAAAAGTA TAACAAAAAA CATGAACATA TAGAAATGAT AATGAAATGC    240

ATTTTTTTAA CTATTCTTGC AGGATAGAAA ACATACTGCA AAGATTCCAG AGAAAGTTTT    300

TCTCTTTACT CTTCAACCTT TTAGCTCATA TTCTTCCATG TCTAGGTATC GTTCCAAGCG    360

AGAAGAAGTG TGTTTGTAAA AGACACTATG ACGCTCAAGT AAGGAGTGTG CCTTTGATGA    420

TAATAAATAT TTTAATAATG AACACATAAT TAATTACCTC GTGAACAAGA CTATTTATAT    480

TAGGTTTATG GGTCCTTACC TGTTGGGCTT GGATTACATA GATAATCATC ATGGTTAATT    540

TGTTAGTGA TCTTGCTAAT ACTTTTAACT CTTAACCTTT ACTGATCCTT ACTATTACAA     600

TGTGATCTTA AACATTACAA AATGAAATAA TGTTAGGTAG GTGTTCATGA ATATTTAAAA    660

TGATTCTTGA TCGGTATGAG CCAAAATCAT CTCTGGTACA TATAAATAGA GATGAGTTTA    720

GTCATTACAT ACCCACATAA TGTTAAGTAG ATGTTTACAT ATGATTGATA AGATAACCTC    780

TCGTATATAG GTTGAAATGG TCTTTGATAC ATGTAATAAC ATTAGATGTT AATAGTTAAA    840

AATTGATTAA AATAAAATTA CATATAATAA TTTATTTTGA TACATATTGC CAGACCTCAT    900

TTAAAACGCA CCCAAAAACC TTCTGAACGG ACGTCAGGTG TCAAGCGAAG AGGATCCGGA    960

AATCAGATAG TGGAAGGCAG GTGTCGGCAG ATGAGCGGAC GCTCGTTTTG ACGTGGGAAG   1020

CAAAACTTGA TTTTTCAGAA AATTCACGTC ACACTCTCTG CATGCACCTT CTTCCCCAAA   1080
```

-continued

```
CTCTGAAAAT TTTATTTCTC CTCCTTCTCA CTAAAAACTC TCCCTTCTCT CTATAAAATA    1140

TCATCATTTG TTGATAATTT TGATGTTCGT TTTGAAGTTT TTTTATTATT ATTTAATTAT    1200

AGTAATATCT CCTTCTTAAA TTCCTTAAAT AATATCTATT TATTCATGTT TTCGTTATTG    1260

TCGATATATT CTAACTACAA AACTATCTTA AATACTTAAT AATGTAAAGT TAAGGTAAGA    1320

TAGCGAAAGC AAAGGTAAAT GTAAATCAAA AATAAAACA AACTTTGTAT TTAGACATTA     1380

ATAATATATA TAAAAAATAC CCTTATATAT AATGGATTCT ACGTTTTAAG GTTAAGGGTA    1440

TTTTAATAAT TTTCATTCTC AAAACTAAAA AAAAAAAAA AAAAAACCTC ATTTTCAAAA     1500

CTAAAAAAAA AAAAAAACCT CCAAACCCTT AGTTACCTCT CTCATTCCTC TCAACCCTTT    1560

CTCTCTCATC TCTCCCACTC CAACCTTTTC TCTGTCATCC CTACTGTAGT CCCAATTGAA    1620

AAAATCAGAA ACTCTAGCCC CAATTGAAAA AATCAGAAAC ACTTGCCGTT AAATTGCCTT    1680

TGTAAAGAGT TGAGTCATTG ACATATTCAC CTTCAGGAAA AGGTTCACTC AAGATCTCTT    1740

CAATTTCACC ATCTTCATTA ACCTCTCTAA TTTCATCATC TACATGTGTT GAATCATCAT    1800

CTCTAAAAAA TTATAAAATG AAAAGTCATT ATAAAATCAT TTTTTGTAAG AAATTGTTTA    1860

ACGAGTGTCT CTGATTTTTT CCACGCCAAT TACCAATTCC TTTGATGTTA TTATGCTTGT    1920

GAAAATTAGA TAAAATTAGA TAAAATTAGA TAAGACAAAA ATTATAAAAT GAAAACTCAT    1980

TATAAAATCA TTTTTTGTAA GAAATTGTTT AACAGCGAGT ATTTCTGATT TTTTCCAGGT    2040

CAATTACCAA TTCCTTTATA CTTGTGAAAA TTGGATAAAA TTAGATAAGA CAAAAATTAT    2100

AAAATGAAAA CTCATTATGA AATCATTTTT GTAAGATTGT TTAACGACAC ATGTTTCTGA    2160

TTTTTTGAAT TAGGGCTATA GTAGGGATGA TAGAGAAAAA GTTGGAGTGA GAGAGATGAA    2220

AGAGTGAGGA TTGAGAGAAA TGAGAGAGGT GAATAAGAGT TTGGGTGTTT TTTTTTAGTT    2280

TTGAGAATGG AAATTATTAA AATACCCTTA ACCTTAAATT TAGAATCTAT GATATATAAG    2340

GGTATTTTTG TCTACTAAAA TCTGATACAT ATTACTCAAA TGTACCAACT AAAAAGAGAC    2400

GTACACGCGT TACCCAACCC CATATATATA TATATATTAG CCTCCCAAAC TATCTTAAAT    2460

AAGGTAAAGT TAAGGTAAGA CAGCGAAAGC CATAAGTAAA TGTAAATCTA AAAGTAAAAC    2520

CAATTTAGTT TTTAGACATT ACGAGTATTC AGGCATTCAT AATTATGGTA CAACTTTTTA    2580

ATAAAGAAAT AAAAAGAACA ATTCATTATA TACACAAAAA AAGTTACATA CACTGAACTT    2640

ATCACTTATT TCGTACACAC AAAAATTATT TATATTTTTA CATAAATCCT ATCTAGTCAG    2700

TTTTCTCCAT TAAAATATTA TATAAAAATA TATAAATATA ATAATAAAAT TTAAAATACA    2760

CCTCTTTGAT TTGCAACGAG CCACCAGAAG GAGAGATTGT TAATTTAAAC GGAGTAAATA    2820

ATCATCAAGT GCCACGAAAT AGTTACATAA TCACGAAGTT ATCTACAAAA AATAGCCTAA    2880

AATGCATTCG AAAATTTATC ATTATTGCAA ACAACAATAC TCTAATCTGA AAGAGATTGA    2940

TGATTACAAA GATTAGCTAG CAGTCAATTT AAATAAACGC GTAATAGTCT CTCTATTAGT    3000

TGTTTCCAAC ACAAAATCCT AACTAAAGCA AATGCATGAT TCTTTGTCTT CATCTCTCTC    3060

TCATCTGACA TAAAACAAAT CTTAAATATA TATCATTAAT CATTATAACA AGCATAAACT    3120

TGATCGTTTT TGTTAAATGA TGAAGCATGT ATTATTGAAT TAAATATAAA TTTATGTTGA    3180

ATATTTAAAA AGATAGAAAG TAGAGGGAAA GAGAGAGGAA GAAGGGTATT GGGCTAGGTG    3240

CAGTGCTTAT ATATACCCTT TTCTTAGCCA TTAGCTTCCA CAAACAGATA AACACAGAAA    3300
```

(2) INFORMATION FOR SEQ ID NO:5:

(i) SEQUENCE CHARACTERISTICS:
        (A) LENGTH: 1127 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:5:

```
TCTAGATGGT TTCACCCAAC TACATGTTTT GTTCTGTTTT GCTTTGGTTT CAAACTTGTG        60

ATAAAAGCAA CGCGTTGAGT CTGTTTGTCA ATTTTGTTCG ATTTCAGATT CTCTGTGGAT       120

GGAACTCCAA TAAGGGAGTT CAAGAACATG GAGTCAAAGG GTGTTCCATT CCCCAAAAAC       180

CAAGGCAATG AGGATATACT CAAGCCTTTG GAATGCAGAT GATTGGGCCA CAAGGGGAGG       240

GCTTGTTAAA ACCGATTGGA GCCAAGCTCC ATTCACGGCT TCATACAGAA ACTTCAATGC       300

CAATGCTTGC ACTGTGTCCT CTGGAACTTC TTCTTGTTCA AACTCTGTCT CTTCTCCCAA       360

TGCTTGGCTC TCGGAAGAAT TGGACTCTAC TAACCAGGAG AGACTGAAGT GGGTACAGAA       420

GAATTACAAT GATCTACAAC TATTGCACCG ACGCCAAAAG ATTTCCACAG GGCCTTCCTA       480

CAGAGTGCAA CACTGCCTAA TTTTTCTTAT CAATCCTTTC CATGCTCCAC TTTCTTTTTT       540

ATTTCTTCTG TTGTACTTTC CATCATGATC AATTCTTTTA TTCATTGTAA AACATTGCTA       600

TCATGATAAG TTTTCTTAAA TATTTGCATA AGAAACTTGC CGTATAAATC GTCTATAAGC       660

AGGAAACTAA AATAGTCCAG GAAATCGAGA ATCGAGAAAC GAGAATTTCC AGGTCACCAA       720

CCTGTGAAAA TTGTTTTTGA TCTTCGATAA AAGTATTAGT TAATTAAAAA AACACAAGAT       780

TGTTGAAAAT ATTAAATAAT AGAAACCATG TACTGTGTAT GGCGGTGTCT CCTTATATAA       840

ATTTCATGCA GAAACGCGTG AAATGATTGG TGTGGGCGTC CATTTACAAC AACAAAACTT       900

ACTACTTTTT CATTCTTCAC CAGCTGTCTA CAACTAATTC AAAAGTTCAC AACCTACCTT       960

TTTCTCACTT TCCTCTTATC TACCAATCTC TCTTTTTTTC TCCTATAAAT ACCATCCTTT      1020

GCAGTATCAA CCAACATTCT CACAAATAAC CAAAAACAAT TTCACTCAGT TTCACACAAA      1080

ACAATTCTGC ATGGCATTTT CAAGACTTTT ACTGTTAACA TGCATTG                   1127
```

(2) INFORMATION FOR SEQ ID NO:6:

(i) SEQUENCE CHARACTERISTICS:
        (A) LENGTH: 1406 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
AAGCTTGTTA AACTGATTTA AAAGTTCGTT TTTTAATATA TCAGAGTGTT TGATAATTAT        60

GAAAGTAACT TATTTTAAAT TAAATATGAT TTATTTTTAG CCAAAAGCTA AAAGTAAGGT       120

AAAGAGTGTT TTTTTTTCTA ACTTGAAAGT TATTTTATGT TGACCAAATA TACAAGTATC       180

TTTTTGCCTT AATTCTTTTA TTTTTTGTTT TTTATTTTTT ATTATTATAA GTTGCGCATA       240

TAAAATTAAC TTAAGTAATT AATTTATATA TTTGTCTTAT GAATAATTTG TGATGATAAA       300

GAAATATATG AATGATCAAA AATACTATTA CTTATTGATT AAAATATAAA TTAATTTGTT       360

CTAACTCTTT TAAGTATAAA AAACTTAAAA TTAAACAAAT TTTTTTCATG TTAACCAATT       420

TAAAGGTATT TCAAATATTT TTATTTTAAA AGAAGGTGT TTCCCCGCAT TTATTTGCAA        480

AACACATCAA GAATCTTTTT TCAACTTCGA CACTTTTATT CAAACATATG AATAATTATT       540

TCAAATATAA TTTTTAGCAC TTTAAAAATC TTTTTTTAAT TCAATCTAAA TAGGCTCTTA       600
```

```
ATAATTTTTT AAATTAATTA GACTTATTTT TAAATTTAAT AATTATTTAT AAAAAAATCG    660

TATAAAATCG AAAAAAACAA AAGCACGCGC TATTAGGTCG AGTGAGATGG ATGGGGTCAT    720

AAAATTTTGC TCCTCGGTCT GAGGGTGACA AGCCTTTTCT CTGATACGGG CATGTGCATG    780

TCCCCGTTAA TTACTCCCCC AATGTGCAAT TACCCACTAA CTCTAACCCC TCTTTTGGAC    840

AATTATTTGA AAGGCTTTAA TTTAATTATT TTTTTGTTTT TCATTCCATC TATACTTATA    900

TTAAAGTTGA ATCAAATTTA GAATTACACT TGTATTTAGC ACTAAAGTGC TATATAATAA    960

AAAATGACTA TGTACTCAAG AAAAATTAAA TTTGAAATCA ACAGAAGAGT CATAATTTTT   1020

AATAAAGAAA TTTAAAATTT ATAAAAATAA ACACAAAAAA TGTCTCAAAG GAGATTAGAT   1080

ATCTATTAGA ATATTATTGT AATAAAATAT AAATAATATA ATTTTGCATA TTCGAAGTTT   1140

CTGATTAAGG ACGAAAGAAT AATCGTGGCT GCACAATAAC CTTTGTTGGT GAAAGGACAA   1200

ATTTCAACCA CCCAAAATCT GAAAAATCTA ACTTTGTTTC AACTTTCAAC CACAAGTCCA   1260

ACTCAGTCCC TTTTACACCT ATAAATAACC AGTCACTACA CTTCCATTTT CCTCACCCCC   1320

ATTGGGCCAT ATTCATCATT CTCTAAAAAA AGAAAAAAAG AAAAATACAC AAACACTGGT   1380

CTCTGATTGG ATTTGTTTTT CTCACC                                        1406

(2) INFORMATION FOR SEQ ID NO:7:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TCTAGAGTTA GATCCCGAAT AATTATCTTA CACCTATCCT ATCAAAACTC TATTTTCTCT     60

CATTGATAAC CTTCTTTGCT TATTCCTTGT TTCGATAATC ACTAGTCAAT AGATTTAGAT    120

TCGTAGTTAA TTTTAGTATT AATCATATAA ATCTCAACTG TTGATCCTCT TGGATAGCAA    180

TCAAGGTAGA AACTACGAGA ATACTGTTTA AATCCAATCC TTGTGGATAC GATATTATAC    240

TATATTATCT TTGATTATTG AGCATAATTA AGTGTGTGTT TTGCGTTCGT TACAAAAGTC    300

AAGTTTTCTT GAAAATAAAA ATTTCAAATT ATGTTATACT ATTTTATAAT AGTACTTTAC    360

TATAGCAGTC AAAAAATATT TGGAACAAAA TGAAATTGTT ATAGAGGGGT TTAGACATTT    420

TAAGCGATAA TTAAAAGTGA AAAGCACGCG CTATTAGGTC GAGTGAAATG AATGGGGTCA    480

TATAACTTTC CTCCTCGGTC TGAGAGTGAC AAAGCTTTTC TCTGACGCGG GCATGTGCAT    540

GTCTCCGTTA ATTGCTCCCT CAACGTGTAT TACCCAATAG ACACCTCCCA ATTATTTAAA    600

AGGCCAAACA CAACCACCGA AAATCTCACT TTGTTTCAAC CCTGTGTTGA CGACCACAAG    660

TGATTCCTGT TCCTGCCCCT TTACACCTAT AAATAATCAG CCATTTCCCT TCCATTTTCC    720

TCACCCCCAT TGGGCCATAA TCCATTCCCA AACAAAGATA CATAGTTGTT TCTGATTGGC    780

TTAGCTTTAG AACTTTCACC                                                800

(2) INFORMATION FOR SEQ ID NO:8:

(i) SEQUENCE CHARACTERISTICS:
        (A) LENGTH: 1138 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:8:

```
GCTTGACTTT AATCAAACCG GTATATATAA ACTAAAAAAA CGAAGGGAGT ACTACATACT    60

AGCTTTATAA TACTAGTACT GGATAAAATC TGCCACAGAA AGATTTTAGC GGGGAGAAGG   120

AGCATCATAG ACTGACTGAA TGATAGAAGT GTTTTCACCG GCGGTGCATT GCTTTCAATC   180

AATCCATTGA AATGGAGTCC AGCTGCTTAC CCTAATCTAA TCACAGGATG AGCCCATGGA   240

TCTAGCTGCA GTACCTCGAC TCCACCGGAA AGGAGCGGGC CCGTGTCGGT AGCGTTGCTC   300

CGGCTGGGTC CAGCACGACC CGACCGCGGC ACGCGTGGCG TTGGATTTGG AGATTCGGGC   360

TCCTGATTGT GATGCGAGTC TGCAACATGC ACAGCCATGT GACCTGCATT GATTCCTGCC   420

AGCCACTGTG CTGTGTGTGA GACCTGACCT GCACAAGAAC GGATCAAAGC TGGGGCCGGC   480

CCTTCGCGGC ATCATCAACC TCTCAAAAAC TCGTGTAAAA ACAGGTTCAC AAAATAACTC   540

ATCTGAAACA ACTCCTCAAA ATCTGACGCA GAAATGAGCC TTCTATAGAG TAGAAGAAAC   600

AGCAAATGCT GCAAAAGGCG AAAAGGCTGG TCCGTCGAAT GAAATTCTGA TACTATTGCC   660

TCGATTCAAC ATATATATAC TTATAATCCA AACAAGAAAT CGTACTGTAC TCCGATCCGA   720

TGGCAAATAA ATCAGTGGCA ATGGCAGCAA GTTGCGAGGT GTGCATGATC CGTGGATCAA   780

TCAACAATGC TTGATTTGCT CGCACTGGGC CAACCTGACA CGCACAAGAC AAGCATTGCA   840

CCTCGCAAGC ACCTCACTCC ACAGCGTCCC CATGCACTGG ATGCAGCTGG CTCACTCATC   900

ACTCGATTGC CATCGCTCGA TCCATCATGT TCATTTAGTG CCACGTCAAA ACAGATTATT   960

TTTATTTCGC CAAGCAACCA ATAATGTACT CCAAGAACCT ACGTACAGTG AGCTCACACT  1020

AGCTATAAAT ACACACAGGC TTCTTCGTCT TCGCATCCAC CACTCGCCCA TTGTTTGTAG  1080

TACCAACCAG CCAAGCCAAG AAGTAACAGA GAAGGAGGAA GAGAGGCCGG CCGGCGAA    1138
```

(2) INFORMATION FOR SEQ ID NO:9:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
CTTCAGCATG CACATCAAGC TCGTCGCCGG CGACTCCGCC GGCACCGTCA CCGCCTTCTA    60

CCTGTCGTCG CAGAACTCGG AGCACGACGA GATCGACTTC GAGTTCCTGG GGAACAGGAC   120

GGGGGAGCCG TACATCCTGC AGACGAACGT CTTCTCCGGC GGGAAGGGGG ACC          173
```

(2) INFORMATION FOR SEQ ID NO:10:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
TGAAGCTCGT CGGCGGCGAC TCCGCGGGCA CCGTCACGGC CTTCTACCTG TCGTCGCAGA    60

ACTCGGAGCA CGACGAGATC GACTTCGAGT TCCTGGCA                            98
```

(2) INFORMATION FOR SEQ ID NO:11:

(i) SEQUENCE CHARACTERISTICS:
            (A) LENGTH: 1130 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

GGTTTCCCTT GTTAACATGG CTTCTCCTTT GTTGATTTTG TGTCTTGTTC TGGTTTCGCT       60

AGCCTCTGCT GCACTCTGTG CGGCCCCACG GAGACCAGTG GATGTTCCAT TTGGCAGAAA      120

CTACATTCCC ACATGGGCTT TCGATCACAT CAAATACTTC AATGGGGGTT CTGAGATTCA      180

ACTTCATCTT GACAAGTACA CTGGCACTGG TTTCCAAACA AAAGGGTCCT ATCTGTTTGG      240

TCACTTCAGC ATGAACATAA AGATGGTTCC TGGTGATTCA GCTGGCACAG TCACTGCTTT      300

TTATTTATCA TCTCAAAACG CGGAGCACGA TGAGATAGAC TTTGATTTCT GGGGAACAG       360

AACAGGACAA CCTTACATTT TACAGACAAA TGTGTTCACT GGAGGGAAGG GTGACAGAGA      420

GCAAAGAATC TATCTTTGGT TTGATCCCAC AAAAGCGTAT CACAGATATT CTGTACTATG      480

GAACATGTAT CAAATTGTAT TCCTAGTGGA TAACATCCCA ATCAGGGTGT TCAAGAACCT      540

GAAGGAGTTG GGAGTGAAGT TTCCCTTTAA CCAACCGATG AAGGTTTACA ACAGTTTATG      600

GAATGCTGAT GATTGGGCCA CAAGGGGTGG TTTGGAGAAA ACAGATTGGT CAAAAGCTCC      660

ATTCGTAGCA GAGTACAAGG GGTTTCATGT TGATGGGTGT GAGGCTTCAG TGAATTCAAG      720

GTTCTGTGCC ACACAGGGTA AGAGATGGTG GGATCAAACA GAGTTTCGTG ATCTTGATTC      780

CTTTCAGTGG CGAAGACTCA AATGGGTGCG TCAGAAATTC ACCATCTACA ACTACTGCAC      840

TGACAGAACC CGCTACCCTC AACTTCCACC AGAATGCAGA AGAAACCGTG ACATTTAAAT      900

TTTCATCTGC TGTTTTTATC ACTTATTTCT GTGTTCTACA ACAACTTTCT CACTGCATTC      960

ATCATTTACC AGTTACCATA CTTTATTCCT ACCATTATTT ATTACCATTG TATTGTTTGG     1020

AATGTGTAAT TAAGGCCTTG GGGTCTGAAT ACAGAGGAAA CTCTATAATA AAACTACGTA     1080

TGTTATGTAA TTCTATTCTT ATACTTGGGC ACCACCAATA ATGTAATATT                1130

(2) INFORMATION FOR SEQ ID NO:12:

(i) SEQUENCE CHARACTERISTICS:
            (A) LENGTH: 1068 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

CAGAAAATGG TTTCTTCTTT GTGGACCGTG TCTCTGATAT TGGCATCGCT GGCCTCTGCA       60

GCAGTTTGTG CCAACCCGAG GAGGCCAGTG GATGTACAAT TCGGTAGAAA CTACGTTCCT      120

ACATGGGCTT TTGATCACAT CAAATACTTC AATGGTGGTT CTGAGATTCA ACTTCATCTT      180

GACAAGTACA CTGGTACTGG CTTTCAGTCC AAAGGGTCAT ACTTGTTTGG CCATTTCAGC      240

ATGTACATAA AGATGGTTCC TGGAGATTCA GCTGGCACAG TCACTGCCTT CTATTTATCT      300

TCTCAAAACG CGGAGCACGA TGAGATAGAC TTTGAGTTCT GGGGAACAG AACAGGACAA       360

CCTTACATTT TGCAAACAAA TGTGTTCACC GGAGGAAAGG GTGACAGAGA GCAAAGAATC      420

TATCTCTGGT TTGACCCCAC CAAAGCATAT CACAGATACT CTATTCTCTG GAACTTGTAT      480

CAGATTGTGT TCTTTGTTGA CGATGTGCCG ATCAGAGTGT TCAAGAACAG CAAGGACTTG      540

```
AGAGTGAAGT TTCCATTCGA CCAACCTATG AAGCTATACA ACAGTTTGTG GAATGCTGAT        600

GACTGGGCAA CAAGGGGTGG TTTGGAGAAA ACAGATTGGT CGAAAGCTCC TTTCGTAGCA        660

GGGTACAAGG GGTTCCACAT CGATGGGTGC GAGGCCTCTG TGACCGCTAA GTTCTGCGAC        720

ACACAGGGCA AGAGATGGTG GGACCAACCA GAGTTTCGTG ACCTTGACGC CGCTCAATGG        780

CAAAGACTCA AATGGGTGCG TCAGAAATTC ACCATCTACA ACTACTGCAC TGACAGAAAA        840

CGCTACCCTC AACTTTCCCC TGAATGCAGT AGAGACCGCG ACATTTAAAT TTTCACATAC        900

TTCTGTTACC ATTTACTTTT ACCAGATTGT TGTCACTTTC ATGTACAATT TTATATCACG        960

TCAAATCTAT CCATTGCCAC TTTATTTATG AATTGAAATT TGCTTCAGAT AAAAAAATTA       1020

TAAATAAACA CAGTTTTTCT TAGAAAAAAA AAAAAAAAAA AAAAAAA                     1068

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GATGAGATAG ACTTGAGTTC TTGGG                                               25

(2) INFORMATION FOR SEQ ID NO:14:

(i) SEQUENCE CHARACTERISTICS:
        (A) LENGTH: 1017 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GAAACAATTT CACTCAGTTT CACACAAAAC AATTCTGCAT GGCATTTTCA AGACTTTTAC         60

TGTTAACATG CATTGTTGGG TATTTTCTGA TTGCCTCTGC ATCCAATTTC TATCAAGATT        120

TTGAAATAAC CTGGGGAGAT GGTCGTGCCA AGACACTAAA CAATGGCGAC CTTCTTACTT        180

TGTCTCTTGA CAAAGCCTCT GGCTCCGGCT TCAGTCAAA  GAATGAATAC CTTTTTGGCA        240

AAATTGACAT GCAACTCAAA CTAGTCCCCG GCAACTCTGC TGGCACCGTC ACTGCCTACT        300

ATCTGTCTTC AAAAGGAGCA ACGTGGGATG AGATTGACTT TGAATTCTTG GGGAATTTGA        360

GCGGTGATCC TTACATTCTC CACACCAACG TGTTTAGCCA AGGCAAGGGT AATAGGGAGC        420

AACAATTCTA CCTCTGGTTT GACCCAACTG CTGATTTTCA CACCTATTCC ATCCTCTGGA        480

ACCCTCAACG TATTGTATTC TCTGTGGATG GAACTCCAAT AAGGGAGTTC AAGAACATGG        540

AGTCAAAGGG TGTTCCATTC CCCAAAAACC AAGCAATGAG GATATACTCA AGCCTTTGGA        600

ATGCAGATGA TTGGGCCACA AGGGGAGGGC TTGTTAAAAC CGATTGGAGC CAAGCTCCAT        660

TCACGGCTTC ATACAGAAAC TTCAATGCCA ATGCTTGCAC TGTGTCCTCT GGAACTTCTT        720

CTTGTTCAAA CTCTGTCTCT TCTCCCAATG CTTGGCTCTC GGAAGAATTG GACTCTACTA        780

ACCAGGAGAG ACTGAAGTGG GTACAGAAGA ATTACATGAT CTACAACTAT GCACCGACG         840

CCAAAAGATT TCCACAGGGC CTTCCTACAG AGTGCAACAC TGCCTAATTT TTCTTATCAA        900

TCCTTTCCAT GCTCCACTTT CTTTTTTATT TCTTCTGTTG TACTTTCCAT CATGATCAAT        960
```

TCTTTTATTC ATTGTAAAAC ATTGCTATCA TGATAAGTTT TCTTAAATAT TTCATAA    1017

(2) INFORMATION FOR SEQ ID NO:15:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GATGAGATTG ATTTTGAGTT CTTGGGGAAC CGTAGTGGTC AGCCTTACAC AGTTCAGACA    60

AATATCTACG CTCATGGAAA AGGGGATAGA GAGCAAAGGG TGAACCTCTG GTTTGATCCT    120

TCCGCGGATT TTCACACCTA CACTATCATG TGGAATCATC ACCATATTGT GTTCTACGTT    180

GATGATTTTC CCATTAGAGT GTACAAGAAC AATGAAGCGA AGGGAATCGC ATACCCAAAG    240

ATGCAGGCTA TGGGAGTGTA TTCGACGTTG TGGGAAGCTG ATAACTGGGC AACAAGAGGG    300

GGATTGGAGA AAATCGATTG GAGTAAGGCA CCATTTTATG CATATTACAA GGACTTTGAC    360

ATTGAAGGGT GCCCAAGTCC AGGACCTGCT AACTGTGCCT CTAATCAAAG TAATTGGTGG    420

GAAGGAGCTA CATACCAAGC TCTTAATGCC ATGGAAGCTC GAAGGTACAG GTGGGCTCGT    480

CTTAACCATA TGATCTATGA TTACTGCCAA GATAAGCCAA GGTACACGGT CATCCCACCA    540

GAGTGCCTTG CCGGCATTTA AACCCAAGAA CTCAAAATCA ATCTCATC    588

(2) INFORMATION FOR SEQ ID NO:16:

(i) SEQUENCE CHARACTERISTICS:
        (A) LENGTH: 854 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CTGTCTTTGG ACAAAGTTTC TGGCTCTGGT TTTCAATCTA AGAAAGAGTA TCTCTTTGGG    60

AGAATTGATA TGCAAATCAA ACTTGTTGCT GGAAATTCTG CTGGAACTGT CACTACATAC    120

TATTTATCTT CTCAGGGACC CACACATGAT GAAATTGACT TTGAATTCTT GGGAAATGTT    180

ACTGGTGAAC CTTATATTCT CCACACAAAC ATTTATGCCC AAGGCAAAGG AAACAAAGAG    240

CAGCAATTTT ACCTTTGGTT TGATCCTACC AAGAACTTCC ACACCTACTC AATCATATGG    300

AAACCCCAAC ATATCATTTT TTTGGTCGAC AACACACCAA TAAGAGTTTA CAAGAATGCT    360

GAATCCATTG GTGTGCCATT TCCCAAGAAC CAGCCCATGA GAATTTACTC TAGCCTTTGG    420

AATGCTGATG ATTGGGCAAC AAGAGGAGGC CTAGTGAAAA CTGATTGGTC TAAAGCACCA    480

TTTACAGCCT ACTATAGAAA TTTCAATTCT CAAACTTTTA GCAGTTCACA ATTTTCAAAT    540

GAAAAATGGC AAAATCAAGA ACTTGATGCC AATGGCAGAA AAGACTCAG ATGGGTGCAG    600

AGGAATTTCA TGATTTATAA TTATTGTACT GATTTTAAGA GGTTTCCTCA GGGTTTTCCT    660

CCAGAATGCA AAAGATTTTG AGTGATATTA GTTGGTTTTT GTGTAATTCT TTGATGTGTT    720

TGTGGTTTTA TTTTGTTAGA TTATAGCAAC CAAAATAAAT GTATTTTTCT CGTTTTATTT    780

TGTATCTTTT TCGAAGCTTG TAGTTCATCT TGTATCTAAT TTGTTTGATA TCCTTTATGA    840

TAAAAAAAAA AAAA    854

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
ACACAAAATA CCAGTTCTCA                                                20
```

(2) INFORMATION FOR SEQ ID NO:18:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
GAATTCTGTG ATCTAGTCCT ACTATTCAAA CACTTTTAGG CCAAAGAAAA TTGAAACACA    60
AAATACCAGT TCTCAAATAC AATGAACATT ATTAATTATA ATTCAGTTAA AAGTCATTGA   120
TCAGAACAGC AGTGAAGGTT AGCTATAAGC GCGTTATAGG TGCAGGCAGA GTGTCGTGCC   180
TATATATACC CTTTGGAATG CACAAGTTGA AACACAAAAG AAAAATG                 227
```

(2) INFORMATION FOR SEQ ID NO:19:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
ACTCTTTGTA ATTTTATCGA AGAGTTAGTG TGCAATAGAA ATTTAACATT GAGTATTTAC    60
AATTGTTAAA ACTATACATT CACTTCATTT TCATGCATTT ATAAACATTT CAATTTCAAT   120
TTCATGTTAA AATCAACTCA AAGTAATACT CAAATCTTAT TCCTAGTGAC TTTAATATAT   180
TGTTAACTTA TCAAGTTTCA ATTCCTTCAA TCATCAACAA GCAATCAAGA ATTAAGTTCA   240
AGAGTCTTAA GATTACTAAT AAATCATGTT CTATCCCTAG ATATAAGCTT              290
```

(2) INFORMATION FOR SEQ ID NO:20:

(i) SEQUENCE CHARACTERISTICS:
        (A) LENGTH: 1654 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
AAGCTTTTTG CACATATTTG CAGCAGTAGA CAATGCCACT CGCTGAAAAA TATGATCTCC    60
CAGAATTTTG GCACAAAAAA TATATCCTAA CTAATATTTG ACTCTATCTA AGATACCACC   120
TGACATCAAA TGTTTCAATT TTATAGTCTT TAGCACGAGA AGATGTATAT TAGATATAAA   180
CCTTATCTTA TTTAATTAAT TTAGTAAGAT TGAATTAGAG GTAAATTTTA TTACTTAATA   240
```

```
TAATTAGACT ACTCATAAAT ATATAAATTT AAATTTTAAG TGTTCATTCC AATATATGAA      300

ATCTATTGAA AATATCACGT CAACTAATAA TATAACAAAA CTATAATATA AAAATAAGTA      360

TAAATTTTAT ATTTATAAAC AATTTTGACA TTAAATTAAA CTTAAATTTA TCTCTATTAA      420

TAATAATATT ATAAGACAAA TTACTCTGCT AAAATACAGA AAACAATATA TTTTTTTGAA      480

ACTTTGAAAT ATTATATTGT TGGATGATGT TGGATAATTA GAAAGGACAT ATTATATATA      540

TGTCACGTTG AGATGAGTGG CCCATTGCAC TGAAAATGAC TGACAAATGG TACTCTCAAT      600

CCCATCTTAT TCTCTGTTCA ATTTTTTTCA CTTGAAAACT CTTTTTCCCT ATGGAAAATA      660

GCAATAACTA CAATATCCTC GTTCTTCTT GTTAGCTCTT GGCTACAACT GTGTTCATCT      720

TCTCCACTTT CATCAATACA ATTCCAAACA GAATATACTT AGACCCTTCT GCTATTTCAA      780

GAAAGTAGCT TGCAAATTTG CTTTGTTTCC GACATACACT TCAATATGAA AAAAAAAAAA      840

AAAACACTTT GAGAACTTTT TAAAAAGTAT TAAGTAGGAT TTGACGGCAG AATTTTGTTT      900

CCATATTTAG TTGAAAATAC ATACAAAACG TATTTGAAAG TTATATTCGA TTGAATTTGG      960

TTTTAACATA GAAAAAATTC AACCAAATTA AGTCCATACT TAAGCATTAA TATAAATATT     1020

TCAGTTATTC GACTTCGGTT TCACGTCTTG CCATTGTTTT ACATGTGTAA TACTTCAATT     1080

AATTTTTTAT GTTTTCATGT CTCTTTATCC ACTCCCTTTA TTTTTACATT ATAATACCAC     1140

ATTCCTCCAA TACTATAATT CTTAAGATAT ATGTGAACAT TAATATCTAA TGATACATAA     1200

GGTAAGTTGT AAATATTCAT AGAAAAAATA AAATGACTTT TCAAGAAAAC CAACAACTAA     1260

ATATAAAATA TAGAAAAGTT ATTTACAATT TTGTCCGTTA ACATGTCCAG ATATTACACT     1320

CTCAAAAGAA AAAGTGTTAG AAAAATCATA TAAAATAGAG TTCAAATTCT TTGTTAGATT     1380

TTTTTTACTG AACATTAAAA ATATATATTG ATATTGATTA TTCATTTTTA TAAATATATT     1440

TTAAAATTAA CATTCAATAT ATATATTTTA AAATTAACAT TCAATATATA TATTTTAAAG     1500

ACACAGAAGA AACAACAAAT TCCATAAAAT TGTGAGATAA TATTTAACCC TAACTTTCTT     1560

ATGAACTGAG AGATTTTACA TTTATGAGAA ATGATTGTCC TGTGTTAATT ATCCATGTCA     1620

GCTACCTAAT CACTAGAAAA GCTAATCAGA ATTC                                 1654

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GAAGTAATAC TCAAATCTTA TTCCTAGTG                                         29

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CCCATTTTTC TTTTGTGTTT CAACTTGTGC                                        30
```

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
ACAAGCAATC AAGAATTAAG TTCAAGAGTC                                30
```

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

```
TAATAATGTT CATTGTATTT GAGAACTGGT                                30
```

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
GATTACTAAT AAATCATGTT CTATCCCTAG                                30
```

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
AAAGTGTTTG AATAGTAGGA CTAGATCACA                                30
```

(2) INFORMATION FOR SEQ ID NO:27:

(i) SEQUENCE CHARACTERISTICS:
        (A) LENGTH: 1744 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
AAGCTTCAAG TAAGTCTCTG TGATATGTAT GCAAGGGTTC GAAATGAGAA GAAGGCCCTT     60

CAAATTCTAG GTGTACTGGA ATCTAGGAAG GATGAATTAG GAAAAGCTGA TTTTGAGAGA    120

ATTATAAGTG GCCTTATTGA TGGTGGGTTT CGGCAAGATG CCCAACGAAT ATGTGGGATC    180

ATGGAGGCGC AGGATTTCGA TGCATCAAAG GTTAAGGTCA ACCTTATGAA GCCTGTCTCT    240
```

```
AGAGGACCTC GTATGAGATA GTTTAGTGGT CATGAATTGG GACATTTTAG TCTTTCTCTG      300

CAAGTGAGTT ACAAATGTAT TACCTTATAT AGGAAGCAAT GTCTGCATGA TTTATCATAC      360

CATGTAACAA ATAAGAATGA ATTTGTTTAT GGATTTTTCC ATTGCTCAGA TTCTGAATTT      420

ACGCAATTTT TTTTTTCTTT TGAACTTTAG TTGTTTGTAT ATACAAATGT CTTCTGTGGC      480

ATGTTCATGG AATTTTCATT TCCAATTATT CAATATTCTT GTGGTGTGAT CATCACTTTT      540

GTTAGGCAAA TCTGACAGCA CTGATGCCCC CTATCAGGAT TTTTAAACTT GTATGCGGTA      600

TACTATACTG ATCACAAGAT ACAAACTAAT ATAAATGGAT AGGAAATGCA GATGGGATGG      660

TTCAAGCTAG TCTTTAATAT TGAGATAGTA CAGAAAATGC AATGCCCAAA GTAAACAACG      720

CTGATATTTC AAAATCACAT ATTAAAGCTA AGTTGGTAG CAACTAGCGT GAGAGCATCC       780

TAGTCTAGAC TGTGAATGCA GTATTTATAC ACTACAATGA TCTAAATAAG ATGCTACTAA      840

TGCAATCATG CTTAATGTAA TATGAATTGA CTAAAGTAG CTTGCAAATT TGCTTTGTTT       900

CCGACATACA CTTCAATATG AAAAAAAAAA AAAACACTTT GAGAACTTTT TAAAAAGTAT      960

TAAGTAGGAT TTGACGGCAG AATTTTGTTT CCATATTTAG TTGAAAATAC ATACAAAACG     1020

TATTTGAAAG TTATATCCGA TTGAATTTGG TTTTAACATA GAAAAAATTC AACCAAATTA     1080

AGTCCATACT TAAGCATTAA TATAAATATT TCAGTTATTC GACTTCGGTT TCACGTCTTG     1140

CCATTGTTTT ACATGTGTAA TACTTCAATT AATTTTTTAT GTTTTCATGT CTCTTTATCC     1200

ACTCCCTTTA TTTTTACATT ATAATACCAC ATTCCTCCAA TACTATAATT CTTAAGATAT     1260

ATGTGAACAT TAATATCTAA TGATACATAA GGTAAGTTGT AAATATTCAT AGAAAAAATA     1320

AAATGACTTT TCAAGAAAAC CAACAACTAA ATATAAAATA TAGAAAAGTT ATTTACAATT     1380

TTGTCCGTTA ACATGTCCAG ATATTACACT CTCAAAAGAA AAAGTGTTAG AAAAATCATA     1440

TAAAATAGAG TTCAAATTCT TTGTTAGATT TTTTTTACTG AACATTTAAA ATATATATTG     1500

ATATTGATTA TTCATTTTTA TAAATATATT TTAAAATTAA CATTCAATAT ATATATTTTA     1560

AAATTAACAT TCAATATATA TATTTTAAAG ACACAGAAGA AACAACAAAT TCCATAAAAT     1620

TGTGAGATAA TATTTAACCC TAACTTTCTT ATGAACTGAG AGATTTTACA TTTATGAGAA     1680

ATGATTGTCC TGTGTTAATT ATCCATGTCA GCTACCTAAT CACTAGAAAA GCTAATCAGA     1740

ATTC                                                                  1744
```

(2) INFORMATION FOR SEQ ID NO:28:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Asp Glu Ile Asp Phe Glu Leu Gly
1               5

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GGAAGCTTGA ATTCTGTGAT CTAGTCCTA  29

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GGTCTAGATC CAAAGGGTAT ATATAGGCA  29

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

ATCCACTGGT CTCCGTGGGG CGCACAGAG  29

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

AACTTTCTCA CTGCATTCAT CATTTACCAG  30

(2) INFORMATION FOR SEQ ID NO:33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

AGGCTAGCGA AACCAGAACA AGACACAAAA  30

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

CATACTTTAT TCCTACCATT ATTTATTACC  30

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

AATTTGGTCT CAACTGCAGT TCGTCAACCC G                            31

(2) INFORMATION FOR SEQ ID NO:36:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: peptide (xi) SEQUENCE DESCRIPTION: SEQ ID NO:36:

AATTCGGGTT GACGAACTGC AGTTGAGACC A                            31

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

ATCCACTGGC CTCCTCGGGT TGGCACAAAC                            30

(2) INFORMATION FOR SEQ ID NO:38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CTTTTACCAG ATTGTTGTCA CTTTCATGTA                            30

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

CTGCAGAGGC CAGCGATGCC AATATCAGAG                            30

(2) INFORMATION FOR SEQ ID NO:40:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:40:

TCTATCCATT GCCACTTTAT TTATGAATTG                               30

(2) INFORMATION FOR SEQ ID NO:41:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:41:

ATTGGATGCA GAGGCAATCA GAAAATACCC                               30

(2) INFORMATION FOR SEQ ID NO:42:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:42:

CTACAGAGTG CAACACTGCC TAATTTTTCT                               30

(2) INFORMATION FOR SEQ ID NO:43:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:43:

CAATGCATGT TAACAGTAAA AGTCTTGAAA                               30

(2) INFORMATION FOR SEQ ID NO:44:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:44:

CTCCACTTTC TTTTTTATTT CTTCTGTTGT                               30

(2) INFORMATION FOR SEQ ID NO:45:

(i) SEQUENCE CHARACTERISTICS:
            (A) LENGTH: 30 base pairs
            (B) TYPE: nucleic acid
            (C) STRANDEDNESS: single (D) TOPOLOGY: linear (ii) MOLECULE TYPE: cDNA (xi) SEQUENCE DESCRIPTION: SEQ ID NO:45:

GGATACCCAC AAAATACAAC AAGTGACAAA                             30

(2) INFORMATION FOR SEQ ID NO:46:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

CAAAGTGCTT TTAATTGAGC TGTATTTCCC                             30

(2) INFORMATION FOR SEQ ID NO:47:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

AAAACTCCTT TTATGATACC CATGGTGAGA                             30

(2) INFORMATION FOR SEQ ID NO:48:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

TTTTTGAGTG TATCATTATT GGTGGAGTCA                             30

(2) INFORMATION FOR SEQ ID NO:49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

ATCAGAGACC AGTGTTTGTG TATTTTTCGC                             30

(2) INFORMATION FOR SEQ ID NO:50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

GATATTATGT ATCTCATGCC AGGCCTTTCA                                    30

(2) INFORMATION FOR SEQ ID NO:51:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:51:

AGGTACTTGA TGTGGTGACT AGCCCAACTG                                    30

(2) INFORMATION FOR SEQ ID NO:52:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:52:

GGTCTTCATG ACTCAGCGTG TAACGAGTGA                                    30

(2) INFORMATION FOR SEQ ID NO:53:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:53:

CTCATAGTTT TTCCAAAAGG GTACATCCAC                                    30

(2) INFORMATION FOR SEQ ID NO:54:

(i) SEQUENCE CHARACTERISTICS:
       (A) LENGTH: 35 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:54:

TATTGTAATT TATTGCACTA TTTGTTTTCT CTGAA                              35

(2) INFORMATION FOR SEQ ID NO:55:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:55:

GGGATACCCA CAAAGTCCTA GTAATGACAA                                    30

(2) INFORMATION FOR SEQ ID NO:56:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

AACCAATACT TATGAGTGTA GCACTATTGA ACAAC                                  35

(2) INFORMATION FOR SEQ ID NO:57:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

ATGTGCATGC TGAAGTGGCC GAAGAGGTAG                                        30

(2) INFORMATION FOR SEQ ID NO:58:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

ACTACCACTA GTTGTTGTTG TGCCGCTGGT                                        30

(2) INFORMATION FOR SEQ ID NO:59:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

ACGTAGTTCT TGTCGAACGG CACGTCCACC                                        30

(2) INFORMATION FOR SEQ ID NO:60:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

CGCTGAGACC TAGTAGTACG AGGAATTTGT                                        30

(2) INFORMATION FOR SEQ ID NO:61:

(i) SEQUENCE CHARACTERISTICS:

(A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:61:

CGCTGAGACC TAGTAGTACG AGGAATTTGT                                    30

(2) INFORMATION FOR SEQ ID NO:62:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:62:

TTGGAGCTCA TTTTAAATAT CTCTGTCCTT                                    30

(2) INFORMATION FOR SEQ ID NO:63:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:63:

CCTGTTCAAT TTGTGGTTCC                                               20

(2) INFORMATION FOR SEQ ID NO:64:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:64:

TTGTGGTCCA GGTCATGGTA                                               20

(2) INFORMATION FOR SEQ ID NO:65:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:65:

GGAAGCTTTT CGAAAATTTA TCATTATTGC                                    30

(2) INFORMATION FOR SEQ ID NO:66:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:66:

GGTCTAGATT TCTGTGTTTA TCTGTTTGTG G                                              31

(2) INFORMATION FOR SEQ ID NO:67:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:67:

ATGGCATTTT CAAGACTTTT ACTGTT                                                    26

(2) INFORMATION FOR SEQ ID NO:68:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:68:

GGGTGGTCAG TCCCTT                                                               16

(2) INFORMATION FOR SEQ ID NO:69:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:69:

GGAAGCTTGT TAAACTGATT TAAAAG                                                    26

(2) INFORMATION FOR SEQ ID NO:70:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:70:

GGTCTAGAGG TGAGAAAAAC AAATCCAAT                                                 29

(2) INFORMATION FOR SEQ ID NO:71:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:71:

```
GGAAGCTTTA TTAGGTCGAG TGAGATGGAT                                    30

(2) INFORMATION FOR SEQ ID NO:72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:72:

ATGGGTATCA TAAAAGGAGT TTT                                           23

(2) INFORMATION FOR SEQ ID NO:73:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:73:

AATCGGATCC CCGGGTGGTC AGTCCCTT                                      28

(2) INFORMATION FOR SEQ ID NO:74:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:74:

GGCTGCAGGT TAGATCCCGA ATAATTATCT TAC                                33

(2) INFORMATION FOR SEQ ID NO:75:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:75:

GGTCTAGAGG TGAAAGTTCT AAAGCTAAGC                                    30
```

PLANT PROMOTER AND METHOD FOR GENE EXPRESSION USING SAID PROMOTER

FIELD OF THE INVENTION

The present invention relates to plant promoters which are useful for development of new plant varieties employing the gene recombination technology and the plant engineering such as functional modification etc. as well as is useful for the plant cell engineering such as functional modification of plant culture cells producing useful metabolites, DNA fragments in which useful genes are ligated to the promoters in such state that the useful genes can be expressed, and vectors containing the DNA fragments. Furthermore, the present invention relates to plants or plant cells that are transformed with the DNA fragments or vectors containing the DNA fragments, or to transgenic plants regenerated from the plant cells. Still furthermore, the present invention relates to a method for cloning the plant promoters.

PRIOR ART

Improvement of plants utilizing the gene engineering techniques has recently been using practically [Science, 244, 1293–1299 (1989)]. In particular, remarkable able progress has been made in the transformation system utilizing Ti plasmid and Ri plasmid that are contained in soil bacteria, *Agrobacterium tumefaciens* and *Agrobacterium rhizogenes*, whereby the system can be applicable not only to tobacco, Arabidopsis, and petunia that have been hitherto transformed but also to dicotyledonous plants such as azuki bean [Abstracts of Presentation at the Yeeting of NIHON SHOKUBUTU SOSHIKIBAIYOU GAKKAI (Japanese Association for Plant Tissue Culture), P. 124 (1990)] and to monocotyledonous plants such as rice [The Plant Journal, 6, 271–282 (1994)]. Moreover, for monocotyledonous plants whose representative example is the rice plant, a method comprising preparing a protoplast and then transferring a gene therein by electroporation has been practically used [Nature, 338, 274–276 (1989)]. In addition, there are many examples where genes are directly transferred into plants using the particle gun method [The Plant Journal, 2, 275–281 (1992)].

As for promoters which induce the tissue-specific expression of useful substances or enzymes, there have been heretofore isolated genes that express specifically in respective tissues of seed [SHOKUBUTU SAIBOU KOUGAKU (Plant Cell Technology), 3, 568–576 (1991)], respective tissues of leaves and flowers [Science, 250, 931–936 (1990)], tuber [SHOKUBUTU SAIBOU KOUGAKU (Plant Cell Technology), 3, 577– 587 (1991)], tuberous root, and root nodule [Science, 250, 948–954 (1990)) and the expression by these promoters has been analyzed in transgenic plants.

However, most promoters that have been hitherto utilized for these vector systems are promoters originating from Ti plasmid contained in *Agrobacterium tumefaciens* and promoters originating from the genes of cauliflower mosaic virus (CaMV). These promoters constitutively express irrespective of growth stages and tissues of transgenic plants and can not be controlled. In addition, the expression level is low. Moreover, among promoters containing expression regulatory regions inducing the tissue-specific expression, none of the promoters induce the expression specifically at the site and the stage required for the reconstitution of plant cell wall xyloglucan.

Furthermore, in the field of plant cell engineering, even when one intends to produce a useful secondary metabolite in plant cells to be used for a plant tissue culture, there have been known many cases where the expression of an enzyme gene in a biosynthesis system of the metabolite is repressed due to the presence of a plant hormone essential for the cell growth, thereby repressing the production of the metabolite [Physiologia Plantarur, 80, 379–387 (1990)]. Therefore, it is extremely difficult to optimize the biosynthesis of a secondary metabolite by cells in the presence of a plant hormone necessary for the cell growth. Then, it is required to employ a two-stage culture method wherein the cell growth and the biosynthesis of a secondary metabolite are carried out under separate conditions [Nippon NOUGEIKAGAKU KAISHI (Journal of Agricultural Chemistry Society of Japan), 60, 849–854 (1986)).

Such repression can be considered to be caused by regulation of the promoter of an enzyme gene in a biosynthesis system by a signal from a plant hormone and the like to repress the expression.

Accordingly, it is considered that the biosynthesis of a secondary metabolite can be facilitated under cell growth conditions by transferring a chimeric gene, in which the above promoter is replaced by a promoter inducing the expression of a useful substance or enzyme abundantly during a cell growth period, into cells. Nevertheless, any promoter abundantly inducing the expression of a useful substance or enzyme especially during a cell growth period has not been known in the field. Therefore, if such a promoter abundantly inducing the expression of a useful substance or enzyme especially during a cell growth period is available, the biosynthesis of a secondary metabolite can be effected as cells grow and significant improvement in the productivity of the useful secondary metabolite can be expected.

Thus, promoters that can induce the tissue specific expression or that can control the expression with a plant hormone and the like have been desired in the plant engineering and the plant cell engineering.

OBJECTS OF THE INVENTION

The object of the present invention is to provide a plant promoter that can induce the tissue-specific expression especially at the site and the stage required for the reconstitution of plant cell wall xyloglucan and further can control the expression with a plant hormone and the like, a DNA fragment containing the promoter, a vector containing the DNA fragment, a plant or plant cells transformed with the DNA fragment or vector, or a transgenic plant regenerated from the plant cells, and a method for cloning the plant promoter.

SUMMARY OR THE INVENTION

The present inventors have directed their attention to the fact that the expression of an endo-xyloglucan transferase (EXT) gene originating from a plant and its family genes is tissue-specific and have expected that a promoter that can control the expression and its vector would be available. The present inventors have further expected that such promoter can be utilized for improvement of plant cells and plants. Then, the present inventors attempted to clone a region containing a promoter which was presumed to be located upstream from a plant EXT gene. However, it was difficult to clone the promoter of the EXT gene by a known plaque hybridization method because of the presence of many family genes including pseudogenes and a decrease in the plaque-forming ability of plaques obtained by preparing a phage having a fragment containing a region located in upstream from the EXT gene and its family genes and infecting a host with it.

Then, the present inventors have studied intensively. As a result, the present inventors have succeeded in cloning the promoter of the EXT gene and analyzed the promoter portion to determine its nucleotide sequence. This promoter portion was cleaved off and ligated to β-glucuronidase (GUS) gene originating from *E. coli* and the resultant chimeric gene was transferred into plant cells.

It has been confirmed that GUS gene is intensely expressed in the cells into which the gene was transferred. When, according to the same manner, nucleotide sequences of the promoter portions of family genes of EXT gene were determined and ligated to GUS gene originating in *E. coli* and the resultant chimeric gene was transferred into plant cells, the intense expression of GUS gene was also confirmed.

Furthermore, it has been confirmed by northern hybridization that the EXT gene containing this promoter is expressed in a tissue-specific manner especially at the site and the stage required for the reconstitution of plant cell wall xyloglucan and that there exists each of the EXT gene and its family genes containing the promoter which is expressed during the logarithmic growth phase or the stationary phase of culture cells. Thus, the present invention has been completed.

That is, in brief, the first aspect of the present invention relates to a plant promoter inducing the tissue-specific expression and is characterized in that the plant promoter can control the expression of a gene encoding an enzyme having the function to carry out the reconstitution of plant cell wall xyloglucan and, particularly, it has a promoter activity at the site required for the reconstitution of plant cell wall xyloglucan or has a promoter activity at the stage required for the reconstitution of plant cell wall xyloglucan.

The second aspect of the present invention relates to a plant promoter of the first aspect of the present invention and is characterized in that it is contained in any nucleotide sequence selected from SEQ ID NO 1, 2, 3, 4, 5, 6, 7, and 8 in the Sequence Listing.

The third aspect of the present invention relates to a plant promoter of the first aspect of the present invention and is characterized in that it is hybridizable to the nucleotide sequence in the second aspect and has a promoter activity in plants or plant cells, or in transgenic plants regenerated from the plant cells.

The fourth aspect of the present invention relates to a DNA fragment containing the plant promoter of the first, second or third aspect and is characterized in that it is ligated to the plant promoter in a state capable of expressing a useful gene.

The fifth aspect of the present invention relates to a vector and is characterized in that it contains the plant promoter of the first, second or third aspect or the DNA fragment of the fourth aspect.

The sixth aspect of the present invention relates to a plant or plant cells transformed with the DNA fragment of the fourth aspect or the vector of the fifth aspect. mode, or to transgenic plants regenerated from the plant cells.

The seventh aspect of the present invention relates to a method for producing protein characterized in that at least one of the transformed plant and plant cells and transgenic plants regenerated from the plant cells of the sixth aspect is used.

The eighth aspect of the present invention related to a method for controlling morphology of a plant and is char-acterized in that the DNA fragment of the fourth aspect or the vector of the fifth aspect is used.

The ninth aspect of the present invention relates to a method for cloning a plant promoter and is characterized in that a gene encoding an enzyme having the function to carry out the reconstitution of plant cell wall xyloglucan and, particularly, a gene encoding endo-xyloglucan transferase or its functional equivalent is used.

DETAILED EXPLANATION OF THE INVENTION

The "promoter" used herein contains a TATA box. region or TATA-box like regions which are located 20 to 30 base pairs upstream from the transcription initiation site (+1) and are responsible for initiation of the transcription by an RNA polymerase from an exact position. However, it is not necessarily limited to in front and behind these regions and may contain any other region which is required for association of a protein other than a RNA polymerase for regulation of the expression in addition to the above regions.

And, sometimes, the term "promoter region" is used in the present specification and this means a region. containing the promoter as described in the present specification.

The "promoter activity" used herein means the ability and function to produce a gene product of a useful gene outside or inside a host (a plant, plant cells or a transgenic plant regenerated from the plant cells), when the useful gene is ligated to a site downstream from a promoter in order to express and then the resultant gene is transferred into the host.

In general, the promoter activity is indicated as positive or negative, or strong or weak, by ligating a gene encoding a protein capable of easy assay (a reporter gene) to a site downstream from a promoter in order to express, transferring the resulting promoter into the host, and then measuring the expression level of the protein. Thus, when a useful gene is ligated to a site downstream from a promoter in order to express and then the resultant gene is transferred into a host, the confirmation of expression of a gene product of the useful gene outside or inside the host shows that the promoter has the promoter activity in the transferred host.

The phrase "a gene encoding an enzyme having the function to carry out the reconstitution of plant cell wall xyloglucan" used herein means a gene encoding an enzyme specifically expressed in the reconstitution of plant cell wall xyloglucan and, particularly, refers to a gene encoding endo-xyloglucan transferase (EXT) and family genes of EXT gene. Examples of family genes of EXT gene include BRU1 gene [Plant Physiology, 104, 161–170 (1994)], meri-5 gene [The Plant Cell, 3, 359–370 (1991)], and XRP gene obtained in the present invention.

The phrase "a site required for the reconstitution of plant cell wall xyloglucan" used herein means a site where a gene encoding an enzyme having the function to carry out the reconstitution of plant cell wall xyloglucan is expressed specifically and, in so far as the gene encoding the enzyme having the function to carry out the reconstitution of plant cell wall xyloglucan is expressed specifically, the site where the expression occurs is included in the site required for the reconstitution of plant cell wall xyloglucan as mentioned herein.

For example, sometimes, the specifically expression site of EXT gene which is one of genes encoding an enzyme having the function to carry out the reconstitution of plant cell wall xyloglucan differs from those of family genes of EXT gene even in the same plant. However, all of them are included in the site required for the reconstitution of plant cell wall xyloglucan as mentioned in the present specification.

The stage of plant growth for the reconstitution of plant cell wall xyloglucan" used herein means the stage when the gene encoding the enzyme having the function to carry out the reconstitution of plant cell wall xyloglucan is expressed specifically and, in so far as the gene encoding the enzyme having the function to carry out the reconstitution of plant cell wall xyloglucan is expressed specifically, the stage when the expression occurs is included in that required for the reconstitution of plant cell wall xyloglucan as mentioned herein.

For example, sometimes, the specific stage of EXT gene expression which is one of genes encoding an enzyme having the function to carry out the reconstitution of plant cell wall xyloglucan differs from those of family genes of EXT gene even in the same plant. However, all of them are included in the stage required for the reconstitution of plant cell wall xyloglucan as mentioned in the present specification.

For example, in culture cells, mitotic cells are abundant in the logarithmic growth phase and the synthesis and reconstitution of the cell wall are vigorously carried out. In the stationary phase, cells elongate actively and thereby the reconstitution of cell wall is required. Thus, the cell wall reconstitution is required in both phases. As described in Example 10 hereinafter, the expression stage in the culture cells for EXT gene originating from tobacco is completely different from that for the XRT gene, a family gene of EXT gene originating from tobacco. In other words, EXT gene originating from tobacco is intensely expressed specifically in the logarithmic phase, whereas the expression in the stationary phase is reduced to about one twentieth. In contrast, XRT gene, a family gene of EXT gene originating from tobacco, is intensely expressed specifically in the stationary phase. Thus, the stage for specific expression of enzymes exhibiting the same enzymatic activity is controlled by the promoter of the gene encoding the enzyme. Examples of the stage for the reconstitution of plant cell wall xyloglucan as mentioned herein also include the logarithmic phase and the stationary phase in such cases.

The term "a functional equivalent" used herein means as follows.

A naturally occurring protein is subject to various mutations in its amino acid sequences such as deletion, insertion, addition, and substitution of the amino acid(s) by modifications of the formed protein occurring in the living body and during the purification process, in addition to polymorphism and mutations of the gene encoding the protein. Nevertheless, there has been known the existence of a molecule that exhibits a physiological and biological activity substantially equivalent to that of the protein with no mutation. Such a molecule that has a different structure but possesses a substantially equivalent function is defined as a functional equivalent.

The same is true in the case where the above-mentioned mutations are artificially introduced into the amino acid sequence of protein. A variety of mutants prepared in such cases can be interpreted as functional equivalents in so far as they exhibit a biological activity substantially equivalent to that of the protein with no mutation.

For example, it is said that methionine residue existing in the N-terminus of protein expressed by *E. coli* is removed in many cases by the action of methionine aminopeptidase. However, sometimes, both proteins with and without methionine residue are formed depending on a particular type of protein. Nevertheless, the presence or absence of methionine residue does not influence the activity of the proteins in many cases. In addition, it has been known that a polypeptide obtained by replacing certain cysteine residue of interleukin-2 (IL-2) with serine residue maintains interleukin-2 activity [Science, 224, 1431–1433].

Furthermore, in the protein production by the gene engineering, protein is often expressed as fusion protein. For example, an N-terminal peptide chain derived from another protein is added to the N-terminus of the objective protein in order to increase an expression level of the objective protein. And, an appropriate peptide chain is added to the N-terminus or the C-terminus of the objective protein in order to facilitate purification of the objective protein by using a carrier having an affinity to the added peptide chain after the expression.

Moreover, it has been known that, for each of the amino acids in a gene, there are one to six codons (sets of three nucleotides) which define the particular one amino acid. Accordingly, there can be many genes which encode a particular amino acid sequence, though the number of the genes depends on the amino acid sequence. Genes do not always exist stably in the nature and mutations often occur on their nucleic acids. There is a case where a mutation occurring on a gene does not induce any change in the encoded amino acid sequence (called as a silent mutation) and, in such a case, it can be said that a different gene encoding the same amino acid sequence is formed. Therefore, even if a gene encoding a certain defined amino acid sequence is isolated, a possibility can not be denied that many types of genes encoding the same amino acid sequence may be formed during the passage of the living organism containing the gene.

Furthermore, it is not so difficult to artificially prepare many types of genes encoding the same amino acid sequence by employing a variety of gene engineering techniques.

For example, in the protein production by the gene engineering, when a certain codon used in the inherent gene encoding the objective protein is not frequently utilized in the host used, sometimes, a low expression level is experienced. In such a case, an attempt has been made to increase the expression of the objective protein by artificially replacing the said codon to another codon which is more popular in the host without influence on the encoded amino acid sequence. Needless to say, it is quite possible to artificially prepare a variety of genes encoding a certain amino acid sequence in this way. Accordingly, even these artificially prepared different genes are included in the present invention, in so far as they code for the amino acid sequences that can be deduced from the nucleotide sequences disclosed by the present invention.

Moreover, many of polypeptides, which undergo at least one of modifications of one or more amino acids by deletion, insertion, addition, and substitution in the amino acid sequence of the objective protein, have an activity functionally equivalent to that of the objective protein. Genes encoding such polypeptides are also included in the functional equivalent of the present invention irrespective of being isolated from nature or artificially prepared.

In general, in many cases, genes encoding the functional equivalents have homology. Therefore, genes hybridizable to EXT gene used in the present invention and encoding a polypeptide having the same function are also included in the functional equivalents of the present invention.

Examples of "a useful gene" mentioned herein include genes encoding proteins expressible in plants or plant cells or transgenic plants regenerated from the plant cells, antisense RNAs of genes originating from plants or plant cells or transgenic plants regenerated from the plant cells, genes encoding binding proteins of transcription factors originating from plants or plant cells or transgenic plants regenerated from the plant cells or decoys having sequences or analogous sequences of binding sites for the transcription factors and ribozymes cleaving mRNAs originating from plants or plant cells or transgenic plants regenerated from the plant cells.

Genes encoding proteins expressible in plants or plant cells or transgenic plants regenerated from the plant cells are exemplified by those originating from plants, but they are not limited thereto in the present invention and genes originating from microorganisms such as bacteria, yeasts, actinomycetes, fungi, ascomycotina, basidiomycotina etc. and genes originating from living organisms such as animals etc., as far as they can be expressed in plants or plant cells or transgenic plants regenerated from the plant cells.

"Decoys" mentioned herein are referred to DNAs genes encoding binding proteins of transcription factors originating from plants or plant cells or transgenic plants, regenerated from the plant cells or DNAs having sequences or analogous sequences of binding site for the transcription factors, which repress the action of the transcription factors upon transferring as "decoys" into cells.

"Ribozymes" mentioned herein are referred to molecules cleaving mRNAs for defined proteins to inhibit the translation of these defined proteins. Ribozymes can be designed from gene sequences encoding defined proteins. Examples of ribozymes mentioned herein include any ribozymes which can cleave mRNAs for defined proteins to inhibit the translation of these defined proteins regardless of their types such as hammer-head-type ribozymes, hairpin-type ribozymes, delta-type ribozymes, etc.

In so far as a plant having an enzyme which functions to carry out the reconstitution of plant cell wall xyloglucan, any plant can be used in the present invention. Examples of the plants include dicotyledonous plants such as azuki bean, soybean, Arabidopsis, tomato, potato, Brassica, sunflower, cotton, tobacco, etc. and monocotyledonous plants such as wheat, rice, corn, sugar cane etc., of which plants having EXT enzyme and EXT-analogous enzymes that are expressed in a tissue-specific manner are particularly employed:

EXT gene is a housekeeping gene of plants and thereby many family genes exist. As for DNA fragments containing promoter regions of these family genes, cloning of the promoter of EXT gene is not easy by a conventional plaque hybridization method owing to the presence of many family genes including pseudogenes and decrease in the plaque-forming ability of the plaque obtained when a phage having a fragment of a upstream region from EXT gene or its family genes is prepared and infected to a host. However, by overcoming these two problems, hybridization is applicable to any plants including dicotyledonous plants and monocotyledonous plants by employing cDNA of EXT gene and its family genes as a probe and genomic DNA as a target, and also isolation is possible by investigating PCR method in details.

As the probe, cDNA of EXT gene and its family genes of a plant different from the target species can be used. However, it is preferred for more effective hybridization to select cDNA from a plant of the same species as the target as the probe. The present inventors have isolated cDNAs of EXT gene from azuki bean (*Vigna angularis*), soybean (*Glycine max*), Arabidopsis (*Arabidopsis, thaliana*), tomato (*Lycopersicon esculentum*), wheat (*Triticum aestivum*), tobacco (*Nicotiniana tabacum*), rice (*Oryza sativa*), corn (*Zea mays*). Of these cDNA molecules, full-length or partial nucleotide sequences for azuki bean, soybean, Arabidopsis, tomato, and wheat as well as the restriction map for rice and the restriction map for corn have been described in EP-0562836 A1 (1993) and a partial nucleotide sequence for tobacco has been described in JP 7-79778 A. Also, partial nucleotide sequences for rice and corn are shown in SEQ ID NO 9 and SEQ ID NO 10 of the Sequence Listing.

The cDNAs of family genes can be isolated by using the full-length or partial cDNA of EXT gene as a probe. For example, cDNAs of the family genes can be isolated from a wide species of plants by using, as a probe, a sequence conserved between all of the above-mentioned cDNAs of EXT gene and a xyloglucanase gene of Tropaeolum majus [The Plant Journal, 3, 701–711 (1993)]. In addition, cDNAs of the family genes can be isolated from a wide species of plants by synthesizing a primer on the basis of the conserved region and then carrying out PCR [Consensus PCR; Molecular and Cellular Biology, 13, 4745–4752 (1993)].

Hereinafter, the present invention is explained in details for azuki bean as an illustration.

A cDNA library prepared by the method described in EP-0562836 A1 (1993) using seeds of azuki bean (WATANABE SHUSHI Co., Ltd.) can be utilized for searching clones transformed with family genes of EXT gene. The cDNA library is prepared, for example, by preparation of RNAs from azuki bean, followed by purification of poly (A)$^+$RNA using Oligotex-dT30 (NIHON Roche Co., Ltd.) and then, for example, by treatment with a reverse transcriptase using the poly(A)$^+$RNA and an oligo-dT primer to prepare cDNA. The cDNA library is prepared from the cDNA by using cDNA Synthesis Kit System Plus (Amersham). This cDNA library is utilized for plaque hybridization using the cDNA of EXT gene as a probe to obtain, for example, 96 positive plaques selected from 5×10$^4$ plaques. These plaques are amplified by the plate lysate method (T. Maniatis et al., Molecular Cloning, A laboratory Manual, Second Edition, Chapter 2, pp. 60–66, published by Cold Spring Harbor Laboratory Press in 1989), followed by dot hybridization to classify the plaques on the basis of the signal strength.

Phages are isolated from two plaques indicating the signal strength different from that of EXT gene of azuki bean and DNAs inserted therein are extracted. These DNAS are cleaved with restriction enzyme EcoR I (TAKARA SHUZO Co., Ltd.) and the lengths of DNA fragments are identified by agarose gel electrophoresis. The identifiers DNA fragments of about 730 bp, 430 bp, and 1090 bp are purified and subcloned at the EcoR I site of pUC18 (TAKARA SHUZO Co., Ltd.). The resulting plasmids are named as pVX44-1, pVX44-2, and pVX45-1, respectively. These plasmids are employed for determination of the nucleotide sequences of the DNA fragments according to the Sanger method using BcaBEST™ Dideoxy Sequencing Kit (TAKARA SHUZO Co., Ltd.), indicating that two genes of a high homology with EXT gene (azuki bean EXT) are cloned. Parts of their nucleotide sequences are shown in SEQ ID NO 11 and SEQ ID NO 12 in the Sequence Listing (azuki bean EXT 2 and azuki bean EXT 3).

The above-mentioned cDNA library is utilized for plaque hybridization using one of the above-mentioned conserved sequences (SEQ ID NO 13) as a probe to obtain, for example, 8 positive plaques searched from 8×10³ plaques. DNAs inserted in phage vectors of the plaques are extracted and, for example, a DNA fragment (about 1.2 kbp) of a high homology with EXT gene as well as with its family genes, the BRU1 gene [Plant Physiology, 104, 161–170 (1994)] and the meri-5 gene [the Plant Cell, 3, 359–370 (1991)] can be obtained. A part of this DNA nucleotide sequence is shown in SEQ ID NO 14 in the Sequence Listing (azuki bean XRP 1).

Furthermore, the above-mentioned cDNA library can be utilized, for example, for PCR using the above-mentioned, conserved sequence and oligo-dT primer. As a result, a DNA fragment of a family gene different from, for example, azuki bean EXT, azuki bean EXT 2, azuki bean EXT 3, and azuki bean XRP 1 can be obtained. A part of this DNA nucleotide sequence is shown in SEQ ID NO 15 in the Sequence Listing (azuki bean XRP 2).

In a plant other than azuki bean, plaque hybridization using one of the above-mentioned conserved sequences (SEQ ID NO 13) as a probe can be utilized to obtain a cDNA of a family gene. For example, a commercially available cDNA library of tobacco is utilized for plaque hybridization using one of the above-mentioned conserved sequences (SEQ ID NO 13) as a probe to obtain 30 positive plaques searched from about 3×10⁴ plaques. DNAs inserted in phage vectors of said plaques are extracted and, for example, a DNA fragment (about 1.2 kbp) of a high homology with EXT gene as well as with the BRU1 gene (Plant Physiology, 104, 161–170 (1994)] and the meri-5 gene [the Plant Cell, 3, 359–370 (1991)] can be obtained. A part of this DNA nucleotide sequence is shown in SEQ ID NO 16 in the Sequence Listing (tobacco XRP 1).

Next, for example, a genome DNA library of azuki bean can be obtained by preparing a genome DNA from the leaves of azuki bean by a conventional method, subjecting it to partial digestion using restriction enzyme Sau3A I, subjecting the partial digestion product, for example, to ligation to a vector λGEM-11 using λGEM-11 Xho I Half-Site Arms Cloning System (Promega Biotec) followed by packaging using an in vitro packaging kit (Stratagene), and then infecting the resulting fragment to a host. This library can be utilized, for example, for hybridization using a cDNA of EXT gene described in EP-0562836 A1 (1993) as a probe to search phages having a DNA fragment containing a promoter region of this gene. For example, 10 positive plaques are obtained from about 1×10⁵ plaques and DNAs inserted in phage vectors of the plaques are extracted to obtain DNA fragments of an average length of about 15 kbp. These DNA fragments are utilized for Southern hybridization using a DNA fragment containing a cDNA of EXT gene as a probe followed by subcloning the objective fragment to a plasmid vector to analyze a partial nucleotide sequence. As a result, for example, it can be confirmed that DNA. fragments inserted in phage vectors of all plaques have a sequence analogous to EXT gene.

These studies may suggest that cloning of regions containing promoters of EXT gene and its family genes can be easily carried out. However, in fact, the following two problems were caused and cloning of any promoter of EXT gene by a conventional plaque hybridization was failed.

The first problem is the existence of many family genes including pseudogenes that are not easily differentiated by conventional hybridization. Accordingly, in order to carry out cloning of genomic DNA clones that are true counterparts of the objective cDNA clones, it is necessary to analyze and determine all the nucleotide sequences of respective genomic DNAs after roughly screening genomic DNA clones that may be the counterparts. Alternatively, it is necessary to find out a nucleotide sequence that can distinguish respective genes in family genes by analyzing many family genes from cDNAs and then to carry out hybridization using its nucleotide sequence-specific oligo probe (SSOP) to define the genomic DNA clone.

The second problem involves a strong repressing action that is induced on transfer of DNA fragments containing promoter regions of EXT gene and its family genes as well as decrease in the plaque-forming ability that occurs on infection of phages in a host bacterium (E. coli). In fact, it is difficult to search for the above-defined phages containing promoter regions of EXT gene because formed plaques are extremely small as compared with normal phages. Such a problem has been revealed first in the course of repeated trial and error to isolate the objective promoter region and is quite unpredictable until cloning is actually carried out.

Then, the present inventors have intensive studied to solve the above-mentioned problems, resulting in the first successful cloning of a region containing the promoter of EXT gene, after steadily solving the problems one by one by utilizing a variety of gene engineering techniques including an improved PCR method.

Hereinafter, EXT gene and its family genes are collectively referred to as EXT-family genes in the following explanations.

Cloning of Promoter

In case where an influence by the above-mentioned repression of the plaque-forming activity exists, it is impossible to clone a promoter region of EXT gene, even after repeated screening from entire genomic DNA libraries. Then, it is conceivable to prepare short genomic fragments that are not susceptible to the repression and then carry out cloning under a minimized influence of the repression. For this purpose, it is required to subject genomic DNAS, first, to complete digestion with a variety of restriction enzymes followed by genomic Southern hybridization and then to deduce what size of DNA fragment having the terminal site of which restriction enzyme contains the objective promoter region of EXT gene.

A partial genomic DNA library of the thus-defined DNA size can be prepared by complete digestion of genomic DNAs with the thus-defined restriction enzyme and by recovering, from agarose gel, peripheral DNA fragments having the defined DNA-fragment size as an average.

As a result, a partial genomic DNA library that is condensed about more than ten-fold as compared with the original entire genomic DNA library can be obtained. For example, genomic DNAs prepared from the leaves of azuki bean by a conventional method are subjected to digestion with, for example, restriction enzymes BamH I, EcoR I, and Hind III (all: TAKARA SHUZO Co., Ltd.), followed by genomic Southern hybridization to indicate the formation of 2 or 3 bands, wherein the most intense band can be identified at more than 15 kbp by the BamH I digestion, at about 8.5 kbp by the EcoR I digestion, at about 8.5 kbp by the Hind III digestion, and at about 5.5 kbp by the EcoR I-Hind III double digestion.

Of these bands, the band identified at about 5.5 kbp by the EcoR I-Hind III double digestion is recovered from the agarose gel and subjected to ligation, for example, to the EcoR I and Hind III sites of λEXlox (Novagen), followed by packaging by an in vitro packaging kit (Stratagene) and infection to a host bacterium, thereby enabling to obtain a partial genomic DNA library with DNA fragments of an about 5.5 kbp size as an average that has the EcoR I and Hind III sites at both terminals and is more condensed as compared with the entire genomic DNA library. This condensed library is subjected to hybridization using the cDNA of EXT gene as a probe as described above to search for a phage having a DNA fragment containing the promoter region of this gene. For example, 8 positive plaques searched from $1.3 \times 10^5$ plaques are subjected to hybridization using an oligonucleotide VAN-U7 (SEQ ID NO 17), synthesized on the basis of a 5'-uncoded region of a lower homology with cDNAs of family genes other than EXT gene, as a probe, thereby confirming that, for example, 4 out of 8 plaques are DNA fragments containing the cDNA of EXT gene. λEXlox can be subjected to automatic subcloning, since infection of this DNA fragment to a host bacterium having the PlCre gene will convert a region subcloned automatically in the host to a pUC-type plasmid by automatic subcloning.

DNA sequencing analysis using the plasmids inserted with the DNA fragment, followed by comparison of the DNA fragment with the cDNA sequence of EXT gene, identifies whether the DNA fragment contains a promoter of EXT gene.

Parts of DNA nucleotide sequence of the thus-identified fragment are shown in SEQ NO 18 (upstream from EXT coding region) and SEQ NO 19 (downstream from the DNA fragment) in the Sequence Listing.

Hereinafter, a 5'-upstream from the EcoR I site is referred to as "the promoter-upstream region" and a 3'-downstream as "the promoter-downstream region", for convenience.

The plasmid integrated with the fragment is denoted as pVXG303, whereas *E. coli* JM109 strain transformed with pVXG303 is denoted and indicated as *Escherichia*, coli JM109/pVXG303 and has been deposited on Mar. 15, 1995 (the date of original deposit) at National Institute of Bioscience and Human-Technology, Agency of Industrial Science and Technology, Ministry of Industrial Trade and Industry (1-3, Higashi 1-Chome, Tsukuba-Shi, Ibaragi-ken, 305, Japan) under the accession No. FERM BP-5390, in accordance with the Budapest Treaty.

The promoter-upstream region can be obtained by cloning of the Hind III fragment of about 8.5 kbp that is identified as mentioned above. For this purpose, genomic DNAs of azuki bean are completely digested with restriction enzyme Hind III and then DNA fragments are recovered by separation by 0.7% agarose gel electrophoresis, in the same manner as described above. Also, complete digestion of λZAPII (Stratagene) with restriction enzyme Spe I (TAKARA SHUZO Co., Ltd.), followed by the fill-in reaction in the presence of dCTP and dTTP, forms a half-filled-in site. The fill-in reaction of the Hind III fragment (average: about 8.5 kbp) in the presence of dATP and dGTP, as described above, followed by ligation into the half-filled-in site of λZAPII, enables a trial to prepare a genomic DNA library.

However, the size of this λDNA is marginal for the packaging and thereby the titer of its library is expected to be not so high. In fact, the titer of this library is so low as to carry out screening effectively. This size is also too small to use a replacement-type phage vector such as λDASHII (Stratagene). In fact, the titer of a library, which is obtained by ligation of the recovered Hind III fragment (average: about 8.5 kbp) to the Hind III site of λDASHII is so low as to carry out screening effectively.

In addition, the only method would be to carry out screening from the entire genomic DNA library using λGEM11 (Promega Biotec) by using the cDNA of EXT gene as a probe. However, it is expected that any fragment containing the objective promoter of EXT gene could not be obtained because of the influence of plaque-forming repression as well as the existence of many family genes as described above.

Then, it is expected that the use of a newly cloned genomic fragment as a probe will result in a more intense hybridization by a fragment containing the objective promoter than in the case using cDNA. Therefore, it is desirable to carry out plaque hybridization using such a genomic DNA fragment as a probe and then screen plaques as many as possible.

As a result of this screening, for example, 20 positive signals are obtained from $2 \times 10^5$ plaques and further screening enables to isolate positive clones. However, the size of a plaque, obtained on the basis of a phage vector inserted with a fragment containing the objective promoter, is so small that minor contamination of other plaques will lead to an exclusive formation of DNAs originating from contaminating phages upon extraction of phage DNAs, as a result of preferential proliferation of the contaminating phages with a more rapid multiplying rate either in the plate lysate method or in a culture broth method.

In fact, these problems have not been expected at all until the screening is carried out. Thus, a plaque corresponding to the signal can be obtained by carrying out repeated secondary screening, where a diluted solution of a primary phage is thinly sprayed, or by further carrying out tertiary screening. Surprisingly in the tertiary screening, a careful examination of the plate can detect a plaque, which is much smaller than other negative plaques, at a position corresponding to the signal that can not be identified at first glance. The thus-obtained, very small plaque is handled so carefully as to prevent contamination of other plaques in order to proliferate only the phage originating from the plaque. Extraction of a DNA fragment inserted in the phage vector enable to afford, for example, a DNA fragment of an about 11 kbp length.

In addition, a clone containing the objective EXT gene can be effectively screened in the secondary screening by carrying out concurrently hybridization using an oligonucleotide VAN-U7 (SEQ ID NO 17), synthesized on the basis of a 5'-uncoded region of a lower homology with cDNAs of family genes other than EXT gene, as a probe.

Digestion of the DNA fragment with, for example, restriction enzyme Hind III (TAKARA SHUZO Co., Ltd.), followed by genomic Southern hybridization using the above-mentioned genomic DNA of EXT gene from azuki bean as a probe, enables to define a shorter DNA fragment containing a promoter region of this gene. This fragment is inserted into a restriction site of a plasmid and the plasmid inserted with the fragment can be transferred into an appropriate host. Also, DNA sequencing analysis using the plasmid inserted with said DNA fragment, followed by comparison of the DNA fragment with the cDNA sequence of EXT gene, enables to judge whether the DNA fragment contains a promoter of EXT gene. Furthermore, the fragment can be used for subcloning as a fragment containing the objective promoter-upstream region. The thus-obtained subcloned DNA fragment having Hind III and EcoR I at both termini is integrated into the Hind III and EcoR I sites of pUC118 (TAKARA SHUZO Co., Ltd.) to allow to determine the nucleotide sequence. FIG. 1 shows the restriction map of the fragment. This nucleotide sequence is shown in SEQ ID NO 20 in the Sequence Listing.

The plasmid integrated with the fragment containing the objective promoter-upstream region into the Hind III and EcoR I sites of pUC118 is denoted as pVXP101, whereas *E. coli* JM109 strain transformed with pVXP101 is denoted and indicated as *Escherichia coli* JM109/pVXP101 and has been deposited on Feb. 23, 1995 (the date of original deposit) at National Institute of Bioscience and Human-Technology, Agency of Industrial Science and Technology, Ministry of Industrial Trade and Industry (1-3, Higashi 1-Chome, Tsukuba-Shi, Ibaragi-ken, 305, Japan) under the accession No. FERM BP-5389, in accordance with the Budapest Treaty.

The above-mentioned procedures are not always applicable to cloning of a DNA fragment containing the objective promoter region. For example, this is the case when the fragment exerts a fatal or growth-regressing action against a host bacterium. In fact, the above-mentioned phage containing a promoter of EXT gene forms a plaque that is so small to be searched and applied for the screening.

Then, PCR method is conceivable as an alternative method for cloning a DNA fragment containing a promoter region of the EXT gene.

PCR method to amplify such an unknown sequence involves inverse PCR [The Plant Journal, 7, 157–164 (1995)] and PCR using a cassette [TANPAKUSHITU KAKUSAN KOUSO (Proteins, Nucleic Acids, and enzymes), 35, 3157–3163 (1990)].

However, conventional inverse PCR is effective only for amplification of DNA chains up to about 1 kbp in length, when a genomic DNA of a higher animal or plant is used as a template. Also, PCR using a cassette is similarly effective only for amplification of fragments up to about 1 kbp in length.

In addition, the selection of a restriction enzyme for self ligation is limited in inverse PCR, wherein the use of a restriction enzyme recognizing 4 bp is vital for obtaining an amplified fragment. In PCR using a cassette, it is required to test many cassettes having a variety of restriction enzyme sites recognizing 6 bp, thereby requiring a lot of labor. Moreover, there is a low probability that even a restriction enzyme site recognizing 4 bp, not to mention a restriction enzyme site recognizing 6 bp, exists for a DNA fragment containing an AT-rich, biased sequence like a promoter region, whereby amplification of a long target DNA is required both in inverse PCR and in PCR using a cassette. Then, the present inventors have found out that a conventional method capable of amplifying only short DNA chains can be improved so as to be capable of effectively amplifying DNAs larger than about 2 kbp in length by optimizing the self-ligation conditions and the use of TAKARA LA PCR Kit (TAKARA SHUZO Co., Ltd.) in inverse PCR.

In addition, the present inventors have found out that two-stage PCR procedures, wherein the reaction solution in a first PCR shall be diluted for the use as a template in a second PCR in order to amplify the objective DNA fragment effectively, thereby enabling to solve the above-mentioned problems.

For example, genomic DNAs prepared from the leaves of azuki bean are subjected to complete digestion using restriction enzyme Hind III, followed by self-ligation with T4 DNA ligase (TAKARA SHUZO Co., Ltd.). Since the efficiency of the self-ligation reaction is greatly dependent on the volume of this reaction system, it is preferred to adjust the volume of reaction system so as to make the DNA concentration less than 4 µg/ml.

PCR is carried out using the thus-obtained cyclic genomic DNA as a template. Examples of a primer to be employed include sequences such as primer VAN-UH1 (SEQ ID NO 21), primer VAN-L (SEQ ID NO 22), primer VAN-UH2 (SEQ ID NO 23), primer VAN-L16 (SEQ ID NO 24), primer VAN-UH3 (SEQ ID NO. 25), and primer VAN-L3 (SEQ ID NO 26), which are synthesized on the basis of sequences (SEQ ID NO 18 and SEQ ID NO 19) of the above-mentioned EXT gene genome DNA of pVXG303.

The two-stage PCR procedures are effective in order to amplify the objective DNA fragment efficiently. For example, a DNA fragment of about 1.8 kbp can be amplified by carrying out the first PCR using the above-mentioned primer VAN-UH1 (SEQ ID NO 21) and primer VAN-L (SEQ ID NO 22) as primers and then utilizing the resulting reaction product as a template for the second PCR using primer VAN-UH2 (SEQ ID NO 23) and primer VAN-L3 (SEQ ID NO 26).

However, the amplification is not efficient, if the first PCR is carried out in the same manner as described above and then the second PCR is carried out using primer VAN-UH2 (SEQ ID NO 23) and primer VAN-L16 (SEQ ID NO 24) or primer VAN-UH3 (SEQ ID NO 25) and primer VAN-L3 (SEQ ID NO 26) as primers. In other words, the amplification efficiency is dependent on the selection of primers. Accordingly, it is preferred to find out the most suitable combination of primers from several combinations made.

The PCR reactions shall be carried out by following the protocol of TAKARA LA PCR Kit (TAKARA SHUZO Co., Ltd.), except for the reaction temperature and the cycle conditions. Thus, the first PCR is carried out using 50 µl of the reaction solution at 94° C. (0.5 minute), 55° C. (1.0 minute), and 72° C. (2 minutes) with 30 cycles and then the second PCR is carried out under the same conditions. Hereupon, it is desirable to prepare several diluted solutions of the first PCR reaction solution in order to find out the best amount to be added in the second PCR.

The amplified product of about 1.8 kbp can be subcloned into, for example, the Hinc II site of pUC119 (TAKARA SHUZO Co., Ltd.). Comparison of nucleotide sequences at both termini of the fragment with the sequences (SEQ ID NO 18 and SEQ ID NO 19) of the above-mentioned. EXT gene genomic DNA, which previously are partially cloned, reveals whether said fragment is a DNA fragment containing a promoter of EXT gene that is continued from the previous sequences. FIG. 2 shows the restriction map of the fragment. The nucleotide sequence of the fragment is shown in SEQ ID NO 27 in the Sequence Listing. The plasmid integrated with this PCR product is denoted as pVXP-H3, whereas *E. coli* JM109 strain transformed with pVXP-H3 is denoted and indicated as *Escherichia coli* JM109/pVXP-H3 and has been deposited on February 17, 1995 (the date of original deposit) at National Institute of Bioscience and Human-Technology, Agency of Industrial Science and Technology, Ministry of Industrial Trade and Industry (1-3, Higashi 1-Chome, Tsukuba-Shi, Ibaragi-ken, 305, Japan) as the accession FERM BP-5388, in accordance with the Budapest Treaty.

SEQ ID NO *and SEQ ID NO* 2 in the Sequence Listing show nucleotide sequences upstream from a gene encoding the N-terminal amino acid sequence of EXT that are composed of SEQ ID NO 18 and SEQ ID NO 19 together with SEQ ID NO 27 in the Sequence Listing.

As a result of nucleotide sequence analysis and comparison of SEQ ID NO 1 with SEQ ID NO 2 in the Sequence Listing, it is revealed that both sequences are entirely the same except for only two differences in all regions downstream from the 782th residue A of SEQ ID NO 1 and downstream from the residue A of SEQ ID NO 2. These two differences involve a difference in the number of continuing A residues downstream from the 829th residue A of SEQ ID NO 1 and downstream from the 921st residue A of SEQ ID NO 2 (16 bases in SEQ ID NO 1 and 14 bases in SEQ ID NO 2) and a difference between the 947th residue T of SEQ ID NO 1 and the 1037th residue C of SEQ ID NO 2. This observation reveals that this common region possesses a region regulating the specific expression at the site and stage required for the reconstitution of plant cell wall xyloglucan.

A DNA fragment containing a promoter region of a family gene can be cloned by solving the problems in the same manner as the method for cloning a DNA fragment containing a promoter region of the EXT gene. Furthermore, comparison of the resulting cloned fragment with some of these family genes that surely are expressed specifically at the site and stage required for the reconstitution of plant cell wall xyloglucan enables to identify a region necessary for the tissue-specific expression in plants. Also, a region necessary for an especially intense expression at the logarithmic growth phase in culture cells can be identified in the same manner.

Measurement of Expression Site and Expression Stage—Northern Hybridization

In order to analyze the expression by a promoter, for example, the expression site and the expression stage in azuki bean plants can be measured by northern hybridization using EXT gene cDNA of azuki bean as a probe. Also, for example, the expression stage in tobacco culture cells can be measured by northern hybridization using EXT gene cDNA of tobacco as a probe.

The EXT gene cDNA of azuki bean and the EXT gene cDNA of tobacco can be cloned by methods described, for example, in EP-0562836 A1 (1993) and JP 7-79778 A.

RNA extraction from the azuki bean plants and plant tissues such as the tobacco culture cells can be carried out, for example, by the guanidine thiocyanate method or the phenol-SDS method. The thus-extracted total RNAs can be subjected to, for example, analysis by agarose gel electrophoresis, followed by transference on a membrane and then hybridization using this membrane. The total RNA level can be prepared in the same level, for example, by comparing the rRNA levels in the agarose gel electrophoresis, thereby enabling to correctly compare the levels of the expressed EXT gene mRNA.

For example, using azuki bean plants grown for 40 days after seeding, total RNAs, which are extracted from stems, buds, and leaves by the guanidine thiocyanate method, are subjected to agarose gel electrophoresis followed by northern hybridization using, as a probe, a DNA having a sequence specific to the EXT gene cDNA that is different from other family gene cDNAs. In this case, the filter obtained after the hybridization is washed under such intensified conditions that the above-mentioned probe having a sequence specific to the EXT gene cDNA can be paired only with an mRNA of the target EXT gene without pairing with other family gene mRNAs, thereby enabling the detection of only the expression of the objective EXT gene. Such expression can also be confirmed by the size of the mRNA. Comparison of the levels of the EXT gene mRNA in each plant tissue enables to reveal that the EXT gene mRNA is expressed in all sites and is intensely expressed, particularly in stems where the reconstitution of plant cell wall xyloglu-can is active. Furthermore, using azuki bean sprouts, the total RNA, which is extracted from every 1 cm-long cuts of epicotyl, is subjected to the analysis with agarose gel electrophoresis followed by northern hybridization using the EXT gene cDNA as a probe. In this way, it can be revealed that the expression is most intense in the site where the epicotyl grows greatly, namely, in the site where the reconstitution of plant cell wall xyloglucan is active.

The expression site for each family gene can be clearly defined by northern hybridization using a probe specific to the respective family genes, in the same manner as mentioned above.

Each of Tobacco BY2 culture cells [Fermentation Technology Today, p. 689, Issued by NIHON HAKKOU KOU-GAKUKAI (Japan Fermentation Technology Society) in 1972] cultivated for 1, 4, 6, 8, and 10 days is collected by suction filtration, immediately subjected to rapid freezing using liquid nitrogen, and then kept at −80° C. until RNA extraction is operated. The total RNA extracted from these cells by the phenol-SDS method can be subjected to the analysis by agarose gel electrophoresis followed by northern hybridization using a DNA having a sequence specific to the tobacco EXT gene cDNA as a probe. Comparison of the expression enables to reveal that the expression occurs in any time and is particularly intense at the logarithmic growth phase (4 days). It can be also revealed that, conversely, the tobacco XRP1 gene, a family gene, is expressed intensely at the stationary phase and is not expressed so intensely at the logarithmic growth phase.

Identification of Expression Site and Expression Stage by RT-PCR

Moreover, RT (Reverse Transcriptase)-PCR method can be employed to analyze simply the expression controlled by family gene promoters of these EXT genes.

For example, each of stems, buds, and leaves of azuki bean plants grown for 40 days after seeding is separately collected, immediately subjected to rapid freezing using liquid nitrogen, and then kept at −80° C. until RNA extraction is operated. The total RNAs are extracted from these tissues, for example, by the guanidine thiocyanate method. Each of the total RNAs can be used as a template for RT-PCR using TAKARA RNA PCR Kit (TAKARA SHUZO Co., Ltd.) to identify the expression site. In this case, the expression-site specificity controlled by each family gene promoter can be identified by using a sequence specific to the respective family gene as a primer.

For example, using azuki bean plants grown in the dark for 5 days after seeding, every 1 cm-long sections of epicotyl are separately collected, immediately subjected to rapid freezing using liquid nitrogen, and then kept at −80° C. until RNA extraction is operated. Each of the total RNAs, which are extracted from these tissues, for example, by the guanidine thiocyanate method, can be used as a template for RT-PCR using TAKARA RNA PCR Kit (TAKARA SHUZO Co., Ltd.) to identify the specificity of the expression site and stage in more details.

For example, each of Tobacco BY2 culture cells cultivated for 0, 1, 2, 4, 6, 8, and 10 days is collected by suction filtration, immediately subjected to rapid freezing using liquid nitrogen, and then kept at −80° C. until RNA extraction is operated. Each of the total RNAs extracted from these cells by the phenol-SDS method can be used as a template for RT-PCR using TAKARA RNA PCR Kit (TAKARA SHUZO Co., Ltd.) to identify the expression stage. In this case, the expression-stage specificity controlled by each family gene promoter can be identified by using a sequence specific to each of the tobacco EXT gene and its family gene as a primer.

Gene Direct Transfer and GUS-Activity Measurement—Transient Assay

The full length or a portion of a sequence containing the above-mentioned promoter is cut off and ligated to a variety of reporter genes to prepare chimeric genes. The promoter activity can be measured by direct transfer of such a chimeric gene into plant cells.

A reporter gene means a gene that is ligated at a downstream from the promoter region of the objective gene in order to examine the promoter activity of the gene or the action of other cis-elements. A coding region of an *E. coli*-origin enzyme gene is principally utilized as the reporter, since the cells to be transformed with the chimeric gene should not have the same or similar enzymatic activity.

Examples of such reporter gene in the case of plants include genes of GUS of the *E. coli*-origin, chloramphenicol acetyltransferase (CAT), β-galactosidase (lacZ), neomycin phosphotransferase (NPTII), luciferase, etc, of which GUS of the *E. coli*-origin recently has been well utilized particularly.

The GUS activity is assayed by using 4-methylunbelliferylglucuronide (4-MUG, WAKO Pure Chemicals Industries. Ltd.) as the substrate and measuring the specific fluorescence emitted from its product, 4-methylumbelliferone (4-MU, nacalai tesque). The measurement of 4-MU can be easily carried out, since it is highly stable and the background fluorescence is low. In addition, when 5-bromo-4-chloro-3-indolyl-β-D-glucuronide (X-Gluc, Molecular Probes) is used as the substrate, the product is an insoluble indigo-blue pigment, called indigotin, and thus by utilizing its property, a localization of the GUS activity in cells or tissues can be easily examined.

Comparison of the promoter activity can be made by using, for example, the cauliflower mosaic virus 35S promoter that is contained in pBI121 (Clontech) and pBI221 (Clontech).

The transcription can be efficiently terminated by linkage of a transcription-termination sequence at a downstream from the reporter gene. The transcription termination sequence may be originated from EXT gene or may be originated from another gene. In addition, the transcription efficiency can be enhanced by linkage of a poly-A addition sequence at a downstream from the inserted sequence. The poly-A addition sequence may be originated from EXT gene or may be originated from another gene, exemplified by Agrobacterium octopine synthetase [The EMBO Journal, 3, 835-846 (1984)] and Agrobacterium nopaline synthetase [The Journal of Molecular and Applied Genetics, 1, 561–573 (1982)]. Such a chimeric gene cassette can be inserted into an appropriate vector and amplified in *E. coli* as a plasmid in order to transfer directly into a living organism.

A method for introducing a vector containing this chimeric gene into a living organism is exemplified by the microinjection method [Molecular & General Genetics, 202, 179–185 (1986)], the polyethylene glycol method (Nature, 296, 72–74 (1982)], the particle gun method [Nature, 327, 70–73 (1987)], the protoplast fusion method with a cassette DNA or an RNA-containing small cells, cells, lysosome, etc. [Proceedings of the National Academy of Sciences of the USA, 79, 1859–1863 (1982)], the electroporation method [Proceedings of the National Academy of Sciences of the USA, 82, 5824–5828 (1985)], and so on.

A transient transcriptional expression of the thus-transferred gene in the cells for initial several days can be utilized for the transient assay to analyze an expression product in an extract of cells that are cultivated for 1 to 2 days after the transfer.

The plasmid vector that can be amplified in *E. coli* is exemplified by the cauliflower mosaic virus 35S promoter, the *E. coli*-origin GUS gene, and pBI121 (Clontech) having a transcription termination sequence cassette originating from nopaline synthetase. In order to remove the cauliflower mosaic virus 35S promoter region in the plasmid, this plasmid is subjected to digestion with restriction enzymes Hind III and Xba I (TAKARA SHUZO Co., Ltd.), followed by agarose gel electrophoresis to cut off the objective fragment other than the 35S promoter region. A DNA fragment containing a promoter region of the EXT gene can be transferred into this purified site.

The thus-prepared DNA fragment containing a promoter region of EXT gene and a vector containing a chimeric gene of GUS gene can be transferred into the tobacco BY2 culture cells by using, for example, the electroporation method.

In order to transfer into the tobacco BY2 culture cells by using the electroporation method, the tobacco BY2 culture cells can be converted to cell wall-free protoplasts by treatment with, for example, an enzyme solution (pH: 5.5) containing 1% cellulase-ONOZUKA (Yakult Honsha Co., Ltd.), 0.1% pectolyase Y23 (SEISHIN Corpolation), and 0.4 M mannitol at 30° C. for 2 hours. A suspension of the obtained $2 \times 10^6$ protoplasts of the tobacco BY2 culture cells in an electroporation buffer solution (70 mM KC1, 1.5 mM MES, and 0.3 M mannitol) is mixed with 3 pmol of a vector DNA and a 10% PEG6000/electroporation buffer solution. An electric pulse (300 V, 125 μF) using, for example, Gene Pulser II (Bio-Rad Laboratories) is applied to the resulting mixture to transfer the DNA into the plant cells. The cells are then incubated in the Linsmaier-Skoog culture medium (Physiologia Plantarum, 18, 100 (1965)] containing 0.2 mg/l 2,4-D as an auxin, 1% sucrose, and 0.4 M mannitol at 26° C. for 1 to 2 days after the transfer. The cells are extracted and GUS, the expression product, in the extract can be measured by the fluorescence analysis. That is to say, a mixture of the recovered cells in 200 μl of an extraction buffer solution [50 mM phosphate buffer (pH 7.0), 10 mM EDTA, 0.1% Triton X-100, 0.1% Sarkosyl, and 10 mM 2-mercaptoethanol] placed in an Eppendorf tube is subjected to ultra-sonication and a supernatant isolated by centrifugation is used for the assay of the GUS activity and the assay of the protein quantity to determine the GUS specific activity.

The GUS activity is assayed by measuring a specific fluorescence (excitation wavelength: 365 nm; fluorescence wavelength: 455 nm), for example, emitted by 4-MU, the product, when 4-MUG is used as the substrate. That is to say, 45 μl of the extraction buffer solution and 25 μl of 4 mM 4-MUG are added to react with each 30 μl of the extract placed in a 96-well microtiter plate. After 5, 35, and 95 minutes, the reaction is terminated by addition of 50 μl of a reaction-termination solution (1 M $Na_2CO_3$). Then, the specific fluorescence (excitation wavelength: 365 nm; fluorescence wavelength: 455 nm) emitted by 4-MU is measured with a fluorescence plate reader to assay 4-XU, the product, when 4-MUG is used as the substrate.

Moreover, the protein quantity is assayed by a procedure exemplified as follows. Thus, 2, 5, 10, 15, 20, and 30 μl of a ⅕-diluted solution of the extract or an 800 μg/ml BSA standard solution (20 μl of the extract buffer solution is mixed with 80 μl of 1 mg/ml BSA) are placed in a 96-well microtiter plate and thereto are added respectively 158, 155, 150, 145, 140, and 130 μl of distilled water and 40 μl of the assay reagent in Bio-Rad Protein Assay Kit (Bio-Rad Laboratories) to make a total volume to 200 μl, each. After being stirred slowly and then allowed to stand for 20 minutes at room temperature, the mixture is measured by a plate reader (wavelength: 590 nm) within 60 minutes to assay the protein quantity. At the same time when the above assays are carried out, the fluorescence intensities of the 4-MU standard solutions are measured and the results are plotted on a graph with the 4-MU quantity (pmol) at the x-axis and the fluorescence intensity at the y-axis. The 4-MU quantity per one fluorescence unit is obtained from the slope. Furthermore, the results on the samples are plotted on a graph with the time (minute) at the x-axis and the fluorescence intensity at the y-axis to obtain the increasing rate of the fluorescence intensity and then to obtain the decomposition rate of 4-MUG equal to the GUS activity. In addition, the GUS specific activity can be obtained from the amount of protein.

In this way, it can be confirmed that the DNA fragment containing the EXT gene promoter region exhibits an activity more intense than that of the cauliflower mosaic virus 35S promoter that has been said to be expressed intensely in the plants.

Transformed Plants

The thus-obtained DNA fragment containing the EXIT gene promoter region and the vector containing the inserted chimeric gene of the GUS gene can be transferred into plants or plant cells to prepare transformants.

The vector into which a chimeric gene is inserted is preferred to contain a selective marker gene so as to facilitate selection of transformed plants or plant cells. For example, a gene providing an antibiotic resistant property (antibiotic-resistant gene) can be utilized as the selective marker gene. Such a gene can be exemplified by genes providing a resistance against G418, hygromycin, bleomycin, kanamycin, gentamicin, and chloramphenicol. In the case where an antibiotic-resistant gene is integrated into a vector, the transformed plants or plant cells, namely, the plant or plant cells into which such a cassette is transferred, can be easily selected by picking up plants or plant cells that grow in a culture containing the antibiotic.

A method for introducing a vector containing the inserted chimeric gene directly into plants is exemplified by the microinjection method, the polyethylene glycol method, the particle gun method, the protoplast fusion method with a vector-containing small cells, cells, lysosome, etc., the electroporation method, and so on.

Moreover, a chimeric gene can be transferred into plants by utilizing a plant virus as a vector. For example, a cauliflower mosaic virus can be utilized as the plant virus. That is to say, a virus genome is first inserted in a vector of the E. coli origin to prepare a recombinant and then such a cassette is inserted into the virus genome. This cassette can be inserted into plants by cutting out the thus-modified virus genome from said recombinant using restrictive enzymes and then by inoculating the genome into plants (Molecular Biology of Plant Tumors, pp. 549–560, Issued by Academic Press in 1932 and U.S. Pat. No. 4,407,956).

Furthermore, such a cassette can be transferred into plants by employing such a property of a bacterium of the Agrobacterium genus that, on infection to a plant, a portion of its plasmid DNA is transferred into a plant. genome.

Of bacteria of the Agrobacterium genus, *Agrobacterium tumefaciens* infects a plant to induce crown galls and also *Agrobacterium rhizogenes* infects a plant to induce hairy roots, which are caused by the transfer of a region called as the transferred DNA region in a bacterial plasmid called as the Ti plasmid or the Ri plasmid into the plant to be integrated into the plant genome, when the bacteria infect the plant. In addition, there is another region called as the vir-region in the Ti plasmid or the Ri plasmid, which is essential for the T-DNA region to be transferred into the plant and then integrated into the plant. The vir-region itself is not transferred into the plant and also this vir-region can function on a plasmid other than that containing the T-DNA region [Nature, 303, 179–189 (1983)].

If the objective DNA to be integrated in the plant genome has been inserted into the T-DNA region on the Ti plasmid or the Ri plasmid, the objective DNA can be integrated into the plant genome when the bacteria of the Agrobacterium genus infect the plant. Then, the portion causing crown galls or hairy roots in the T-DNA region on the Ti plasmid or the Ri plasmid is removed without spoiling the objective transferring function and the resulting plasmid can be utilized as a vector. A variety of such vectors can be utilized in the present invention. For example, using pBI121 (Clontech) called as a binary vector, a GUS gene site linked to the cauliflower mosaic virus 35S promoter in pBI121 is replaced by the DNA fragment containing the EXT gene promoter region and the chimeric gene with the GUS gene to utilize for the transfer of said chimeric gene into the plant. In this case, a simultaneous usage of a vector having a promoter-free GUS gene (pBI101, Clontech) as a negative control, pBI121 (Clontech), etc. enables to compare with the expression mode of the cauliflower mosaic virus 35S promoter. Since such a vector does not have the vir-region, the bacteria of the Agrobacterium genus are required to contain another plasmid having the vir-region.

Moreover, this vector can be amplified not only in the bacteria of the Agrobacterium genus but also in *E. coli*. Accordingly, the recombinant operation of the Ti plasmid can be carried out using *E. coli*. In addition, this vector includes an antibiotic-resistant gene and thus the transformant can be easily selected, when *E. coli*, the bacteria of the Agrobacterium genus, and plants are transformed.

The transformation is applicable to any species of plants, provided that the plant can be infected by the bacteria of the Agrobacterium genus and establishes the regeneration system. Most of dicotyledonous plants can undergo transformation using the bacteria of the Agrobacterium genus and, particularly, all plants that are hosts of bacteria of the Agrobacterium genus in the nature can be transformed in vitro. Although monocotyledonous plants including cereals are not hosts of bacteria of the Agrobacterium genus in the nature, for example, rye plants [Nature, 325, 274–276 (1987)], maize plants [Science, 240, 204–207 (1988)], rice plants [Nature, 338, 274–276 (1989)], and so on can be transformed in vitro.

The transformation can be carried out (1) by using protoplasts and (2) by using a piece of tissues or untreated cells. For using method (1), it is required to establish in advance a system to regenerate the plant from transformed protoplasts. For using method (2), it is required to transform a piece of tissues or untreated cells by using the bacteria of the Agrobacterium genus and then establish a system to regenerate them in the plant. The transformed plant can be selected by growing in a culture medium containing an agent which can be the above-mentioned transformation marker.

The method for regenerating the plant from the plant cells, albeit different in the plant species, generally comprises deriving callus from a suspension of the transformed protoplasts in the case of (1) or from the piece of tissues or untreated cells that were transformed on the plate in the case of (2) and then forming shoots. In addition, the culture medium to be used for the regeneration may contain hormones such as auxin or cytokinin in addition to a variety of amino acids.

Whether the objective cassette is inserted into the genome of the transformed plant can be confirmed by Southern hybridization or the like, whereas whether the reporter gene mRNA is formed in the plant can be confirmed by northern hybridization or the like.

Utilizing the plant in which the chimeric gene prepared as described above is inserted, the chimeric gene can be transferred to the next generation of plants by mating.

For example, a plasmid containing the DNA fragment containing the EXT gene promoter region and the chimeric gene with the GUS gene to be obtained by the present invention can be constructed in pBI121 (Clontech). Next, the thus-constructed plasmid can be utilized for transformation of an appropriate strain of the Agrobacterium genus such as *Agrobacterium tumefaciens* LBA4404 strain [Nature, 303, 179–180 (1983); available from Clontech], followed by infection of the transformant to the objective plant to transform the plant.

For example, Arabidopsis seeds (available from Notlingham Arabidopsis Stock Center: NASC) are aseptically cultivated on an MSO plate [MURASHIGE-Skoog inorganic salt mixture (WAKO Pure Chemicals Industries., Ltd.), mixed with 2% sucrose, 3 mg/l thiamine hydrochloride, 5 mg/l nicotinic acid, and 0.5 mg/l pyridoxine hydrochloride, is adjusted to pH 6.3, mixed further with 0.2% gellan gum, autoclaved, and plated] according to a conventional procedure and then cut sections of the roots are used for callus culture on the CIM plate (0.5 mg/l 2,4-dichlorophenoxyacetic acid and 0.05 mg/l kinetin are added to the MSO plate).

Each of the Agrobacterium transformed by a plasmid containing the aforementioned chimeric gene and the Agrobacterium transformed by pBI121 and pBI101 is cultivated and the diluted mixture is distributed into tubes. Then, sections of roots that callus formed are soaked therein and co-cultivated on a CIM plate for several days. When each bacterial strain sufficiently grows to visible, they are killed by a bacteria specific antibiotic and sections of roots are cultivated further for several days on a SIMC plate [to the MSO plate are added 2-ip [N6-(2-isopentenyl)adenine (WAKO Pure Chemicals Industries, Ltd.)] at a final concentration of 5 µg/ml, IAA (3-indoleacetic acid, WAKO Pure Chemicals Industries, Ltd.) at a final concentration of 0.15 µg/ml, and Claforan (Hoechst) at a final concentration of 500 µg/ml]. The resulting sections are finally cultivated on the SIMCS plate (the SIMC plate containing kanamycin) and repeatedly transplanted on a new plate every week. The transformed cut sections keep growing to form swollen mass, whereas untransformed sections turn brown. The transformant is cultivated till formation of rosette leaves and the bottom of the transformant is cut off with a scalpel so as not to contain the callus part and transferred to a RIM plate (IAA is added at a final concentration of 0.5 µg/ml to the MSO plate). After 8 to 10 days, the cultivation is continued on a rock-fiber mini-box (NITTO BOUSEKI Co., Ltd.) soaked in an inorganic salt culture medium [Hyponecks (Hyponecks Japan)] is diluted 1000-fold with water]. After flowering and podding, the plant is transplanted in the soil soaked with the inorganic salt culture medium to obtain seeds. The seeds are sterilized and then sown and germinated on an MSK plate (kanamycin is added at a final concentration of 500 mg/l to the MSO plate) to obtain a transformant.

Whether or not the transformation occurs can be identified by extraction of a DNA from this transformant by a conventional method, cleavage of the DNA with restriction enzymes Hind III and EcoR I, and Southern hybridization using, as a probe, a promoter region that is prepared by digestion of pVXP-H3 with restriction enzymes Hind III and EcoR I. That is to say, when the above procedure is carried out on (1) the WS strain that does not undergo the transformation, (2) the transformant in which the chimeric gene is transferred, and (3) the transformant in which only the vector pBI121 is transferred, a specific signal of about 1.8 kbp, besides endogenous signals common in (1) to (3), is observed in a sample of (2) digested with restriction enzymes Hind III and EcoR I, thereby identifying that the DNA containing the EXT gene promoter is integrated into (2).

In the case where the thus-obtained transformant is assayed for the GUS activity using X-Gluc as the substrate, localization of the GUS activity in cells or tissues can be easily examined by utilizing the property of the product called as indigotin, an insoluble indigo-blue pigment. That is to say, young plants, obtained by sowing the sterilized seeds on the MSK plate (kanamycin is added at a final concentration of 50 mg/l to the MSO plate) followed by germination, are placed, as is, in water containing 2 mM DTT and, after deaeration under reduced pressure, are transferred, as is, into the GUS reaction solution [1 mM X-Gluc, 50 mM phosphate buffer solution (pH 7.0), and 20% methanol] to undergo the reaction at 37° C. for 0.5 to 4 hours.

After completion of the reaction, ethanol is added to stop the reaction and remove pigments such as chlorophyll and the plants were washed with ethanol two or three times, allowed to stand for 3 hours to overnight, and then transferred in a Petri dish filled with water. The plants are placed on a slide glass and, after addition of 1 to 2 drops of 70% hydrous glycerol for fitting followed by further addition of glycerol, pressed with a cover glass to allow to be observed under a microscope. When the above procedure is carried out on (1) the WS strain that does not undergo the transformation, (2) the transformant in which the chimeric gene is transferred, and (3) the transformant in which only the vector pBI121 is transferred, it can be observed that tissue portions which grow with elongation in (2) are stained blue, whereas tissues in (1) are not stained at all and the whole tissues in (3) are stained, albeit unevenly.

The procedure exemplified in the following can be applied to a procedure for obtaining a promoter that is hybridizable to the plant promoter of the present invention and also possesses the promoter activity in at least one of plants, plant cells, and transgenic plants regenerated from the plant cells.

First, a chromosomal DNA obtained from the objective gene source is transferred into a host by ligation to a plasmid or phage vector, according to a conventional method, to prepare a library. The library is cultivated on a plate and grown colonies or plaques are taken on a nitrocellulose or nylon membrane, on which the DNA is immobilized by denaturation. The membrane is warmed in a solution containing a probe that is labeled in advance with $^{32}$P etc. (the probe is exemplified by the nucleotide sequences as described in SEQ ID NO 1, 2, 3, 4, 5, 6, 7, and 8 in the Sequence Listing or some genes thereof) to hybridize the DNA on the membrane with the probe. For example, the DNA-immobilized membrane undergoes hybridization with the probe at 65° C. for 20 hours in a solution containing 6×SSC, 1% sodium lauryl sulfate, 100 µg/ml of a sermon sperm DNA, and 5×Denhardt's solution (containing bovine serum albumin, polyvinyl pyrrolidone, and ficoll, each at a 1% concentration). After the hybridization, nonspecific adsorption is washed away and a clone hybridized with the probe is identified by autoradiography or the like. This process is repeated until a single hybridized clone is obtained. The objective plant promoter is inserted into the thus-obtained clone.

The nucleotide sequence of the resulting gene is determined, for example, by the following way to confirm that this gene is the objective plant promoter.

In the case of nucleotide sequencing of the clone obtained by the hybridization, E. coli, when used as the recombinant, is cultivated in test tubes or the like and a plasmid is extracted by a conventional method. After the cleavage with restriction enzymes, the inserted fragment is taken out and undergoes subcloning to the M13 phage vector, followed by the nucleotide sequencing by the dideoxy method. In the case where the recombinant is a phage, the nucleotide sequencing can be carried out by basically the same steps. Basic experimental procedures for such cultivation to nucleotide sequencing are described in "Molecular Cloning, A Laboratory Manual" (T. Maniatis et al., published by Cold Spring Harbor Laboratory Press in 1989) and so on.

In order to confirm that the obtained gene is the objective plant promoter, the determined nucleotide sequence is compared with that of the plant promoter of the present invention and with the nucleotide sequences as described in SEQ ID NO 1, 2, 3, 4, 5, 6, 7, and 8 in the Sequence Listing to deduce the structure of the gene.

When the obtained gene does not contain the entire plant promoter region, a synthetic DNA primer is prepared on the basis of the obtained gene and then the nucleotide sequence of the entire plant promoter region that hybridizes the promoter of the present invention can be determined by amplification of a deficient region by PCR and further screening of the DNA library using the obtained gene fragment as a probe.

Moreover, on the basis of the nucleotide sequence of the plant promoter of the present invention, modification of a portion of the nucleotide sequence by at least one of substitution, insertion, and deletion that are induced by site-directed mutagenesis of the gene containing the nucleotide sequence enables to change the function of the plant promoter of the present invention, thereby obtaining plant promoters similar to the plant promoters of the present invention. Examples of known methods for such site-directed mutagenesis include the gapped duplex method [Methods in Enzymology, 154, 350–367 (1987)], the uracil-containing DNA method [Methods in Enzymology, 154, 367–382 (1987)], the nitrite method [Proceedings of the National Academy of Sciences of the USA, 79, 7258–7262 (1982)], and further the cassette mutagenesis method [Gene, 34, 315–323 (1985)].

Furthermore, on the basis of the nucleotide sequence of the plant promoter of the present invention, a chimeric promoter [Proceedings of the National Academy of Sciences of the USA, 88, 7266–7270 (1991)] is constructed by ligation or substitution of a gene containing the nucleotide sequence or a portion of the gene with a gene of known plant promoters or the like, or a portion of this gene, thereby obtaining a plant promoter possessing the promoter activity at the site and stage required for the reconstitution of plant cell wall xyloglucan, like the promoters of the present invention.

Ligation of the thus-obtained plant promoter at a downstream therefrom with a useful gene in the operable state followed by assay of the promoter activity by the same method as that for the promoters of the present invention enables to confirm whether the plant promoter functions in at least one of plants, plant cells, and transgenic plants regenerated from the plant cells. Also, the expression site specificity controlled by the plant promoter can be identified.

In the case where the plant promoter to be obtained in the present invention is introduced into any of plants, plant cells, and transgenic plants regenerated from the plant cells, the promoter can be introduced in the form of a vector that is retained extrachromosomally or of a vector that is integrated intrachromosomally. Such extrachromosomally retained vectors and intrachromosomally integrated vectors are known in the art and introduction into plants and transgenic plants regenerated from plant cells can be carried out by, for example, the microinjection method, the polyethylene glycol method, the particle gun method, the protoplast fusion method with a vector-containing small cells, cells, lysosome, etc., the electroporation method, and so on. Furthermore, the vector can be converted into a chimeric gene in which a gene encoding several amino acids at the N-terminus of an enzyme possessing a function to reconstitute plant cell wall xyloglucan at a downstream from the plant promoter is ligated at an upstream from the useful gene in an operable state.

Using promoters of the EXT gene or EXT family genes to be obtained in the present invention or polynucleotides having a sequence or its partial sequence that are hybridizable to the promoters, ligation of a useful gene at its downstream in an operable state, followed by introduction into plants and plant cells, enables to induce the gene expression in a specific manner at the site and stage required for the reconstitution of plant cell wall xyloglucan, like the promoters of the present invention, thereby controlling the plant morphology. For example, the control can be made by ligating a gene encoding an antisense RNA, a decoy etc. or a ribozyme so as to function at a downstream from the promoter of the present invention, followed by introduction into plants, plant cells, and transgenic plants regenerated from the plant cells. Dwarf plants can be produced by controlling the plant morphology, whereas male-sterile plants can be prepared by controlling elongation of the pollen tube. Furthermore, the quality of food or feed can be improved for plants of which the elongating/growing stems, the sites required for the reconstitution of plant cell wall xyloglucan, are utilized as foods. Further, induction of specific gene expression at the logarithmic growth phase or the stationary state of culture cells enables, for example, control of the cell proliferation and improvement in the productivity of useful secondary metabolites.

Moreover, according to the present invention, plant promoters having the promoter activity at the site and stage required for the reconstitution of plant cell wall xyloglucan can be cloned by utilizing the genes encoding enzymes having the function to carry out the reconstitution of plant cell wall xyloglucan and, particularly, genes encoding EXT or its functional equivalent.

Figure 1:
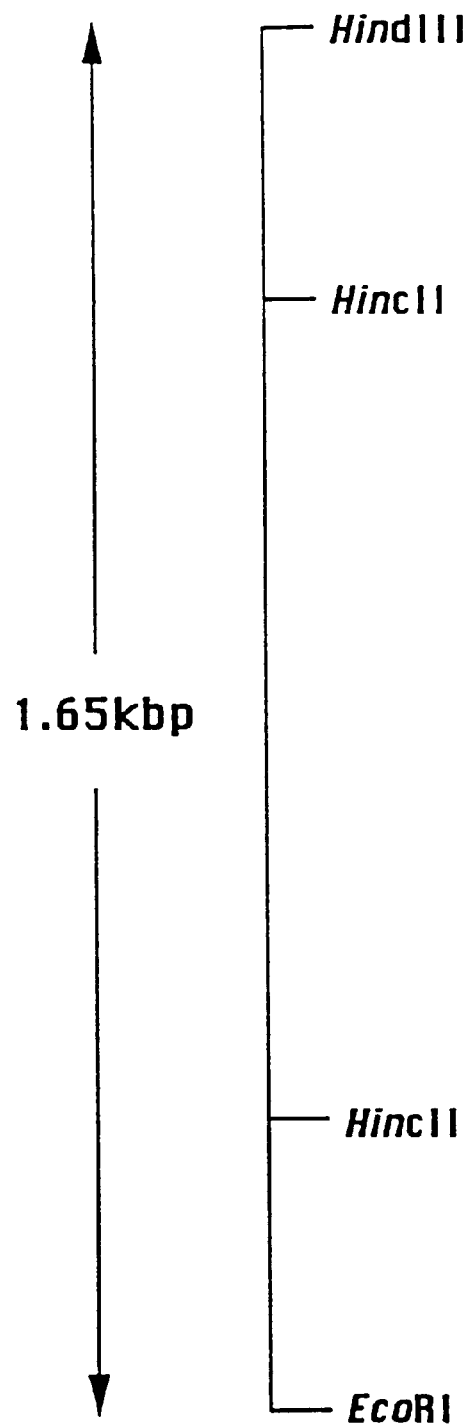
FIG. 1 is a restriction map of the fragment inserted in pVXP101.

The following examples further illustrate the present invention in more detail but are not construed to limit the scope of the present invention.

EXAMPLE 1

Isolation of Family Genes (Azuki Bean EXT 2 and Azuki Bean EXT 3) of Endo-xyloglucan Transferase (EXT)

(1) Poly(A)$^+$RNA

Seeds of *Vigna angularis* ohwi et Ohashi, cv. Takara (WATANABE SHUSHI Co., Ltd.) were germinated according to the method described in Physiologia Plantarum, 82, 490–497 (1991).

After one week from the germination, stems and leaves in the ground part were cut off to obtain about 2 g of plant tissues. They were immediately frozen in liquid nitrogen and grounded in a mortar in the presence of liquid nitrogen to prepare a powder, which was suspended in 20 ml of a denaturation solution [7 M guanidine thiocyanate, 25 mM sodium citrate (pH: 7.0), 0.1 M mercaptoethanol, and 2% sodium lauroylsarcosinate). The resulting suspension was crushed with Polytron, mixed with 10 ml of the denaturation solution and 30 ml of a phenol/chloroform solution [a 1:1 mixture of water saturated acidic phenol and chloroform/isoamyl alcohol (49:1)] with stirring thoroughly, and centrifuged to separate an aqueous layer, which was mixed with isopropyl alcohol, a 1/10 volume of 3 M sodium acetate, and a 1/300 volume of acetic acid and then centrifuged to obtain about 4 mg of RNA as a precipitate.

This precipitate was dissolved in 2 ml of an adsorption buffer solution [20 mM Tris-HCl (pH: 7.5), 2 mM EDTA, 1 M NaCl, and 0.5% SDS) and adsorbed on an oligo(dT)-cellulose Type-7 column (Pharmacia), which was eluted with an elution buffer solution [10 mM Tris-HCl (pH: 7.5) and 1 mM EDTA] to recover about 25 µg of poly(A)$^+$RNA.

(2) Construction and Screening of cDNA Library

A cDNA library was constructed from poly(A)$^+$RNA obtained in Example 1-(1) by using cDNA Synthesis Kit System-Plus (Amersham) according to the method described in Gene, 25, 263–269 (1983) using λgt10 (Stratagene) as a vector. The azuki bean EXT gene cDNA [EP-0562836 A1 (1993)] was labeled with [α-$^{32}$P]dCTP using Random Primer Labeling Kit (TAKARA SHUZO Co., Ltd.) to prepare a probe for hybridization. The specific activity of this probe was $7.5 \times 10^8$ cpm/µg. The plaque hybridization method using this probe was applied to the above-constructed cDNP library. That is to say, plaques were formed at $1 \times 10^4$ plaques per plate and transferred on a membrane. After denaturation, neutralization, and immobilization, the membrane was subjected to pre-hybridization in a prehybridization buffer solution (6×SSC, 0.1% SDS, 5× Denhardt's solution, and 10 µg/ml salmon-sperm DNA) at 50° C. for 2 hours. Then, the hybridization buffer solution was added to make the probe at $2 \times 10^5$ to $10^6$/ml and hybridization was carried out at 50° C. for 15 hours. After completion of the hybridization, the membrane was washed twice with a washing solution containing 6×SSC and 0.1% SDS at room temperature for 20 minutes. The membrane was exposed overnight at −80° C. in a cassette in which a sensitized X-ray film paper (Kodak) was placed to prepare an autoradiograph. As a result of search on $5 \times 10^4$ plaques, 96 positive plaques were obtained. Each of these plaques underwent a secondary screening and used in the following experiment.

(3) Classification of Plaques and Isolation of Azuki Bean EXT2 cDNA and Azuki Bean EXT3 cDNA, Family Genes of EXT Gene The plate lysate method (T. Maniatis et al., "Molecular Cloning, A laboratory Manual", Second Edition, Chapter 2, pp. 60–66, published by Cold Spring Harbox Laboratory Press in 1989) was applied to the above-obtained plaques to prepare a large quantity of phage particles, which were employed for dot hybridization using, as a probe, the azuki bean EXT gene cDNA used in Example 1-(2). After the hybridization steps carried out in the same manner as described above, filters were washed under gradiently intensified conditions with 6×SSC, 4×SSC, 2×SSC, and 0.1×SSC at 50° C. and then 0.1×SSC at 65° C. to allow classification on the basis of the signal intensities. As a result, the plaques were classified into 6 types of groups. Of these groups, two types of plaques showing signal intensities different from those of the azuki bean EXT gene were obtained from groups where the signals were detectable after washing with 0.1×SSC at 50° C. but were not detectable after washing with 0.1×SSC at 65° C. Phages were isolated from these plaques and the inserted DNAs were extracted. The lengths of the DNA fragments were identified by cleavage of said DNAs with restriction enzyme EcoR I followed by agarose gel electrophoresis. As the result, about 730 bp and about 430 bp were detected from one type of plaque and about 1090 bp from another type of plaque. Each of these DNA fragments were subjected to purification followed by subcloning at the EcoR I site of pUC18 (TAKARA SHUZO Co., Ltd.) and the resulting plasmids were named as pVX-44-1, pvX-44-2, and pVX-45-1, respectively. When these plasmids underwent nucleotide sequencing of the DNA fragments according to the aforementioned Sanger method [Science, 214, 1205–1210 (1981)] using BcaBEST™ Dideoxy Sequencing Kit (TAKARA SHUZO Co., Ltd.), a gene (azuki bean EXT2) having a high homology with the azuki bean EXT gene was cloned from pVX-44-1 and pVX-44-2, and further another type of gene (azuki bean EXT3) having a high homology with the azuki bean EXT gene was cloned from pVX-45-1. Partial nucleotide sequences thereof are shown in SEQ ID NO 11 and SEQ ID NO 12 in the Sequence Listing.

EXAMPLE 2

Isolation of Azuki Bean XRP1 cDNA, Family Gene of EXT Gene

A cDNA library was constructed from poly(A)$^+$RNA obtained in Example 1-(1) by using cDNA Synthesis Kit (TAKARA SHUZO Co., Ltd.) according to the method described in Gene, 25, 263–269 (1983) using λZAPII (Stratagene) as a vector. In order to prepare a probe, a mixed synthetic oligonucleotide (27 mer, SEQ ID NO 13) corresponding to the amino acid sequence (SEQ ID NO 28) of DEIDFEFLG, one of sequences conserved often for the proteins that act upon xyloglucans, was labeled with [γ-$^{32}$P] ATP using DNA 5'-Terminal-Labeling Kit MEGALABEL™ (TAKARA SHUZO Co., Ltd.). The specific activity of this probe was about 1×10$^8$ cpm/μg. The plaque hybridization method using this probe was carried out for the above-constructed cDNA library in the same manner as in Example 1, where the hybridization was carried out at 50° C. for 15 hours. Then, the membrane was washed twice with 2×SSC at 50° C. for 20 minutes and underwent the autoradiography. Plaques were formed on 10×14 cm plates at about twenty thousand plaques per a plate. As a result of search on about one hundred thousand plaques, no positive signals were detected. When a positive control was carried out at the same time by formation of plaques of phage particles integrated with the azuki bean EXT cDNA at about 50 plaques per a square plate, followed by hybridization under the same conditions, distinct positive signals corresponding each of plaques were detected.

In contrast, it was strange that no positive signals were detected, when the phage solution (containing about ten thousand plaques) of the cDNA library was mixed with the phage solution in the positive control so as to form about 50 plaques thereof per a square plate. Such an incidence has not occurred in the case of plaque hybridization using a cDNA fragment with a length of more than 100 bases and thus the problem apparently arises when an oligomer of an about 20 to 30 base length is utilized as a probe. It is conceivable that the formation of positive signals was blocked by a certain interaction with plaques originating from a large number of other coexisting phages, even in the presence of positive clones.

As a result of the formation of plaques at 500 to 1000 plaques per a plate not so densely to avoid the problem, followed by search on about 8×10$^3$ plaques, 8 positive plaques were obtained. Upon double infection with the M13 helper phage and with the host bacterium of the F' strain, λZAPII can undergo automatic subcloning in which a region cloned in the host is converted automatically into pBluescript SK (–) (Stratagene). Plasmids were prepared from the above-mentioned 8 plaques in this way and were subjected to cleavage with the restriction enzyme EcoR I (TAKARA SHUZO Co., Ltd.) followed by agarose gel electrophoresis to identify the lengths of DNA fragments. Of these fragments, one optionally selected DNA fragment of about 1.2 kbp was integrated into 3 types of plasmids which were named as pVM104, pVM106, and pVM109, respectively.

When these plasmids underwent nucleotide sequencing of the DNA fragments according to the aforementioned Sanger method using BcaBEST™ Dideoxy Sequencing Kit (TAKARA SHUZO Co., Ltd.), 2 types of genes having a high homology with the azuki bean EXT gene as well as with the BRUL gene [Plant Physiology, 104, 161–170 (1994)] and the meri-5 gene [the Plant Cell, 3, 359–370 (1991)] were cloned (pVM106 and pVM109 were the identical gene). A partial nucleotide sequence of pVM106 (azuki bean XRP1), one of these genes, is shown in SEQ ID NO 14 in the Sequence Listing.

EXAMPLE 3

Isolation of Azuki Bean XRP2 cDNA, Family Gene of EXT Gene, by PCR

About 10000 pfu (plaque forming unit) of a μphage solution (33 μl), prepared from the ground parts of azuki bean in the same manner as in Example 2, was subjected to twice extraction with the phenol/chloroform solution followed by ethanol precipitation to obtain a simply purified μphage DNA. With this total DNA utilized as a template, the PCR reaction using PCR Amplification Kit (TAKARA SHUZO Co., Ltd.) was carried out by using the mixed synthetic oligonucleotide (Sequence ID NO 13) as a sense primer and, as an antisense primer, an oligo(dT)18 primer in which dTTP was bonded with 18 bases. The reaction was carried out at 94° C. (1 minute), 55° C. (1 minute), and 72° C. (1 minute) with repeating the cycle 25 times and the resulting reaction solution was maintained at 72° C. for 7 minutes. Then, with 1 μl of this reaction solution utilized as a template, the second PCR was carried out by using the mixed synthetic oligonucleotide (SEQ ID NO 13) as a sense primer and the oligo(dT)18 primer as an antisense primer, with repeating the above-mentioned cycle 25 times. After completion of the reaction, the reaction mixture was analyzed by 3% agarose gel electrophoresis to confirm that DNA fragments of about 260 bp, 350 bp, 450 bp, 500 bp, 600 bp, 750 bp, 800 bp, and 1300 bp were amplified in a specific manner. These fragments were recovered and end-blunted by using DNA Blunting Kit (TAKARA SHUZO Co., Ltd.). In addition, the 5' terminus of the PCR product was phosphorylated by using MEGALABEL™ (TAKARA SHUZO Co., Ltd.) and the resulting product was subcloned at the Hinc II site of pUC119 (TAKARA SHUZO Co., Ltd.). When these plasmids underwent nucleotide sequencing of the DNA fragments according to the Sanger method using BcaBEST™ Dideoxy Sequencing Kit (TAKARA SHUZO Co., Ltd.), 2 types of genes having a homology with the azuki bean EXT gene were cloned. One of them was identical with pVM106 and pVM109 in Example 2. A partial nucleotide sequence of another gene (azuki bean XRP2) is shown in SEQ ID NO 15 in the Sequence Listing.

EXAMPLE 4

Isolation of Tobacco XRP1 cDNA, Family Gene of EXT Gene

A cDNA library (Stratagene) with λZAP as a vector was utilized and, in order to prepare a probe, a mixed synthetic oligonucleotide (27 mer, SEQ ID NO 13) corresponding to the amino acid sequence (SEQ ID NO 28) of DEIDFEFLG, conserved in the proteins that act upon xyloglucan, was labeled with [γ-$^{32}$P]ATP using DNA 5'-Terminal-Labeling Kit MEGALABEL™ (TAKARA SHUZO Co., Ltd.). The plaque hybridization using this probe was carried out for the above-mentioned cDNA library in the same manner as in Example 2. Then, as a result of search on about 3×10$^4$ plaques, 30 positive plaques were obtained.

Upon double infection with the M13 helper phage and with the host bacterium of the F' strain, λZAP (Stratagene) can undergo automatic subcloning in which a region cloned in the host is converted automatically into pBluescript SK (−) (Stratagene). Plasmids were prepared from the above-mentioned 30 plaques in this way and were subjected to cleavage with restriction enzyme EcoR I followed by agarose gel electrophoresis to identify the lengths of DNA fragments. Of these fragments, 2 types of plasmids containing DNA fragments of about 1.5 kpb and about 0.9 kpb were named as pTM3D and pTM11D, respectively.

When these plasmids underwent nucleotide sequencing of the DNA fragments according to the Sanger method using BcaBEST™ Dideoxy Sequencing Kit (TAKARA SHUZO Co., Ltd.), 2 types of genes having a homology with the azuki bean EXT gene as well as the above-mentioned BRU1 gene and meri-5 gene were cloned. A partial nucleotide sequence of pTM11D, one such type (tobacco XRP1), is shown in SEQ ID NO 16 in the Sequence Listing.

EXAMPLE 5

Isolation of Genome DNA Clones of EXT Gene Family Genes (1) Preparation of Genome DNA from Azuki Bean Leaves Seeds of *Vigna angularis* ohwi et Ohashi, cv. Takara (WATANABE SHUSHI Co., Ltd.) were germinated according to the method described in Physiologia Plantarum, 82, 490–497 (1991) to obtain about 10 g of leaves. These leaves (about 10 g) were pulverized in a mortar in the presence of liquid nitrogen to prepare a white powder. About 2.5 g of the leave powder was immediately placed in a 50 ml polystyrene tube and extracted with 10 ml of a urea-phenol DNA extraction buffer solution [0.05 M Tris-HCl (pH: 7.6), 0.02 M EDTA, 5% phenol, 8 M urea, 0.35 K NaCl, and 2% sodium lauroylsarcosinate] mixed with 25% SDS at 65° C. for 1 hour. The extract was mixed with a 2-fold volume of a phenol-chloroform-isoamyl alcohol (25:24:1) mixture, stirred gently for about 15 minutes, and then centrifuged at 2000 rpm for 15 minutes. After the centrifugation, the supernatant was transferred into a new tube, again mixed with a 2-fold volume of a phenol-chloroform-isoamyl alcohol (25:24:1) mixture, stirred gently for about 15 minutes, and then centrifuged at 2000 rpm for 15 minutes. The supernatant after this centrifugation was transferred into a new tube, mixed with a 2-fold volume of ethanol, and stirred gently. Then, the precipitated, white genome DNA was coiled out by using a Pasteur pipet and transferred into a new tube. To this tube was added 1.5 ml of a TE buffer solution (10 mM Tris-HCl (pH: 8.0) and 1 mM EDTA] and the resulting mixture was kept at 55° C. overnight to dissolve the DNA. Analysis of 1 μl of a sample, prepared by diluting of this DNA solution 10-fold, by 0.4% agarose gel electrophoresis revealed that the solution contained a high molecular DNA at a concentration of about 100 ng/μl. In other words, 150 μg of the genome DNA was obtained from about 2.5 g of the leaves.

(2) Construction of Genome DNA Library

Conditions were examined in order to subject the above-obtained genome DNA to partial digestion with restriction enzyme Sau3A I. That is to say, 10 U/μl of Sau3A I (TAKARA SHUZO Co., Ltd.) was diluted with a diluent buffer solution to adjust its concentration in a 50 μl reaction solution (1 μg DNA) to 1 to 0.035 U/μg DNA, which was reacted at 37° C. for 30 minutes and then mixed with 1 μl of 0.5 M EDTA to stop the reaction. After the reaction, a 20 μl sample was analyzed by 0.4% agarose gel electrophoresis to indicate that molecules of 15 to 20 kbp size were formed most abundantly under the condition with 0.1 U/μg DNA. The reaction was scaled up under this condition and to 10 μg of DNA, partially digested under this condition, were added 5 μl of a 10×fill-in buffer solution [0.5 M Tris-HCl (pH: 7.2), 0.1 M magnesium sulfate, 1 mM DTT, 500 μg/ml acetylated BSA, 10 mM dATP, and 10 mM dGTP) and 10 U of the Klenow fragment. After the total volume was made 50 μl with distilled water, the reaction was carried out at 37° C. for 30 minutes. After completion of the reaction, the reaction solution was mixed with 50 μl of a phenol-chloroform-isoamyl alcohol (25:24:1) mixture, stirred gently, and then centrifuged at 12000 rpm for 5 minutes. The supernatant was transferred into a new tube and precipitated with ethanol. The precipitate was dissolved in 20 μl of a TE buffer solution [10 mM Tris-HCl (pH: 8.0) and 1 mM EDTA]. Then, 0.5 μg and 1.5 μg each of the resulting partially filled-in, partially Sau3A I-digested genome DNA was ligated with 1.0 μg of λGEM11 Arm (Promega Biotech) using TaKaRa Ligation Kit Version 1 (TAKARA SHUZO Co., Ltd.). In other words, 0.5 μg and 1.5 μg each of the partially filled-in, partially Sau3A I-digested genome DNA was mixed with a solution containing 1.0 μg of λGEM11 Arm (Promega Biotech) and, after evaporation to dryness, the mixture was dissolved in 5 μl of a ligation buffer solution, mixed with 5 μl of Solution B in TaKaRa Ligation Kit Version 1 and then underwent ligation at 26° C. for 10 minutes. The ligated sample was subjected to twice phenol extraction followed by ethanol precipitation. Then, the total amount underwent packaging by using an in vitro packaging kit (Stratagene), followed by infection with *E. coli* LE392, the host bacterium, to obtain a genome DNA library of the azuki bean. The titer of this library was measured to be 2.1×10$^5$ pfu/ml.

(3) Screening of Library and Isolation of Gene

Utilizing this library, the azuki bean EXT gene cDNA [EP-0562836 A1 (1993)] of about 1.1 kbp was labeled with [α-$^{32}$P]dCTP using BcaBEST™ Labeling Kit (TAKARA SHUZO Co., Ltd.) to prepare a probe for plaque hybridization. In other words, 25 ng of the above-mentioned DNA fragment and 2 μl of a random primer were placed into a tube, diluted with distilled water to make 5 μl, and subjected to heating at 95° C. for 3 minutes followed by rapid cooling in ice. Thereto were added 2.5 μl of a buffer solution of a 10-fold concentration, 2.5 μl of a dNTP mixed solution, 5 μl of labeled dCTP, distilled water to make 24 μl, and 1 μl of BcaBEST™ DNA Polymerase (TAKARA SHUZO Co., Ltd.) and the resulting solution was incubated at 52° C. for 10 minutes. The enzyme was deactivated by heat denaturation with heating at 95° C. for 3 minutes followed by rapid cooling in ice. The total amount was used for the hybridization. The specific activity of this probe was 7.2×10$^8$ cpm/μg.

The plaque hybridization was carried out in the same manner as in Example 1, except that the pre-hybridization and hybridization were carried out at 65° C.

After the hybridization, the membrane was washed once with a washing solution containing 2×SSC and 0.1% SDS at room temperature for 20 minutes and further with a washing solution containing 0.1×SSC and 1% SDS at 50° C. for 20 minutes. Phages were inoculated on 10 square plates so as to form plaques at 1×10⁴ plaques per plate. As the result of screening on 1×10⁵ phages obtained from a total of 10 plates, 10 positive plaques were obtained. Next, each of these plaques was utilized for secondary screening. Phage DNA was extracted from each plaque obtained in the secondary screening by the plate lysate method. This phage DNA was subjected to digestion with restriction enzymes Sac I, EcoR I, Hind III, BamH I, and Pst I (all: TAKARA SHUZO Co., Ltd.), followed by Southern hybridization using the same probe mentioned above.

The Southern hybridization is carried out according to the method described in "Molecular Cloning, A laboratory Manual", Second Edition, Chapter 9, pp. 9.31–9.58 (T. Maniatis et al., Issued by Cold Spring Harbor Laboratory Press in 1989).

That is to say, each of the DNA samples was subjected to 1% agarose gel electrophoresis, followed by alkaline denaturation and Southern blotting on a nylon membrane (Hybond-N, Amersham) overnight. After DNA was immobilized by irradiation with a ultraviolet transilluminator (254 nm) for 5 minutes, the membrane was subjected to pre-hybridization in 5 ml of a pre-hybridization buffer solution (5×Denhardt's solution, 6×SSC, 0.1% SDS, and 10 µg/ml salmon sperm DNA) at 65° C. for 2 hours. Then, the probe was added and hybridization was carried out at 65° C. overnight. After the hybridization, the membrane was washed twice with a washing solution containing 2×SSC and 0.1% SDS at room temperature for 10 minutes and then washed twice with the same washing solution at 50° C. for 30 minutes. After being dried, the membrane was exposed overnight at −80° C. in a cassette in which an X-ray film (Kodak) was placed to prepare an autoradiograph.

From the pattern of the obtained autoradiograph, 10 phages were classified into 3 types. Of DNA fragments inserted into these 3 types of phage vectors, the DNA fragment, which was detected when the azuki bean EXT gene was used as the probe, underwent subcloning to the plasmid vector to analyze a partial nucleotide sequence. The result indicated that the DNA fragment inserted into phage vectors of all plaques contained a gene analogous to the EXT gene, namely a family gene. However, the EXT gene was not contained therein.

EXAMPLE 6

Cloning of DNA Fragment Containing "The Promoter Downstream" Region of Azuki Bean EXT Gene from Azuki Bean Partial Genome DNA Library The genome DNA extracted from azuki bean leaves in the same manner as in Example 5 was subjected to digestion with restriction enzymes of EcoR I and Hind III, double digestion with EcoR I-Hind III, and 0.7% agarose gel electrophoresis, followed by transfer to a nylon membrane and Southern hybridization using, as a probe, the azuki bean EXT gene cDNA prepared in the same manner as in Example 5-(3).

The Southern hybridization was carried out according to the method described in Example 5-(3), except that, after the hybridization, the membrane was washed thrice with a washing solution containing 2×SSC and 0.1% SDS at room temperature for 20 minutes, washed twice with the same washing solution at 50° C. for 20 minutes, and then washed twice with a washing solution containing 0.1×SSC and 0.1% SDS at 50° C. for 20 minutes.

The result revealed that about 3 bands were detected on each lane and the most intense band appeared for the EcoR I digest at about 8.5 kbp, for the Hind III at about 8.5 kbp, and for the EcoR I-Hind III double-digest at about 5.5 kbp. Then, 30 µg of DNA that was completely double-digested with EcoR I-Hind III was subjected to 0.7% agarose gel electrophoresis, recovery of a band around about 5.5 kbp from the agarose gel, ligation to the EcoR I-Hind III site of λEXlox (Novagene), and packaging by using in-vitro Packaging Kit (Stratagene), followed by infection with *E. coli* ER1647, the host bacterium, to obtain a partial azuki bean genome DNA library of a size centered with the about 5.5 kbp DNA fragment having the EcoR I-Hind III site at both termini. The titer of this library was 1.9×10⁶ pfu/ml.

Next, plaque hybridization using the azuki bean EXT gene cDNA as a probe was carried out in the same manner as in Example 5. Ten positive plaques were obtained from 1.3×10⁵ plaques. These plaques were suspended in a SM buffer solution and each plaque underwent secondary screening. In the second screening, the above-mentioned azuki bean EXT gene cDNA as well as an oligonucleotide VAN-U7 (Sequence ID NO 17), synthesized on the basis of a 5'-noncoded region having a low homology with an isozyme of the azuki bean EXT gene cDNA, were utilized as a probe, respectively. In the case where the azuki bean EXT gene cDNA was utilized as the probe, the plaque hybridization and washing were carried out in the same manner as described above. In the case where the synthetic oligonucleotide VAN-U7 was utilized, the hybridization probe was prepared by labeling with [γ-³²P]ATP using the 5'-Terminal-Labeling Kit MEGALABEL™ (TAKARA SHUZO Co., Ltd.) at the 5'-terminus. The specific activity of this probe was about 2×10⁸ cpm/µg. The plaque hybridization using this probe was carried out in the same manner as in Example 2, except that the pre-hybridization and the hybridization were carried out at 47° C. After the hybridization, the membrane was washed twice with a washing solution containing 6×SSC and 0.1% SDS at room temperature and then washed twice with the same washing solution at 47° C. for 20 minutes. The result revealed that, of 10 positive plaques, 4 plaques were DNA fragments containing the EXT gene cDNA. The phages inserted with these fragments were subjected to automatic subcloning by infection with *E. coli* BM25.8, a host bacterium having the PlCre gene, where a region subcloned automatically in the host was converted to a pUC-type plasmid. The thus-prepared plasmid was named as pVXG303.

The *E. coli* JM109 strain (TAKARA SHUZO Co., Ltd.) transformed with pVXG303 is denoted & imprinted as *Escherichia coli* JM109/pVX303 and has been deposited on Mar. 15, 1995 (the date of original deposit) in National Institute of Bioscience and Human-Technology, Agency of Industrial Science and Technology, Ministry of Industrial Trade and Industry (1-3, Higashi 1-Chome, Tsukuba-Shi, Ibaragi-ken, 305, Japan) as the accession No. FERN BP-5390, in accordance with the Budapest Treaty. This plasmid underwent nucleotide sequencing of the DNA fragments according to the Sanger method using BcaBEST™ Dideoxy Sequencing Kit (TAKARA SHUZO Co., Ltd.). Partial nucleotide sequences thereof are shown in SEQ ID NO 18 and SEQ ID NO 19 in the Sequence Listing. Comparison of these sequences with the sequence of the azuki bean EXT gene cDNA revealed that said fragment contained a promoter of the azuki bean EXT gene.

EXAMPLE 7

Cloning of DNA Fragment Containing Promoter Region of Azuki Bean EXT Gene by Inverse PCR (1) Examination of Self-Ligation Efficiency pVXG303 in Example 6 is a plasmid of about 9.5 kbp having an EcoR I/Hind III fragment originating from a genome DNA of 5.5 kbp containing a promoter region of the azuki bean EXT gene.

As a control for self-ligation and inverse PCR, this plasmid was digested with restriction enzyme Hind III and then self-ligated at DNA concentrations of 10 ng/µl, 3.3 ng/µl, 2 ng/µl, and 1 ng/µl, respectively. After the ligation, 5 µl each of the samples was transformed into E. coli JM109 and the self-ligation efficiency was obtained from the number of colonies formed. The result indicated that the self-ligation efficiency increased with diluting the DNA concentration. However, in the case where polymerase chain reactions (PCRs) with these ligation solutions used as templates were carried out by using a primer VAN-UH1 (SEQ ID NO 21) as a sense primer and a primer VAN-L (SEQ ID NO 22) as an antisense primer, an inhibition was induced when a larger volume of the ligation solution was added in the reaction system in order to increase the template amount and also the recovery decreased with diluting the DNA concentration when ethanol precipitation was carried out in order to decrease the template amount in the reaction system. These results revealed that the objective cyclic DNA could be obtained efficiently when the DNA concentration and the reaction volume in the ligation were adjusted at 3.3 ng/µl and 300 µl, respectively.

(2) Inverse PCR with Hind III Fragment of Azuki Bean DNA Used as Template

One µg of the genome DNA prepared from azuki bean leaves in the same manner as in Example 5 was completely digested with restriction enzyme Hind III, extracted once with the phenol/chloroform solution to deactivate the enzyme, and then underwent ethanol precipitation. The ethanol-precipitated DNA was mixed with 268 µl of distilled water, 30 µl of a 10× ligation buffer solution, and 2 µl of T4 DNA Ligase (TAKARA SHUZO Co., Ltd.) and then underwent self-ligation by reaction at 16° C. overnight. With 0.1 µg of the obtained cyclic genome DNA used as the template, PCR using TaKaRa LA PCR Kit (TAKARA SHUZO Co., Ltd.) was carried out by using primer VAN-UH1 (SEQ ID NO 21) as a sense primer and primer VAN-L (SEQ ID NO 22) as an antisense primer. The reaction was carried out by repeating a cycle of 94° C. (0.5 minute), 55° C. (1 minute), and 72° C. (2 minutes) 30 times. However, any amplification was not observed in this reaction. Then, with 1 µl of this reaction solution used as a template, PCRs were carried in the same manner with repeating the above-mentioned cycle 30 times by using:

1) primer VAN-UH2 (SEQ ID NO 23) as a sense primer and primer VAN-L6 (SEQ ID NO 24) as an antisense primer,
2) primer VAN-UH3 (SEQ ID NO 25) as a sense primer and primer VAN-L3 (SEQ ID NO 26) as an antisense primer,
3) primer VAN-UH2 (SEQ ID NO 23) as a sense primer and primer VAN-L3 (SEQ ID NO 26) as an antisense primer, and
4) primer VAN-UH3 (SEQ ID NO 25) as a sense primer and primer VAN-L6 (SEQ ID NO 24) as an antisense primer.

Analyses of the reaction solutions after the reactions by 1% agarose gel electrophoresis revealed that a DNA fragment of about 1.8 kbp was amplified specifically in the combination of 3). It was difficult in other combinations to identify the objective fragments owing to the amplification of many nonspecific DNA fragments.

The DNA fragment obtained in the primer combination of 3) was recovered from the gel and subjected to end-blunting using DNA Blunting Kit (TAKARA SHUZO Co., Ltd.), phosphorylation of the PCR product using the 5'-Terminal-Labeling Kit MEGALABEL™ (TAKARA SHUZO Co., Ltd.) at the 5'-terminus, and then subcloning at the Hinc II site of pUC119 (TAKARA SHUZO Co., Ltd.). Three plasmids were selected therefrom and underwent nucleotide sequencing of the DNA fragments according to the Sanger method using BcaBEST™ Dideoxy Sequencing Kit (TAKARA SHUZO Co., Ltd.). Since partial nucleotide sequencing indicated that the nucleotide sequences were identical for all plasmids, the total nucleotide sequence was determined by using one of these sequences.

Figure 2:
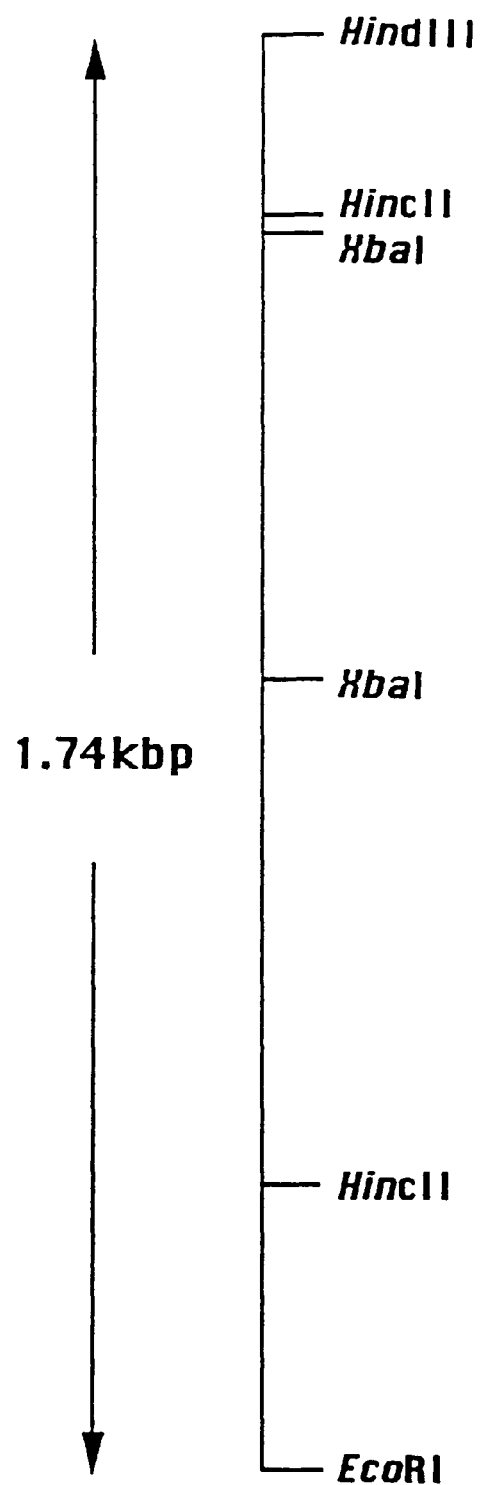
FIG. 2 is a restriction map of the fragment inserted in pVXP-H3.

A partial nucleotide sequence thereof is shown in SEQ ID NO 27 in the Sequence Listing. Also, the restriction map of said DNA fragment is shown in FIG. 2. The plasmid containing said DNA fragment is denoted as pVXP-H3, whereas E. coli JM109 strain transformed with said pVXP-H3 is denoted and indicated as Escherichia coli JM 109/pVXP-H3 and has been deposited on Feb. 17, 1995 (the date of original deposit) in National Institute of Bioscience and Human-Technology, Agency of Industrial Science and Technology, Ministry of Industrial Trade and Industry (1-3, Higashi 1-Chome, Tsukuba-Shi, Ibaragi-ken, 305, Japan) as the accession No. FERM BP-5388, in accordance with the Budapest Treaty.

EXAMPLE 8

Cloning of DNA Fragment Containing Promoter Upstream Region of Azuki Bean EXT Gene from Azuki Bean Genome DNA Library (1) Construction of Genomic DNA Library Conditions were examined in order to subject the genome DNA obtained in Example 5 to partial digestion with restriction enzyme Sau3A I. That is to say, 10 U/µl of Sau3A I (TAKARA SHUZO Co., Ltd.) was diluted with a diluent buffer solution to adjust its concentration in a 50 µl reaction solution (1 µg DNA) to 1 to 0.035 U/µg DNA, which was reacted at 37° C. for 30 minutes and then mixed with 1 µl of 0.5 M EDTA to stop the reaction. After the reaction, a 20 µl sample was analyzed by 0.4% agarose gel electrophoresis to indicate that molecules of 15 to 20 kbp size were formed most abundantly under the condition with 0.1 U/µg DNA. The reaction was scaled up under this condition.

Next, 160 µg of DNA, partially digested under this condition, was utilized for attempted fractionation of molecules of 15–20 kbp in sizes, by carrying out NaCl-density gradient centrifugation. That is to say, density gradients of 1.25 to 5 M NaCl were prepared into centrifuge tubes fitted to a HITACHI RPS40-T Rotor, 200 µl each of DNA (about 160 µg) was placed slowly, and ultracentrifugation using a HITACHI SCP70H ultracentrifuge was carried out at 35000 rpm for 3 hours. After the centrifugation, samples were divided in Eppendorf tubes with 250 µl each. Analysis of 20 µl aliquots taken from every 3 tubes by 0.4% agarose gel electrophoresis indicated that fractions Nos. 18 to 21 seemingly contained DNA molecules of appropriate sizes. Therefore, each of 0.3 µg, 0.6 µg, and 1.2 µg of the DNA from fraction No. 20 was mixed with a 1.0 µg solution of λGEM11 Arm (Promega Biotech) to make an 8 µl solution, which, after addition of 8 µl of Solution II and 16 µl of Solution I in TaKaRa Ligation Kit Version 2 (TAKARA SHUZO Co., Ltd.), underwent ligation at 26° C. for 10 minutes. Each of the samples after the ligation was subjected to twice extraction with phenol and ethanol precipitation. Then, the total amount underwent packaging by using an in vitro packaging kit (Stratagene), followed by infection with *E. coli* LE392, the host bacterium, to obtain an azuki bean genome DNA library. The titer of this library was $1.1 \times 10^5$ pfu/ml.

(2) Screening of Library

The genome DNA fragment obtained in Example 6 was labeled with [$\alpha$-$^{32}$P]dCTP using BcaBEST™ Labeling Kit (TAKARA SHUZO Co., Ltd.) to prepare a probe for hybridization. The plaque hybridization using this probe was carried out on the above-prepared genome DNA library in the same manner as in Example 5. After the hybridization, the membrane was washed thrice with a washing solution containing 2×SSC and 0.1% SDS at room temperature for 20 minutes and further washed once with a washing solution containing 1×SSC and 0.1% SDS at 50° C. for 20 minutes. Phages were inoculated on 20 square plates so as to form plaques at $1 \times 10^4$ plaques per plate. As a result of screening on $2 \times 10^5$ phages obtained from a total of 20 plates, 21 positive plaques were obtained. Next, each of these plaques underwent secondary screening in order to isolate its positive clone respectively.

The secondary screening was carried out by inoculation of a phage solution, which was taken from each of 21 positive plaques obtained in the primary screening, as thinly as possible so as to form about 300 plaques per a square plate, followed by plaque hybridization. In the second screening, the genomic DNA fragment obtained in Example 6 in the same manner as in the primary screening as well as an oligonucleotide VAN-U7 (SEQ ID NO 17), synthesized on the basis of a 5'-noncoded region having a low homology with family genes such as other isozymes (the azuki bean EXT2 and the azuki bean EXT3) in the azuki bean EXT gene cDNA sequence, respectively were utilized as a probe. In the case where the genomic DNA fragment was utilized as the probe, the plaque hybridization and washing were carried out in the same manner as in the first screening. In the case where the synthetic oligonucleotide VAN-U7 was utilized, the same procedure as in the case of Example 6 was applied.

Of 10 plaques showing positive signals obtained in the secondary screening, one plaque with an intense signal was selected for carrying out tertiary screening. However, this plaque with an intense signal was only one in about 1000 plaques even in the secondary screening. Furthermore, this only plaque was very small. For the purpose of purified proliferation of this plaque, the tertiary screening was carried out by inoculation on 6 circular plates (90 mm $\phi$) so as to form 100 to 200 plaques per a plate. They were utilized for the hybridization and washing in the same manner as in the secondary screening. As a result, an extremely small plaque of a needle-tip size was detected at a position that did not correspond to the plaque recognized as the signal at first glance but corresponded to the signal on a very careful observation of the plate. A phage DNA was extracted using this plaque by a careful application of the plate lysate method. DNA fragments inserted into a phage vector of said plaque were extracted and then a DNA fragment of about 11 kbp in length was obtained.

By carrying out double digestion of this DNA fragment with EcoR I-Hind III and Southern hybridization using, as a probe, the azuki bean EXT gene genome DNA fragment obtained in Example 6, a shorter DNA fragment containing a promoter region of this gene could be defined. Nucleotide sequencing using the plasmid inserted with this DNA fragment and comparison of said fragment with the sequence of the azuki bean EXT gene cDNA revealed whether this DNA fragment contained a promoter of the azuki bean EXT gene. FIG. 1 shows the restriction map of said fragment. Also, a partial nucleotide sequence of said fragment is shown in SEQ ID NO 20 in the Sequence Listing. The plasmid integrated with this fragment into the EcoR I and Hind III sites of pUC118 (TAKARA SHUZO Co., Ltd.) is denoted as pVXP11, whereas *E. coli* JM109 strain transformed with pVXP101 is denoted and indicated as *Escherichia coli* JM109/pVXP101 and has been deposited on Feb. 23, 1995 (the date of original deposit) in National Institute of Bioscience and Human-Technology, Agency of Industrial Science and Technology, Ministry of Industrial Trade and Industry (1-3, Higashi 1-Chome, Tsukuba-Shi, Ibaragi-ken, 305, Japan) as the accession No. FERM BP-5389, in accordance with the Budapest Treaty.

EXAMPLE 9

Northern Hybridization Using Azuki Bean Young Plant (1) Preparation of Total RNA Tissues taken from stems, buds, cotyledons, and leaves of 5 day-old and 40 day-old azuki bean plants after seeding were frozen in liquid nitrogen collectively and then kept at −80° C. until RNA extraction was operated. Total RNAs were extracted from each of these frozen tissues by the guanidine thiocyanate/phenol method. That is to say, 1 g of frozen cells was placed in a tube containing 2.5 ml of a guanidine thiocyanate solution [a 200-ml solution prepared by dissolving 100 g of guanidine thiocyanate and 1.47 g of sodium citrate dihydrate in water is kept at 4° C. and 7 $\mu$l of mercaptoethanol and 5 mg of sodium lauroylsarcosinate per 1 ml are added before use], crushed with a Polytron to effect extraction, mixed with 2.5 ml of a phenol-chloroform-isoamyl alcohol (25:24:1) mixture, stirred gently for 15 minutes, and then centrifuged at 3000 rpm for 10 minutes. Then, the separated aqueous layer was mixed with 2.5 ml of a phenol-chloroform-isoamyl alcohol (25:24:1) mixture with vigorous stirring and the resulting suspension was centrifuged to separate an aqueous layer. This procedure was repeated twice. Next, the resulting aqueous layer was mixed with 2.0 ml of a phenol-chloroform-isoamyl alcohol (25:24:1) mixture with vigorous stirring and the resulting suspension was centrifuged to separate an aqueous layer, which was mixed with 3 M sodium acetate and ethanol, and then centrifuged to obtain an RNA precipitate. This precipitate was completely dissolved in 2 ml of a Tris-SDS solution [50 mM Tris-HCl (pH: 9.0) and 1% SDS] and placed in a tube containing 2 ml of water-saturated phenol, which was shaken well. The resulting suspension was centrifuged to separate an aqueous layer, to which 2 ml of water-saturated phenol and 2 ml of a chloroform-isoamyl alcohol (49:1) mixture were successively added with vigorous stirring and the resulting suspension was centrifuged to separate an aqueous layer. Next, the resulting aqueous layer was mixed with 2 ml of a chloroform-isoamyl alcohol (49:1) mixture with vigorous stirring and the resulting suspension was centrifuged to separate an aqueous layer, which was mixed with 3 M sodium acetate and ethanol, and then centrifuged to obtain an RNA precipitate. This precipitate was completely dissolved in 0.5 ml of sterilized water and the concentration was adjusted to 1 mg/ml by measuring the absorbance. The resulting solution was mixed with a ¼ volume of 10 M lithium chloride with stirring, allowed to stand at 4° C. for 2 hours, and then centrifuged to obtain a precipitate. This precipitate was completely dissolved in 1 ml of sterilized water, mixed with 3 M sodium acetate and ethanol, and then centrifuged to obtain about 0.6 mg of an RNA precipitate.

(2) Northern Hybridization

A fragment of the azuki bean EXT gene cDNA [EP-0562836 A1 (1993)] was labeled with [α-$^{32}$P]dCTP using BcaBEST™ Labeling Kit (TAKARA SHUZO Co., Ltd.) to prepare a probe for northern hybridization.

The northern hybridization was carried out in the following way according to the method described in "Molecular Cloning, A laboratory Manual", Second Edition, Chapter 7, pp. 7.39–7.52 (T. Maniatis et al., published by Cold Spring Harbor Laboratory Press in 1989). That is to say, the extracted total RNA was subjected to electrophoresis with formaldehyde-running agarose gel (1%), followed by neutralization in an ammonium acetate solution and northern blotting on a nylon membrane (Hybond-N) overnight. After RNA was fixed by irradiation with a ultraviolet transilluminator (254 nm) for 5 minutes, the membrane was subjected to pre-hybridization in 20 ml of a pre-hybridization buffer solution (50% formaldehyde, 0.65 M NaCl, 0.1 M Na-PIPES (pH: 6.8), 5×Denhardt's solution, 0.1% SDS, 5 mM EDTA, and 100 μg/ml salmon-sperm DNA] at 42° C. for 3 hours. Then, the $^{32}$P-labeled probe prepared by the above-mentioned method was added to 20 ml of a pre-hybridization buffer solution [50% formaldehyde, 0.65 M NaCl, 0.1 M Na-PIPES (pH: 6.8), 5×Denhardt's solution, 0.1% SDS, 5 mM EDTA, and 10% dextran sulfate]. To this probe solution was added the membrane obtained by the pre-hybridization and hybridization was carried out at 42° C. overnight.

After the hybridization, the membrane was washed thrice with a washing solution containing 2×SSC and 0.1% SDS at 50° C. for 20 minutes. After being dried, the membrane was exposed overnight at −80° C. in a cassette in which an X-ray film (Kodak) was placed to prepare an autoradiograph.

The result revealed that the EXT gene expression was observed specifically in stems and the gene was expressed particularly in a part that was grown with elongation.

EXAMPLE 10

Northern Hybridization Using Tobacco Cultured Cells
(1) Preparation of Total RNA Tobacco BY2 cultured cells, which were cultivated for 1, 4, 6, 8, and 10 days, respectively were collected on a Buchner filter funnel by suction filtration. At this time, the suction was applied for additional 10 to 30 seconds after the culture medium was filtered out on the funnel, so as to remove the liquid culture medium completely. After the culture medium was drained off, about 1 g of cells was quickly recovered by weighing, immediately frozen in liquid nitrogen, and then kept at −80° C. until RNA extraction was operated. The frozen cells were placed in a tube containing 2 ml of an extraction solution [200 mM Tris-HCl (pH: 9.0), 100 mM NaCl, 10 mM EDTA, 0.5% SDS, and 14 mM 2-mercaptoethanol] and 2 ml of water-saturated phenol, crushed with a Polytron for 5 minutes to effect the extraction, mixed with 2 ml of a chloroform-isoamyl alcohol (49:1) mixture, and vigorously stirred further with a Polytron. The resulting suspension was centrifuged to separate an aqueous layer. Next, the resulting aqueous layer was successively mixed with 2 ml of water-saturated phenol and 2 ml of a chloroform-isoamyl alcohol (49:1) mixture with vigorous stirring and the resulting suspension was centrifuged to separate an aqueous layer. This procedure was repeated twice. The resulting aqueous layer was mixed with 2 ml of a chloroform-isoamyl alcohol (49:1) mixture with vigorous stirring and the resulting suspension was centrifuged to separate an aqueous layer, which was mixed with 3 M sodium acetate and ethanol, and then centrifuged to obtain about 0.7 mg of an RNA precipitate.

(2) Northern Hybridization

The tobacco EXT gene cDNA (JP 7-79778 A) and a cDNA fragment (SEQ ID NO 16) of the family gene tobacco XRP1 described in Example 4, respectively were labeled with [α-$^{32}$P]dCTP using BcaBEST™ Labeling Kit (TAKARA SHUZO Co., Ltd.) to prepare a probe for northern hybridization.

Figure 3:
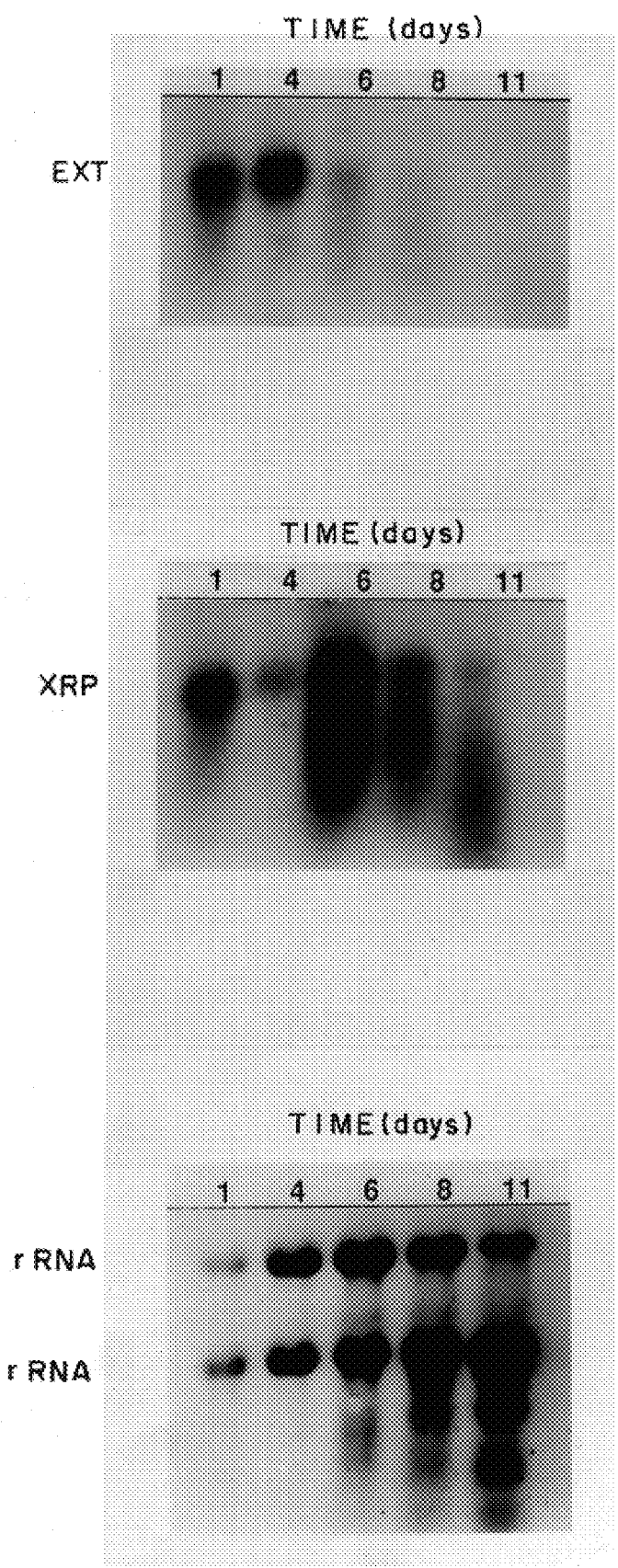
FIG. 3 is a photograph illustrating a migration pattern of northern hybridization of the culture cells in Example 10.

The northern hybridization was carried out in the same way as the method described in Example 9-(2). The results are shown in FIG. 3. That is to say, FIG. 3 illustrates the expressions of EXT and XRP, wherein the expression of a tobacco EXT mRNA was shown in the upper row, the expression of a tobacco XRP mRNA was shown in the middle row, and the rRNA amounts were shown in the lower row.

As can be seen from FIG. 3, it was revealed that the expression of the tobacco EXT gene was observed on the first day of the cultivation, reaching to a peak on the 4th day. Conversely, the tobacco XRP1 gene, a family gene of the EXT gene shown in Example 4, was expressed intensely on the first day of the cultivation and after the 6th day.

At the same time, the growth curve for the tobacco BY2 culture cells was also drawn by measuring the number of cells and the packed cell volume (PCV). The cell number was obtained by treatment of the tobacco BY2 culture cells with an enzyme solution (pH: 5.5) containing 1% cellulase-ONOZUKA (Yakult Honsha Co., Ltd.), 0.1% pectolyase Y23 (SEISHIN Corporation), and 0.4 M mannitol at 30° C. for 2 hours to be converted into cell wall-free protoplasts, followed by counting the number of the protoplasts with a blood counter. Furthermore, PCV was obtained by centrifugation of a culture suspension (10 ml) of the tobacco BY2 culture cells, taken in a 15 ml, graduated centrifuge tube, at 2000 rpm for 5 minutes by using a swing rotor, followed by measurement of the volume of cell pellets. Hereupon, a mean value (n=5) was plotted on the graph shown in FIG. 4. That is to say, FIG. 4 illustrates the growth in the tobacco BY2 cell culture, wherein the vertical axes represent PCV (%) and the cell number, and the horizontal axis represents the time (day).

Figure 4:
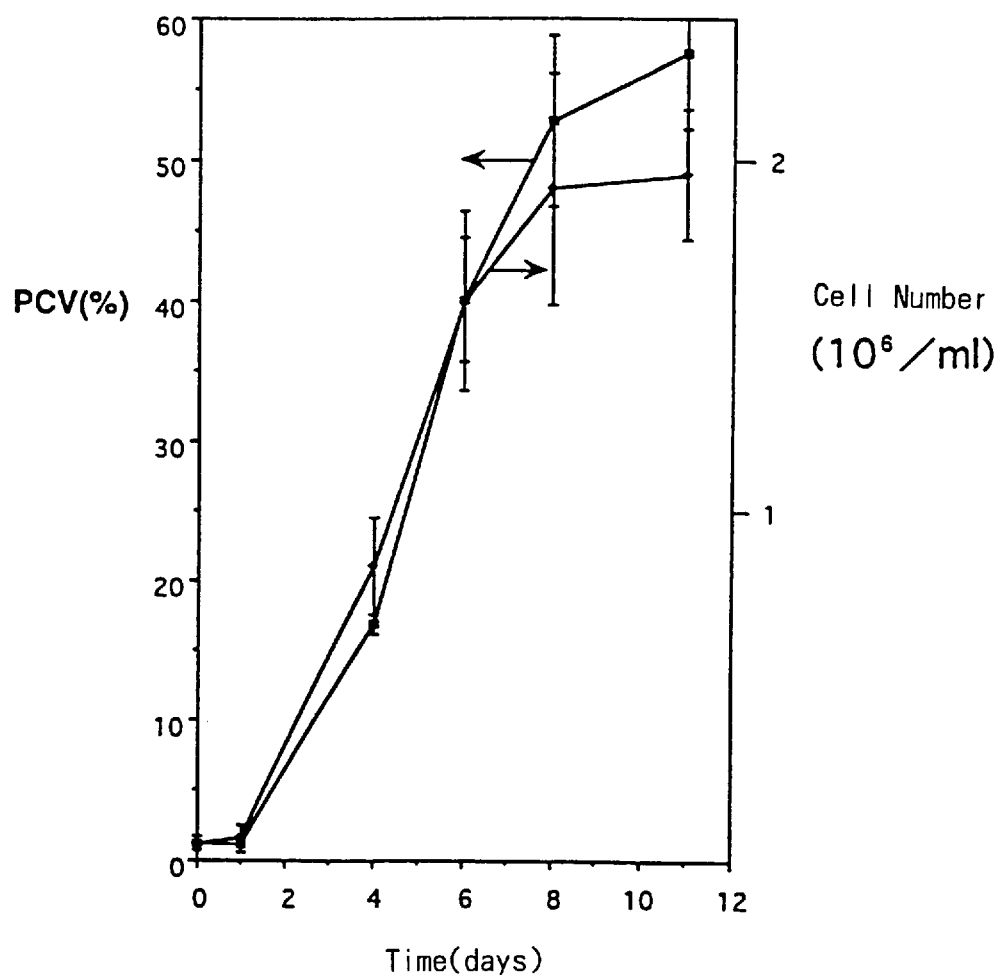
FIG. 4 is a graph illustrating the growth of the culture cells in Example 10.

The results illustrated in FIGS. 3 and 4 indicated that the tobacco EXT gene was expressed in any time and the expression was intense particularly in an early period of the logarithmic growth phase.

It was also indicated that the tobacco XRP1 gene, a family gene of the EXT gene shown in Example 4, was expressed intensely in the induction phase and the stationary phase.

EXAMPLE 11

Transient Assay Using Tobacco Culture Cells
(1) Construction of Plasmid for Transfer Using pBI121 (Clontech) having the cauliflower mosaic virus 35S promoter, the *E. coli*-origin GUS gene, and a transcription termination sequence cassette originating from nopaline synthetase, the EcoR site of this plasmid was first removed by subjecting said plasmid to end-blunting by using DNA Blunting Kit (TAKARA SHUZO Co., Ltd.) after complete digestion with restriction enzyme EcoR I and transformation into *E. coli* JM 109 strain after self-ligation. The obtained plasmid was named as pBI221EL and *E. coli* JM 109 strain transformed with pBI221EL was named as *Escherichia. coli* JM 109/pBI221EL. In order to remove the cauliflower mosaic virus 35S promoter region in the plasmid, this plasmid was subjected to digestion with restriction enzymes Hind III and Xba I and then purification of the objective fragment other than the 35S promoter region by agarose gel electrophoresis followed by cutting-off.

Next, with pVXG303 prepared in Example 6 used as the template, PCR was carried out by using primer VAN-UHE (SEQ ID NO 29) as a sense primer and primer VAN-LX (SEQ ID NO 30) as an antisense primer. The reaction was carried out by repeating a cycle of 94° C. (1 minute), 55° C. (2 minutes), and 72° C. (3 minutes) 10 times. The resulting fragment was subjected to recovery by separation with 2.5% agarose gel electrophoresis, ligation into the Hind III and Xba I sites of the above-mentioned pB1221EL, and transformation into E. coli JM 109 strain. This plasmid was named as pEXTΔEGUS and E. coli JM 109 strain transformed with pEXTΔEGUS was named as *Escherichia. coli* JM 109/pEXTΔEGUS.

Next, pEXTΔEGUS was subjected to end-blunting by using DNA Blunting Kit (TAKARA SHUZO Co., Ltd.) after complete digestion with restriction enzyme Hind III. The resulting DNA fragment was subjected to complete digestion with restriction enzyme EcoR I, terminal dephosphorylation by BAP treatment, and purification by agarose gel electrophoresis.

On the other hand, pVXP-H3 prepared in Example 7 was subjected to end-blunting after complete digestion with restriction enzyme Xba I (TAKARA SHUZO Co., Ltd.), followed by complete digestion with restriction enzyme EcoR I.

An about 960-bp DNA fragment containing a promoter region of the Xba I site to the EcoR I site of the azuki bean EXT gene was subjected to purification by agarose gel electrophoresis, ligation with the above-mentioned pEXTΔEGUS DNA fragment, and transformation into *E. coli* JM 109 strain. This plasmid was named as pEXTΔXGUS and E. coli JM 109 strain transformed with pEXTΔXGUS was named as *Escherichia. coli* JM 109/pEXTΔXGUS.

PEXTΔEGUS was subjected to complete digestion with restriction enzymes Hind III and EcoR I, ligation with a DNA fragment containing a promoter obtained by complete digestion of pVXP-H3, prepared in Example 7, with restriction enzymes Hind III and EcoR I, and then transformation into *E. coli* JM 109 strain. This plasmid was named as pEXTGUS and E. coli JM 109 strain transformed with pEXTGUS was named as *Escherichia. coli* JM 109/pEXTGUS.

(2) Gene Transfer by Electroporation

The electroporation method was applied to the transfer into tobacco BY2 culture cells by each of pEXTΔEGUS, pEXTΔXGUS, and pEXTGUS, prepared as described above, as well as by each of promoter-free pBI101 (Clontech; denoted as pGUS in FIG. 5) having only the GUS gene cassette and pBI221 (Clontech) having the cauliflower mosaic virus 35S promoter and the GUS gene, used as controls.

First, the tobacco BY2 culture cells were treated with an enzyme solution (pH: 5.5) containing 1% cellulase-ONOZUKA (Yakult Honsha Co., Ltd.), 0.1% pectolyase Y23 (SEISHIN Corporation), and 0.4 M mannitol at 30° C. for 2 hours to be converted into cell-wall-free protoplasts. A suspension of the $2\times10^6$ protoplasts of the tobacco BY2 culture cells in an electroporation buffer solution (70 mM KCl, 5 mM MES, and 0.3 M mannitol, pH 5.8) was mixed with 3 pmol of each plasmid DNA and a 10%. PEG 6000/electroporation buffer solution with stirring. An electric pulse (300 V, 125 μF) using Gene Pulser II (Bio-Rad Laboratories) was applied to the resulting mixture to transfer the DNA into the plant cells.

The cells were incubated in the Linsmaier-Skoog culture medium [Physiologia Plantarum, 18, 100 (1965)] containing 0.2 mg/l 2,4-D as an auxin, 1% sucrose, and 0.4 M mannitol at 26° C. for 40 hours after the transfer. The cells were recovered by extraction and a mixture of the recovered cells in 200 μl of an extraction buffer solution [50 mM phosphate buffer (pH 7.0), 10 mM EDTA, 0.1% Triton X-100, 0.1% Sarkosyl, and 10 mM 2-mercaptoethanol] placed in an Eppendorf tube was subjected to ultra-sonication on ice for 30 seconds by using a ultrasonicator W-225 (Heatsystems-Ultrasonics) with setting the output control at 1.5 and the duty cycle at 50%. Then, a supernatant isolated by centrifugation was used for the assay of the GUS activity and the assay of the protein quantity.

(3) Measurement of Promoter Activity

The reaction was carried out by adding 45 μl of the extraction buffer solution and 25 μl of a 4 mM 4-MUG substrate to each 30 μl of the extract placed in a 96-well microtiter plate for fluorescence. After 5, 35, and 95 minutes, the reaction was terminated by addition of 50 μl of a reaction-termination solution (1 M $Na_2CO_3$). Then, the specific fluorescence emitted by 4-MU, the reaction, product, at an excitation wavelength of 365 nm and fluorescence wavelength of 455 nm, was measured with a fluorescence plate reader [Fluoroscan II (Labosystems)].

Moreover, the protein quantity was assayed by a procedure described as follows. Thus, 2, 5, 10, 15, 20, and 30 μl of a ⅕-diluted solution of the extract or an 800 μg/ml BSA standard solution (20 μl of the extract buffer solution is mixed with 80 μl of 1 mg/ml BSA) were placed in a 96-well microtiter plate and thereto were added respectively 158, 155, 150, 145, 140, and 130 μl of distilled water and 40 μl of the assay reagent in Bio-Rad Protein Assay Kit (Bio-Rad Laboratories). After being stirred slowly and then allowed to stand for 20 minutes at room temperature, the mixture was measured by a plate reader (wavelength: 590 nm) within 60 minutes to assay the amount of protein.

Figure 5:
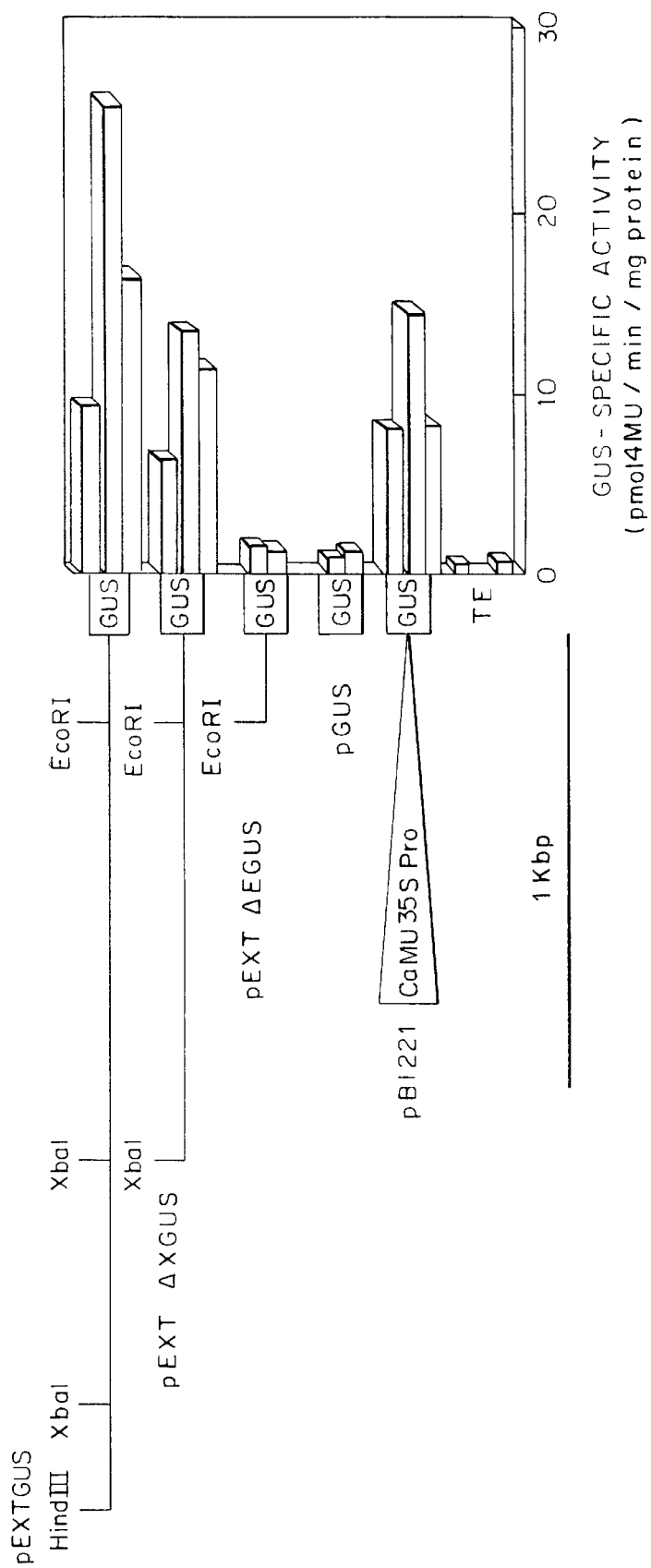
FIG. 5 is a graph illustrating the results of transient assay in Example 11.

The GUS activity was measured in the following way. At the same time when the above assays were carried out, the fluorescence intensities of the 4-MU standard solutions were measured and the results were plotted on a graph with the 4-MU quantity (pmol) at the x-axis and the fluorescence intensity at the y-axis. Then, the 4-MU quantity per one fluorescence unit was obtained from the slope and, further, the results on the samples were plotted on a graph with the time (minute) at the x-axis and the fluorescence intensity at the y-axis to obtain the increasing rate of the fluorescence intensity and then to obtain the decomposition rate of 4-MUG equal to the GUS activity. In addition, the GUS specific activity was obtained from the amount of protein. The results are shown in FIG. 5. In other words, FIG. 5 illustrates the measurement of the EXT promoter activity using the transformed tobacco BY2 culture cells, wherein the bar graph in the figure shows the GUS-specific activity (pmol 4MU/minute/mg protein) upon the transfer of each plasmid and the restriction map of the promoter region of each plasmid is illustrated thereunder.

As shown in FIG. 5, it could be verified that the DNA fragment containing the EXT gene promoter region exhibited an activity more intense than that of the cauliflower mosaic virus 35S promoter that had been said to be expressed intensely in the plants.

EXAMPLE 12

Figure 6:
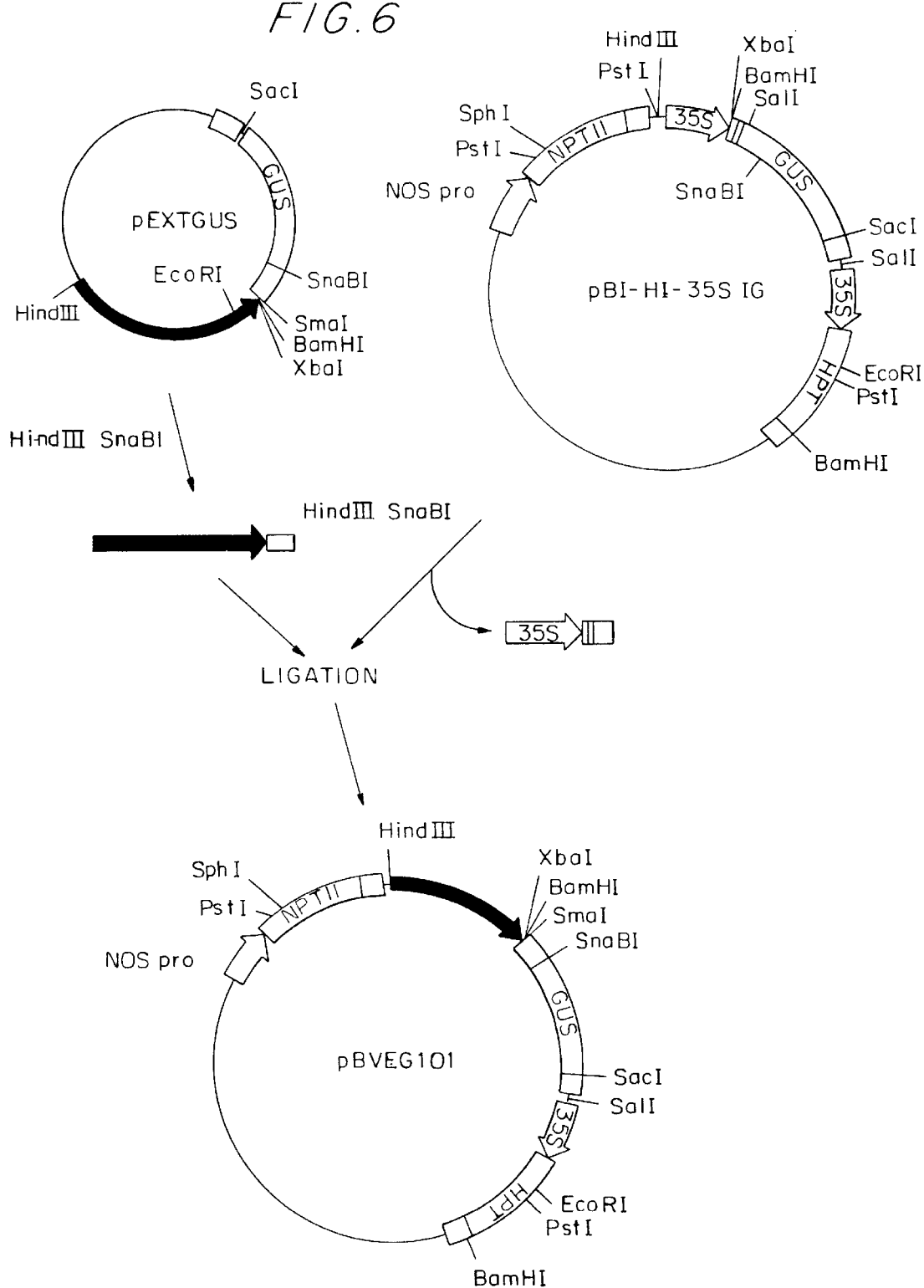
FIG. 6 is a construction diagram of pBVEG101.
Figure 7:
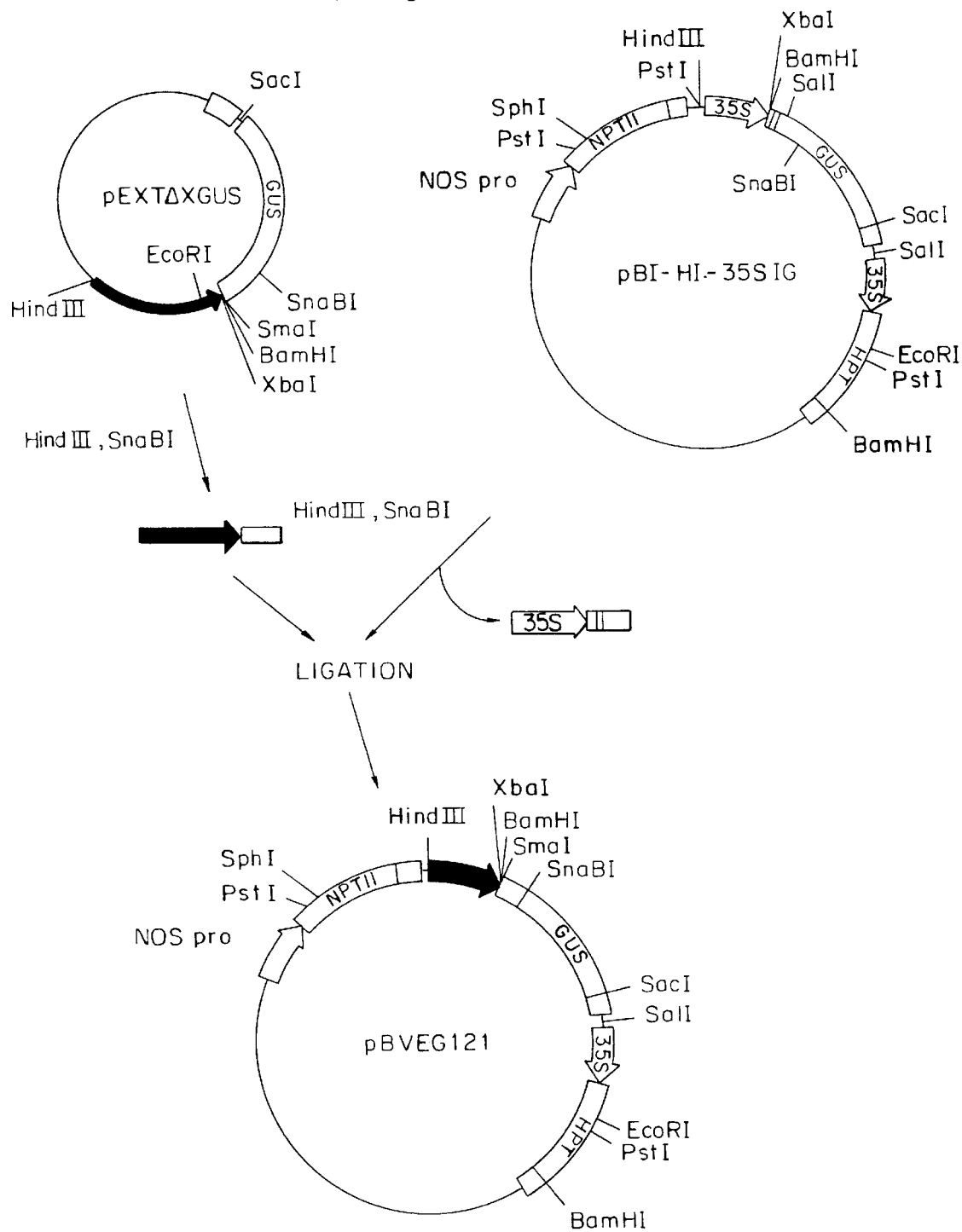
FIG. 7 is a construction diagram of pBVEG121.

Detection of Tissue Specificity Using Transformed Arabidopsis (1) Construction of Plasmids for Transfer In order to obtain plasmids for the transfer, as shown in FIGS. 6 and 7, a binary vector pBI-HI-35SIG [Plant and Cell Physiology, 31, 805–813 (1990)] having a transcription termination sequence cassette originating from nopaline synthetase and, as a marker gene, a gene resistant to hygromycin (HPT) and kanamycin (NPTII), and a GUS gene containing an *E. coli*-origin intron and the cauliflower mosaic virus 35S promoter, respectively, were digested with restriction enzymes Hind III and SnaB I (TAKARA SHUZO Co., Ltd.), and then purified by cutting out the objective fragment other than the 35S promoter region by agarose electrophoresis. Then, each of pEXTGUS prepared in Example 11 and above-mentioned PEXTΔXGUS were digested with restriction enzymes Hind III and SnaB I, and then purified by cutting out the fragment containing the azuki bean EXT promoter region by agarose gel electrophoresis. These fragments respectively were subjected to ligation at the Hind III and SnaB I sites of the above-mentioned pBI-HI-35SIG, and then transformation into *E. coli* JM 109 strain. These plasmids for the transfer were named as pBVEG101 and pBVEG121, respectively, and *E. coli* JM 109 strains transformed with these plasmids were named as *Escherichia. coli* JM 109/pBVEG101 and *Escherichia. coli* JM 109/pBVEG121, respectively.

Figure 8:
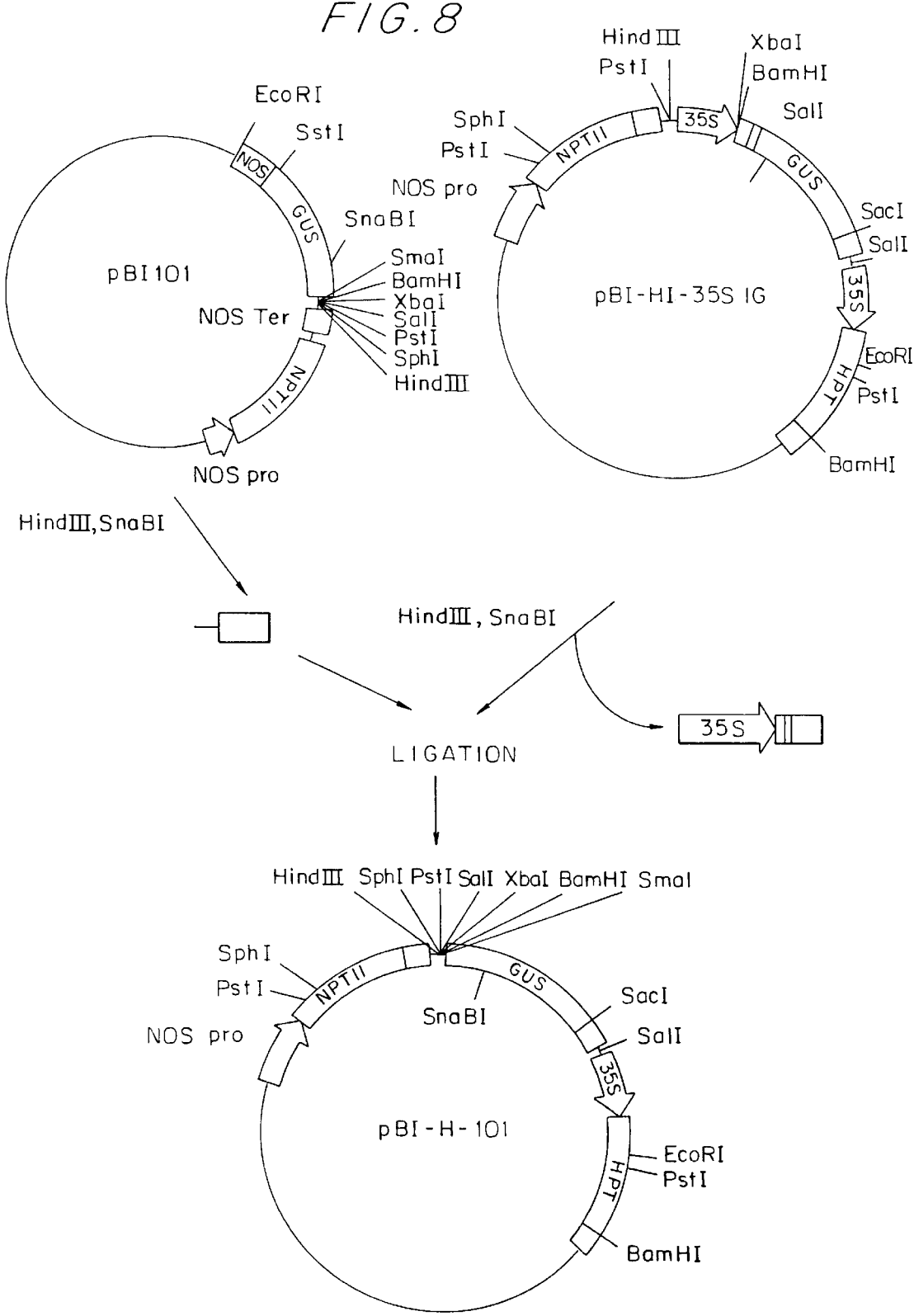
FIG. 8 is a construction diagram of pBI-H-101.
Figure 9:
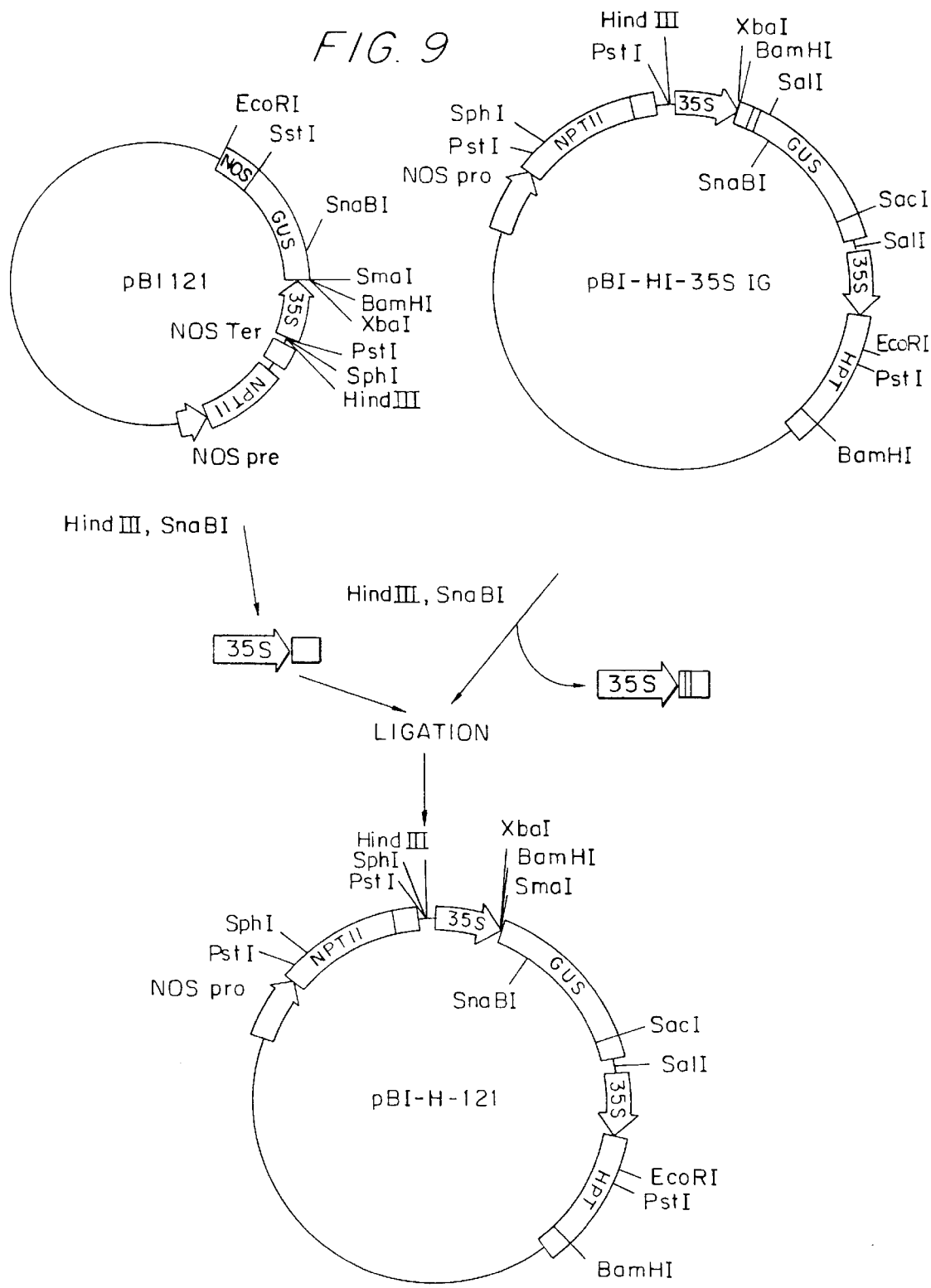
FIG. 9 is a construction diagram of pBI-H-121.

Furthermore, as shown in FIGS. 8 and 9, the Hind III and SnaB I fragments of promoter-free pBI101 (Clontech) having only the GUS gene cassette and pBI121 (Clontech) having the cauliflower mosaic virus 35S promoter were subcloned be the same procedure as described above at the Hind III and SnaB I sides of pBI-HI-35SIG to obtain the plasmids for control experiments. The thus-obtained plasmids were named as pBI-H-101 and pBI-H-121, respectively, and *E. coli* JM 109 strains transformed with these plasmids were named as Escherichia. coli JM 109/pBI-H-101 and *Escherichia. coli* JM 109/pBI-H-121, respectively.

(2) Transformation of Agrobacterium for Infection

Each of the above-mentioned plasmids was mixed with *Agrobacterium tumefaciens* EHA101 competent cells [SHOKUBUTU SAIBOU KOUGAKU (Plant Cell Technology) 4 (3), 193–203 (1992)], emitted with an electric pulse (2.5 kV, 25 μF, 200 Ω) using Gene Pulser II (Bio-Rad Laboratories), and cultivated at 30° C. for 2 days to transfer the plasmid into the Agrobacterium strain. The Agrobacterium strains transformed with these plasmids were named as *Agrobacterium tumefaciens* EHA101/pBVEG101, *Agrobacterium tumefaciens*, EHA101/pBVEG121, *Agrobacterium tumefaciens* EHA101/pBI-H-101, and *Agrobacterium tumefaciens* EHA101/pBI-H-121, respectively.

(3) Production of Transgenic Plants

WS seeds, an eco-type of *Arabidopsis thaliana*, (available from Notlingham Arabidopsis Stock Center: NASC) were disinfected on the surface with 20% hypochlorite, then sowed on an MSO plate (MURASHIGE-Skoog inorganic salt mixture (WAKO Pure Chemicals Industries, Ltd.), mixed with 2% sucrose, 3 mg/l thiamine hydrochloride, 5 mg/l nicotinic acid, and 0.5 mg/l pyridoxine hydrochloride, is adjusted to pH 6.3, mixed further with 0.2% gellan gum, autoclaved, and plated], underwent low-temperature treatment at 4° C. for 2 days, and then cultivated at 22° C. under continuous irradiation of a 3000-lux light. Transplantation on a new MSO plate was carried out at 1 week and 2 weeks after the sowing, respectively, and on 2 days after the transplantation at 2 weeks, 3 to 4 stumps were bundled and cut to prepare about 1 cm-long sections of the roots. The sections of the roots were placed side by side on a CIM plate (0.5 mg/l 2,4-dichlorophenoxyacetic acid and 0.05 mg/l kinetin are added to the MSO plate) and cultivated at 22° C. for 2 days under continuous irradiation of a 3000 lux light. Thereafter, the sections of the 2 day-cultivated roots were soaked for 30 seconds in a solution prepared by cultivation of each of the Agrobacterium strains obtained in (2) at 30° C. for 2 days followed by 5-fold dilution with the MS solution, soaked up to remove excess water, placed side by side on a new CIM plate, and then cultivated for 2 days. Two days later, the infected sections were transferred on a SIMC plate [to the MSO plate are added 5 mg/l N6-(2-isopentenyl) adenine, 0.15 mg/l indoleacetic acid, and 0.3 g/l carbenicillin], cultivated for 2 days, and then transplanted on a SIMCS plate (to the SIMC plate are added 50 mg/l of kanamycin and 20 mg/l of hygromycin). The plants were repeatedly transplanted on a new SIMCS plate once or twice per every week.

When regeneration of shoots were observed and the regenerated plants were equipped with complete rosette leaves of about 5 mm, the plant parts were cut off from the callus, and lightly inserted on a RIM plate (0.5 mg/l indoleactic acid is added to the MSO plate). Each of rooted plants underwent final transplanting on rock wool and cultivation in a liquid [Hyponecks (Hyponecks Japan) is diluted 1000-fold with water] to obtain T2 seeds.

(4) Detection of Tissue Specificity

The seeds obtained in (3) were sown on an MSKH plate (50 mg/l kanamycin and 20 mg/l hygromycin are added to the MSO plate) to select resistant stocks. The resistant stocks underwent final transplanting on rock wool and cultivation in a liquid [Hyponecks (Hyponecks Japan) is diluted 1000-fold with water].

A sample was collected by cutting off a portion of the ground part of plants that flowered and initiated silique formation, after about 30 days from the sowing. The cut plant sections were soaked in a fixed solution (20% paraformaldehyde, 0.1 M phosphate buffer, 1 mM EDTA, pH 7.0) at room temperature for 1 hour, washed twice with 0.1 M phosphate buffer, and then soaked in a substrate solution [2 mM X-Gluc, 50 mM phosphate buffer (pH 7.0), 0.5% Triton X-100, and 20% methanol]. After deaeration for 25 minutes to facilitate penetration of the substrate solution, the reaction was carried out at 37° C. for 1–3 days. After the reaction, the sample was washed with 70% ethanol, then observed by soaking into 40% glycerol, and reserved.

The results of the reaction indicated that a GUS-specific stain was not observed in wild-type plants as well as in those transferred with pBI-H-101 whereas the stain was detected in all tissues of plants transferred with pBI-H-121 (the cauliflower mosaic virus 35S promoter).

Figure 10:
FIG. 10 is a photograph illustrating the results of GUS-staining of the transgenic Arabidopsis plant in Example 12.

On the other hand, in plants transferred with pBVEG101 and pBVEG121 containing the azuki bean EXT gene promoter, the GUS stain was observed at an elongation part of stem, at the tips of leave and silique, and at the tip of pistil, indicating that these portions possessed a potent promoter activity. Of these results, the results on wild-type, pBI-H-121, and pBVEG101 were illustrated in FIG. 10.

EXAMPLE 13

Isolation of Azuki Bean EXT2 Gene Promoter by Inverse PCRs with Hind III, Nsp V, and Xba I Fragments of Azuki Bean Genome DNA Used as Templates One μg of the genome DNA prepared from azuki bean leaves in the same manner as in Example 5 placed in separate tubes was completely digested with each of restriction enzymes Hind III, Nsp V, and Xba I, respectively, extracted once with the phenol/chloroform solution to deactivate the enzyme, and then underwent ethanol precipitation. The ethanol-precipitated DNA was mixed with 268 μl of distilled water, 30 μl of a 10×ligation buffer solution, and 2 μl of T4 DNA Ligase (TAKARA SHUZO Co., Ltd.) and then underwent self-ligation by reaction at 16° C. overnight. With 0.1 μg of the obtained cyclic genome DNA used as the template, PCR using TAKARA LA PCR Kit (TAKARA SHUZO Co., Ltd.) was carried out by using primer IP44-3 (SEQ ID NO 31) as a sense primer and primer IP44-5 (SEQ ID NO 32) as an antisense primer. The reaction was carried out by repeating a cycle of 94° C. (1 minute), 98° C. (20 seconds), and 67° C. (10 minutes) 30 times, finally followed by 72° C. (10 minutes). After the reaction, 5 μl of the reaction solution underwent 1% agarose gel electrophoresis, indicating that an about 6.0 kbp band was observed only in the sample digested with restriction enzyme Hind III. For other samples, any amplification was not observed in this reaction. Then, 1 μl each of a 100-fold dilution of the sample digested with restriction enzyme Hind III and other reaction solution without dilution was used as a template for PCR that was carried out in the same manner by using primer IP44-2 (SEQ ID NO 33) as a sense primer and primer IP44-5 (SEQ ID NO 32) as an antisense primer. After the reaction, 5 μl of the reaction solution underwent analysis by 1% agarose gel electrophoresis, confirming that the about 6.0 kbp band was very intense and thus was amplified specifically in the sample digested with restriction enzyme Hind III. In the sample digested with restriction enzyme Nsp V, a large number of seemingly nonspecific DNA fragments were amplified, with an about 1.2-kbp band being likely a main band. In the sample digested with restriction enzyme Xba I, a large number of seemingly nonspecific DNA fragments were amplified and thus identification of the objective fragment was difficult. Then, from the sample digested with restriction enzyme Hind III, a DNA fragment obtained in the primary PCR was recovered from the gel and subjected to end-blunting using DNA Blunting Kit (TAKARA SHUZO Co., Ltd.), phosphorylation of the PCR product using the 5'-Terminal-Labeling Kit MEGALABEL™ (TAKARA SHUZO Co., Ltd.) at the 5'-terminus, and then transfer into the Hinc II site of pUC118. The resulting plasmid was transformed into E. coli JM109, but no colonies were obtained.

Then, it was planned that the restriction map of the about 6.0-kbp PCR fragment was prepared to define the promoter region and then several fragments were separated and subcloned.

First, an about 3.1 kbp band and an about 2.9 kbp band were separated by end-blunting of this PCR fragment followed by digestion with restriction enzyme Hind III. These DNA fragments were subjected together to ligation to the Hind III-Hinc II site of pUC118 and transformation into E. coli JM109, but only a plasmid containing a fragment inserted with the about 2.9 kbp DNA was obtained and that with the about 3.1 kbp DNA was not obtained. In addition, the results on PCR using primer IP44-2 (SEQ ID NO 33) and M13 Primer M4 (TAKARA SHUZO Co., Ltd.) as well as on PCR using primer IP44-6 (SEQ ID NO 34) and M13 Primer M4 (TAKARA SHUZO Co., Ltd.) revealed that amplification occurred only for primer IP44-6 (SEQ ID NO 34) and M13 Primer M4 and that the 2.9 kbp inserted fragment contained a 3'-downstream region of the azuki bean EXT2 gene whereas the 3.1 kbp fragment contained the promoter region.

Figure 11:
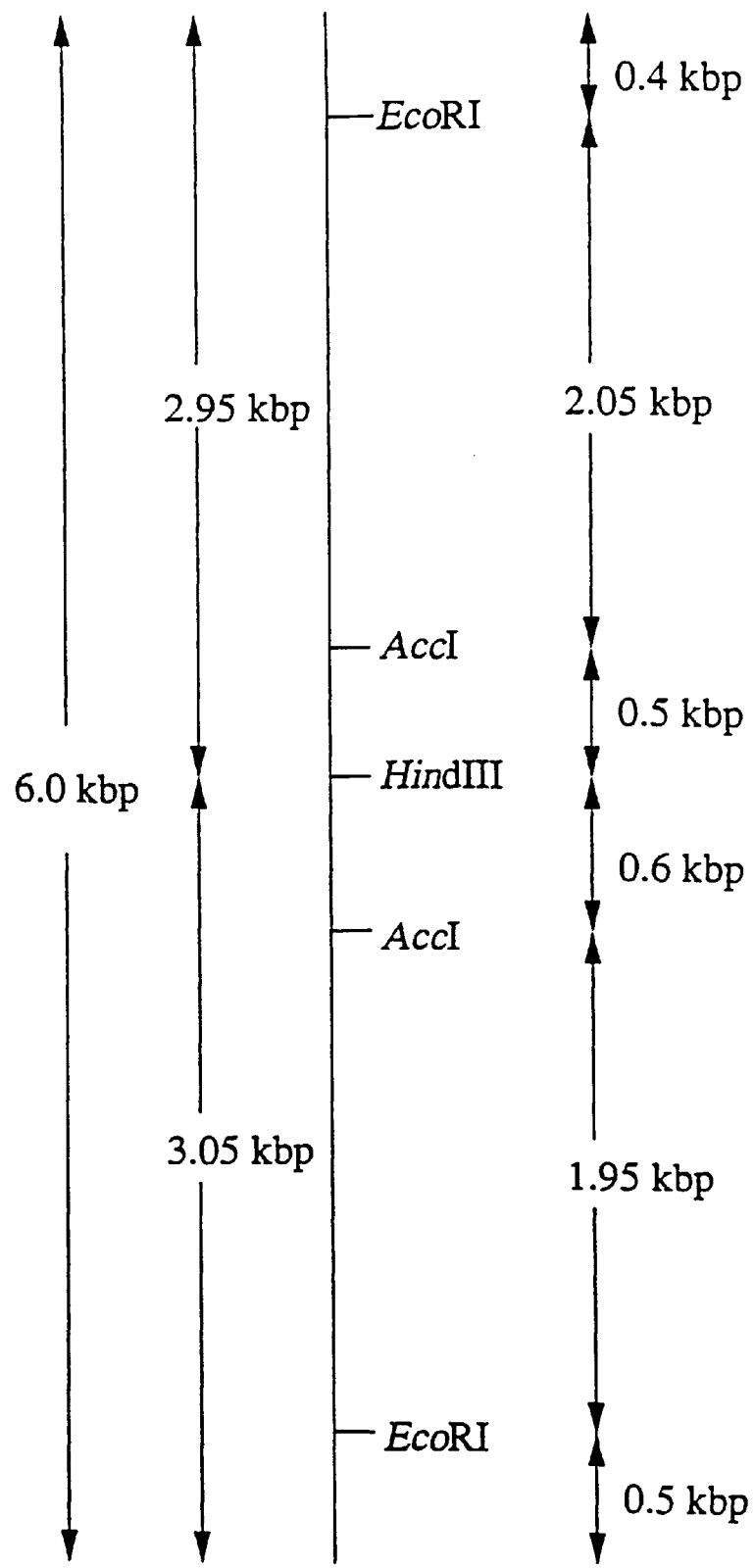
FIG. 11 is a restriction map of the DNA fragment of about 6.0-kbp amplified by PCR in Example 13.

FIG. 11 illustrates the restriction map of the about 6.0 kbp PCR fragment amplified with primers IP44-3 and IP44-5. In the figure, the upper part in the restriction map corresponds to the nucleotide sequence of primer IP44-5 and the lower part corresponds to the nucleotide sequence of primer IP44-3.

Next, because of the existence of two EcoR I sites on this about 6.0 kbp fragment, the PCR fragment was subjected to end-blunting followed by digestion with restriction enzymes Hind III and EcoR I to separate an about 0.4 kbp band, an about 0.5 kbp band, and an about 2.55 kbp band. Since the restriction map (FIG. 11) indicates the existence of promoter regions at about 0.5, kbp and at 2.55 kbp, each of these bands was subjected to ligation to the EcoR I-Hinc II site and the EcoR I-Hind III site of pUC118, followed by transformation into E. coli JM109.

Of colonies thus obtained, 16 colonies from the ligation at the EcoR I-Hinc II site were screened by PCR using primer IP44-2 (SEQ ID NO 33) and M13 Primer M4, (TAKARA SHUZO Co., Ltd.), revealing that 7 colonies were positive. Of these positive colonies, plasmids were extracted from 3 colonies and were named as pVX2P501, pVX2P503, and pVX2P505, respectively.

The nucleotide sequences of inserted fragments contained in pVX2P501, pVX2P503, and pVX2P505 were determined by subjecting each of pVX2P501, pVX2P503, and pVX2P505 to the sequence analysis of respective inserted fragment portions according to the Sanger method using M3 Primer M4 (TAKARA SHUZO Co., Ltd.) and M13 Primer RV (TAKARA SHUZO Co., Ltd.), followed by comprehensive interpretation of there results. Comparison of these sequences with the sequence (SEQ ID NO 11) of the original azuki bean EXT2 cDNA revealed that the overlapping portions were identical and also 3 types of clones had the completely identical sequence.

Forty six colonies from the ligation at the EcoR I-Hind III site were screened by PCR using primer IP44-2 (SEQ ID NO 33) and M13 Primer M4 (TAKARA SHUZO Co., Ltd.), revealing that 27 colonies contained an about 2.6 kbp inserted fragment.

Next, when this about 2.6 kbp fragment was digested with restriction enzyme Acc I (TAKARA SHUZO Co., Ltd.), an about 600 bp fragment appeared from 3 colonies and an about 500 bp fragment appeared from 12 colonies. Since the afore-mentioned restriction map (FIG. 11) indicates that an about 600 bp fragment appears from clones containing promoter regions, plasmids were extracted from 3 positive colonies and were named as pEXT2pro(F)f1, pEXT2pro(F)f2, and pEXT2pro(F)f3, respectively.

The partial sequence analysis of each of pEXT2pro(F)f1, pEXT2pro(F)f2, and pEXT2pro(F)f3 according to the Sanger method using M13 Primer M4 (TAKARA SHUZO Co., Ltd.) and M13 Primer RV (TAKARA SHUZO Co., Ltd.) revealed that 3 types of clones had the completely identical sequence. Next, in order to sequence the entire region of the about 2.6 kbp inserted fragment, a Pst I site adapter, which was prepared by using a synthetic oligomer E/Psite (1) (SEQ ID NO 35) and a synthetic oligomer E/Psite (2) (SEQ ID NO 36) was transferred into the EcoR I site of pEXT2pro(F)f3. This transfer allowed to transfer only the Pst I site at the side opposite to the EcoR I site of pEXT2pro (F)f3.

In addition, after complete digestion of this plasmid with restriction enzymes Pst I and EcoR I, Kilo-Sequence Deletion Kit (TAKARA SHUZO Co., Ltd.) was utilized to obtain clones that were deleted between the EcoR I site and the inserted fragment side.

The nucleotide sequences of inserted fragments contained in pEXT2pro(F)f3 were determined by subjecting some selected, deleted clones of appropriate lengths to the sequence analysis of respective inserted fragment portions according to the Sanger method using M13 Primer M4 (TAKARA SHUZO Co., Ltd.) and M13 Primer RV (TAKARA SHUZO Co., Ltd.), followed by comprehensive interpretation of there results.

The fact that the nucleotide sequences of inserted fragments contained in pVX2P501, pVX2P503, and pVX2P505 are continuous on the genome with the nucleotide sequences of inserted fragments contained in pEXT2pro(F)f3 was confirmed by PCRs and direct sequencing of boundary regions thereof. SEQ ID NO 3 in the Sequence Listing shows an about 3.0 kbp sequence in the promoter region upstream from this azuki bean EXT2 N-terminal amino acid sequence.

EXAMPLE 14

Isolation of Azuki Bean EXT3 Gene Promoter by Inverse PCRs with Hind III, Nsp V, and Xba I Fragments of Azuki Bean Genome DNA Used as Templates With 0.1 μg of the cyclic genome DNA, prepared by complete digestion of an azuki bean genome DNA using restriction enzymes Hind III, Nsp V, and Xba I, followed by self-ligation, in the same manner as described in Example 13, used as the template, PCR using TaKaRa LA PCR Kit (TAKARA SHUZO Co., Ltd.) was carried out by using primer IP45-3 (SEQ ID NO 37) as a sense primer and primer IP45-5 (SEQ ID NO 38) as an antisense primer. The reaction was carried out by repeating a cycle of 94° C. (1 minute), 98° C. (20 seconds), and 67° C. (10 minutes) 30 times, finally followed by 72° C. (10 minutes). After the reaction, 5 μl of the reaction solution underwent 1% agarose gel electrophoresis, indicating that an about 4.5 kbp band was observed only in the sample digested with restriction enzyme Nsp V. For other samples, any amplification was not observed in this reaction. Then, 1 μl each of a 100-fold dilution of the sample digested with restriction enzyme Nsp V and other reaction solution without dilution was used as a template for PCR that was carried out in the same manner by using primer IP45-2 (SEQ ID No 39) as a sense primer and primer IP45-6 (SEQ ID NO 40) as an antisense primer. After the reaction, 5 μl of the reaction solution underwent analysis by 1% agarose gel electrophoresis, confirming that the about 4.5 kbp band was very intense and thus was amplified specifically in the sample digested with restriction enzyme Nsp V. In the sample digested with restriction enzyme Hind III, a large number of seemingly nonspecific DNA fragments were amplified and thus identification of the objective fragment was difficult. Furthermore, in the sample digested with restriction enzyme Xba I, two main bands of about 4.5 kbp and about 3.5 kbp were identified.

Then, from the sample digested with restriction enzyme Nsp V, an about 4.5-kbp DNA fragment obtained in the primary PCR was recovered from the gel and subjected to end-blunting using DNA Blunting Kit (TAKARA SHUZO CO., Ltd.), phosphorylation of the PCR product using the 5'-Terminal-Labeling Kit MEGALABEL™ (TAKARA SHUZO Co., Ltd.) at the 5'-terminus, and then transfer into the Hinc II site of pUC118. The resulting plasmid was transformed into E. coli JM109.

Of colonies obtained, 46 colonies were screened by PCR using primer IP45-2 (SEQ ID NO 39) and M13 Primer 14 (TAKARA SHUZO Co., Ltd.), revealing that 3 colonies were positive. Of these positive colonies, plasmids were extracted from 3 colonies and were named as pVX3P206, pVX3P234, and pVX3P237, respectively.

Each of pVX3P206, pVX3P234, and pVX3P237 was subjected to the sequence analysis of the both terminal portions of respective, inserted fragments according to the Sanger method using M13 Primer M4 (TAKARA SHUZO Co., Ltd.) and M13 Primer RV (TAKARA SHUZO Co., Ltd.). The results indicated that these sequences contained the primers used in the PCR and comparison of these sequences with the sequence (SEQ ID NO 12) of the original azuki bean EXT3 cDNA revealed that the overlapping portions were identical. Also, 3 types of clones had the completely identical sequence in the range analyzed.

When this fragment was completely digested with restriction enzyme Nsp V, the about 4.0 kbp band was separated into two bands of about 0.5 kbp and about 3.5 kbp. Then, PCR method was used to identify which of the two bands of about 0.5 kbp and about 3.5 kbp contained the promoter region. The results revealed that the about 0.5 kbp band was the DNA fragment containing the promoter region.

Then, it was planned that the two main bands of about 4.5 kbp and about 3.5 kbp, obtained by the secondary PCR of the sample digested with restriction enzyme Xba I, were used to clone the 5'-upstream of said promoter region.

When these DNA fragments were completely digested with restriction enzyme Nsp V, the about 4.5 kbp band was separated into two bands of about 0.5 kbp and about 4.0 kbp. On the other hand, the about 3.5 kbp band was not digested with restriction enzyme Nsp V. Accordingly, the about 4.5 kbp band was considered to contain the promoter region.

Then, the restriction map of the about 4.5 kbp DNA fragment was prepared by digestion of the about 4.5 kbp DNA fragment with restriction enzymes Nsp V and Xba I, followed by double digestion with restriction enzymes Nsp V-Xba I.

Figure 12:
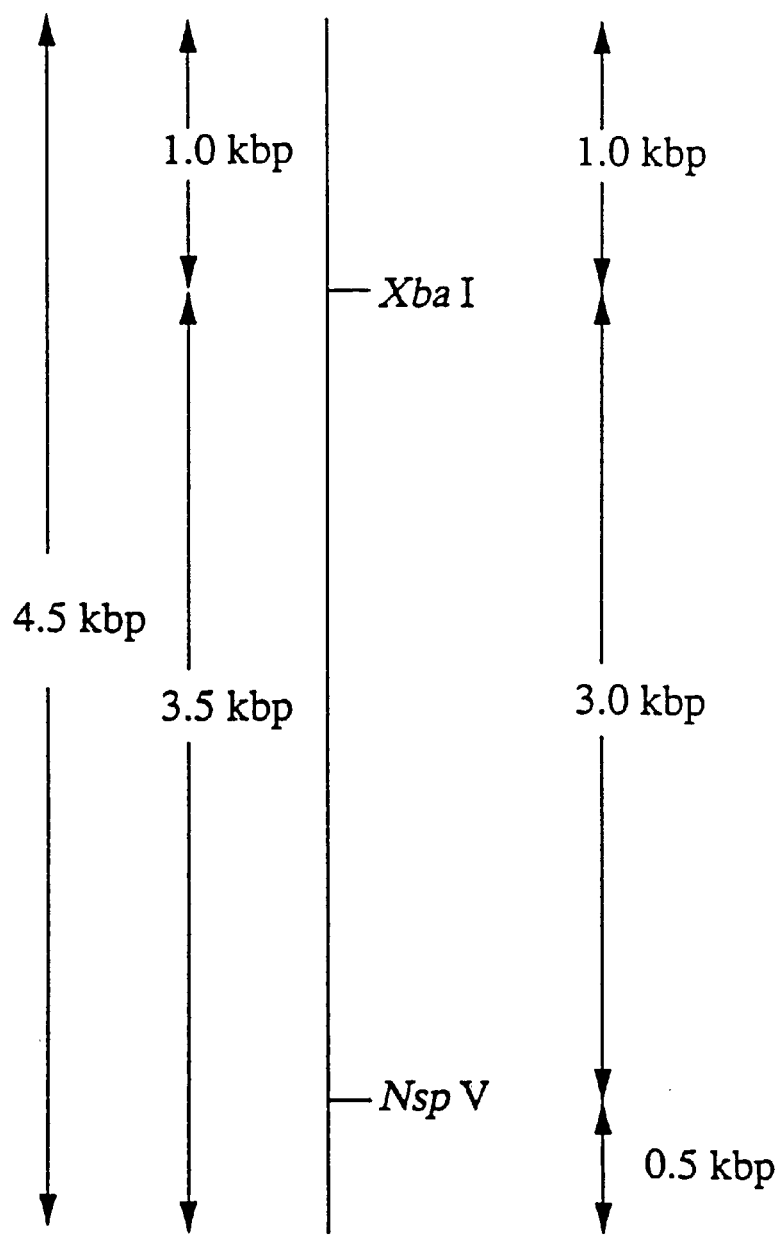
FIG. 12 is a restriction map of the DNA fragment of about 4.5-kbp amplified by PCR in Example 14.

FIG. 12 illustrates the restriction map of the about 4.5 kbp fragment amplified with primers IP45-3 and IP45-5. In the figure, the upper part in the restriction map corresponds to the nucleotide sequence of primer IP45-5 and the lower part corresponds to the nucleotide sequence of primer IP45-3.

As a result, it was revealed that the about 3.0 kbp DNA fragment of Nsp V-Xba I was the 5'-upstream of the promoter region.

Then, the 3.0 kbp DNA fragment formed by double digestion of the about 4.5 kbp DNA fragment with restriction enzymes Nsp V-Xba I was recovered from the gel and transferred into the Xba I-Acc I site of pbluescript SK (−) (Stratagene). The resulting plasmid was transformed into E. coli JM109.

Of the obtained colonies, 7 colonies were screened by PCR using M13 Primer M4 (TAKARA SHUZO Co., Ltd.) and M13 Primer RV (TAKARA SHUZO Co., Ltd.), revealing that 6 colonies contained the about 3.0 kbp inserted fragment. Plasmids were extracted from these 6 colonies and named as pVX3P101, pVX3P103, pVX3P104, pVX3P105, pVX3P106, and pVX3P107, respectively.

Of these plasmids, each of pVX3P101, pVX3P103, pVX3P104, and pVX3P107 were subjected to the partial sequence analysis of the nucleotide sequence of respective, inserted fragment portion according to the Sanger method using M13 Primer M4 (TAKARA SHUZO Co., Ltd.) and M13 Primer RV (TAKARA SHUZO Co., Ltd.), revealing that 4 types of clones had the completely identical sequence. Next, in order to sequence the entire region of the about 3.0 kbp inserted fragment, after complete digestion of pVX3P107 with restriction enzymes Kpn I (TAKARA SHUZO Co., Ltd.) and Xho I (TAKARA SHUZO Co., Ltd.), Kilo-Sequence Deletion Kit (TAKARA SHUZO Co., Ltd.) was utilized to obtain clones that were deleted between the Xho I site and the inserted fragment side. The nucleotide sequences of inserted fragments contained in pVX3P107 were determined by subjecting some selected, deleted clones of appropriate lengths to the sequence analysis of respective, inserted fragment portions according to the Sanger method using M13 Primer M4 (TAKARA SHUZO Co., Ltd.) and M13 Primer RV (TAKARA SHUZO Co., Ltd.), followed by comprehensive interpretation of there results. The fact that the nucleotide sequences of inserted fragments contained in pVX3P206, pVX3P234, and pVX3P237 are continuous on the genome with the nucleotide sequences of inserted fragments contained in pVX3P107 was confirmed by PCRs and direct sequencing of boundary regions thereof. SEQ ID NO 4 in the Sequence Listing shows an about 3.4 kbp sequence in the promoter region upstream from the thus-obtained azuki bean EXT3 N-terminal amino acid sequence.

EXAMPLE 15

Isolation of Azuki Bean XRP1 Gene Promoter by Inverse PCRs with Hind III, Nsp V, and Xba I Fragments of Azuki Bean Genome DNA Used as Templates With 0.1 μg of the cyclic genome DNA, prepared by complete digestion of an azuki bean genome DNA using restriction enzymes Hind III, Nsp V, and Xba I, followed by self-ligation, in the same manner as described in Example 13, used as the template, PCR using TAKARA LA PCR Kit (TAKARA SHUZO Co., Ltd.) was carried out by using primer IPM6-3 (SEQ ID NO 41) as a sense primer and primer IPM6-4 (SEQ ID NO 42) as an antisense primer.

The reaction was carried out by repeating a cycle of 94° C. (1 minute), 98° C. (20 seconds), and 67° C. (10 minutes) 30 times, finally followed by 72° C. (10 minutes). After the reaction, 5 μl of the reaction solution underwent 1% agarose gel electrophoresis, indicating that any amplification was not observed.

Then, 1 μl of the reaction solution was used as a template for PCR that was carried out in the same manner by using primer IPM6-2 (SEQ ID NO 43) as a sense primer and, primer IPM6-5 (SEQ ID NO 44) as an antisense primer. After the reaction, 5 μl of the reaction solution underwent analysis by 1% agarose gel electrophoresis, confirming that in the sample digested with restriction enzyme Hind III and Nsp V, a large number of seemingly nonspecific DNA fragments were amplified and thus identification of the objective fragment was difficult. Furthermore, in the sample digested with restriction enzyme Xba I, two main bands of about 2.5 kbp and about 0.6 kbp were identified.

Then, from the sample digested with restriction enzyme Xba I, two DNA fragments of about 2.5 kbp and about 0.6 kbp obtained in the secondary PCR were recovered from the gel and subjected to end-blunting using DNA Blunting Kit (TAKARA SHUZO Co., Ltd.), phosphorylation of the PCR product using the 5'-Terminal-Labeling Kit MEGALABEL™ (TAKARA SHUZO Co., Ltd.) at the 5'-terminus, and then transfer into the Hinc II site of pUC118. The resulting plasmid was transformed into *E. coli* JM109.

Of each group of colonies obtained, 6 colonies were respectively screened by PCR using M13 Primer M4 (TAKARA SHUZO Co., Ltd.) and M13 Primer RV (TAKARA SHUZO Co., Ltd.), revealing that 5 colonies were positive from the about 2.5 kbp band and 3 colonies were positive from the about 0.6 kbp band. Plasmids were extracted from these positive colonies. The plasmids from the about 2.5 kbp band were named as pXRG301, pXRG302, pXRG303, pXRG304, and pXRG305, respectively. Also, the plasmids from the about 0.6 kbp band were named as pXRG403, pXRG404, and pXRG406, respectively.

Complete digestion of pXRG301, pXRG302, pXRG303, pXRG304, and pXRG305 with both restriction enzymes EcoR I and Sph I (TAKARA SHUZO Co., Ltd.) revealed that only three plasmids from pXRG302, pXRG303, and pXRG304 had an about, 2.5 kbp inserted fragment. Furthermore, complete digestion of pXRG301, pXRG302, pXRG303, pXRG304, pXRG305, pXRG403, pXRG404, and pXRG406 with restriction enzyme Xba I resulted in cleavage at one site in the inserted fragment other than one site in the vector to form an about 1.1 kbp band, whereas pXRG403, pXRG404, and pXRG406 were cleaved only at the site existing in the vector. These results suggested that pXRG301, pXRG302, pXRG303, pXRG304, and pXRG305 contained the objective azuki bean XRP1 promoter region.

Each of pXRG301, pXRG302, pXRG303, and pXRG304 was subjected to the sequence analysis of the both terminal portions of respective, inserted fragments according to the Sanger method using M13 Primer M4 (TAKARA SHUZO Co., Ltd.) and M13 Primer RV (TAKARA SHUZO Co., Ltd.). The results indicated that the sequences of pXRG302 and pXRG303 contained the primers used in the PCR and comparison of these sequences with the sequence (SEQ ID NO 14) of the original azuki bean XRP1 cDNA revealed that the overlapping portions were identical. Also, 2 types of clones had the completely identical sequence.

Figure 13:
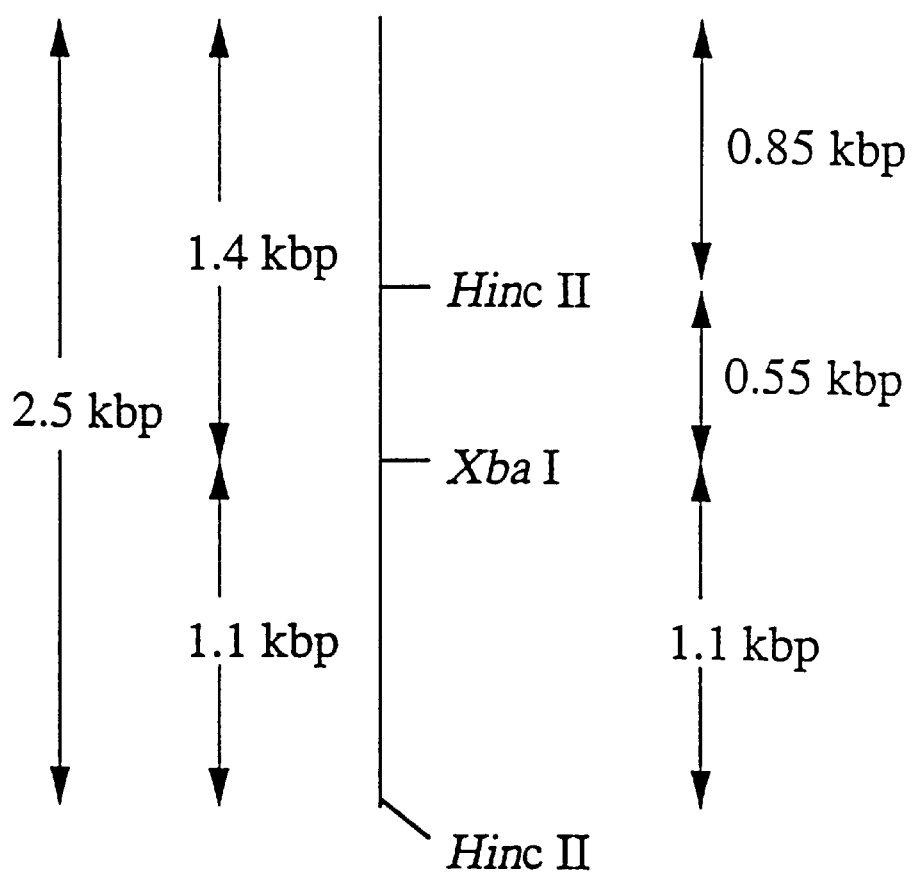
FIG. 13 is a restriction map of the fragment inserted in pXRG302.

FIG. 13 illustrates the restriction map of the about 2.5 kbp fragment amplified with primers IPM6-2 and IPM6-5. In the figure, the upper part in the restriction map corresponds to the nucleotide sequence of primer IPM6-5 and the lower part corresponds to the nucleotide sequence of primer IPM6-2.

The nucleotide sequence of an azuki bean XRP1 promoter region of about 1.1 kbp in inserted fragments contained in pXRG302 was determined by the sequence analysis of respective, inserted fragment portions according to the Sanger method using M13 Primer M4 (TAKARA SHUZO Co., Ltd.) and M13 Primer RV (TAKARA SHUZO Co., Ltd.), followed by further analysis of a primer synthesized on the basis of the sequence in the inserted fragments and comprehensive interpretation of there results. SEQ ID NO 5 in the Sequence Listing shows an about 1.1 kbp sequence in the promoter region upstream from this azuki bean XRP1 N-terminal amino acid sequence.

EXAMPLE 16

Isolation of Tomato Gene Promoter by Inverse PCRs with EcoR I, Hind III, Nsp V, and Xba I Fragments of Tomato Genome DNA Used as Templates Seeds of *Lycopersicon esculentum* cv. Ponterosa (TAXII SEED Co., Ltd.) were germinated and then cultivated for about one month to obtain about 10 g of leaves and stems. About 2.5 g of these leaves and stems were pulverized in a mortar in the presence of liquid nitrogen to prepare a white powder. The resulting leave and stem powder was immediately placed in a 50 ml polystyrene tube and extracted with 10 ml of a urea-phenol DNA extraction buffer solution [0.05 M Tris-HCl (pH: 7.6), 0.02 M EDTA, 5% phenol, 8 M urea, 0.35 M NaCl, and 2% sodium lauroylsarcosinate] mixed with 25% SDS at 65° C. for 1 hour. The extract was mixed with a 2-fold volume of a phenolchloroform-isoamyl alcohol (25:24:1) mixture, stirred gently for about 15 minutes, and then centrifuged at 2000 rpm for 15 minutes. After the centrifugation, the supernatant was transferred into a new tube, again mixed with a 2-fold volume of a phenol-chloroform-isoamyl alcohol (25:24:1) mixture, stirred gently for about 15 minutes, and then centrifuged at 2000 rpm for 15 minutes. The supernatant after this centrifugation was transferred into a new tube, mixed with a 2-fold volume of ethanol, and stirred gently. Then, the precipitated, white genome DNA was coiled out by using a Pasteur pipet and transferred into a new tube. To this tube was added 1.5 ml of a TE buffer solution [10 mM Tris-HCl (pH: 8.0) and 1 mM EDTA] and the resulting mixture was kept at 55° C. overnight to dissolve the DNA. Analysis of 1 µl of a sample, prepared by diluting of this DNA solution 10-fold, by 0.4% agarose gel electrophoresis revealed that the solution contained a high molecular DNA at a concentration of about 100 ng/µl. In other words, about 150 µg of the genomic DNA was obtained from about 2.5 g of the plant portions.

One µg of this genomic DNA was taken in separate tubes and subjected to complete digestion using restriction enzymes EcoR I, Hind III, Nsp V, and Xba I, respectively, followed by self-ligation, in the same manner as described in Example 13. With 0.1 µg of the thus-prepared cyclic genomic DNA used as the template, PCR using TAKARA LA PCR Kit (TAKARA SHUZO Co., Ltd.) was carried out by using primer IPLE-3 (SEQ ID NO 45) as a sense primer and primer IPLE-4 (SEQ ID NO 46) as an antisense primer. The reaction was carried out by repeating a cycle of 94° C. (1 minute), 98° C. (20 seconds), and 67° C. (10 minutes) 30 times, finally followed by 72° C. (10 minutes). After the reaction, 5 µl of the reaction solution underwent 1% agarose gel electrophoresis, indicating that an about 6.6-kbp band was observed in the sample digested with restriction enzymes Hind III and Xba I. For other samples, any amplification was not observed in this reaction. Then, with 1 µl of the reaction solution, obtained from the sample digested with restriction enzyme Xba I, used as the template, secondary PCR using TAKARA LA PCR Kit (TAKARA SHUZO Co., Ltd.) was carried out by using primer IPLE-2 (SEQ ID NO 47) as a sense primer and primer IPLE-5 (SEQ ID NO 48) as an antisense primer. The reaction was carried out under the same conditions as described above by repeating the cycle 10 times. After the reaction, the obtained DNA fragments were recovered from the gel and then transferred into pT7Blue T-Vector (Novagen). The resulting plasmids were transformed into E. coli JM109.

Of the obtained colonies, 12 colonies were screened by PCR using TAKARA LA PCR Kit (TAKARA SHUZO Co., Ltd.) was carried out by using primer IPLE-1 (SEQ ID NO 49) and primer IPLE-6 (SEQ ID NO 50), indicating that 6 colonies were positive. Plasmids were extracted from these 6 colonies and named as pLXG101, pLXG102, pLXG103, pLXG106, pLXG109, and pLXG110, respectively.

Each of pLXG101, pLXG102, and pLXG106 was subjected to the sequence analysis of respective, inserted fragments according to the Sanger method using M13 Primer M4 (TAKARA SHUZO Co., Ltd.) and M13 Primer RV (TAKARA SHUZO Co., Ltd.).

Comparison of these sequences with the sequence [EP-0562836 A1 (1993)] of the original tomato EXT cDNA revealed that the overlapping portions were identical. However, 2 to 3 base substitution was detected within the sequenced range. It was conceived that this substitution involved a mistake induced by the nested PCR in the polymerase reaction. Accordingly, after the promoter region in one of the 6 plasmids was sequenced, a primer was synthesized and other clones were also sequenced, thereby inferring the sequence on the actual genome.

Figure 14:
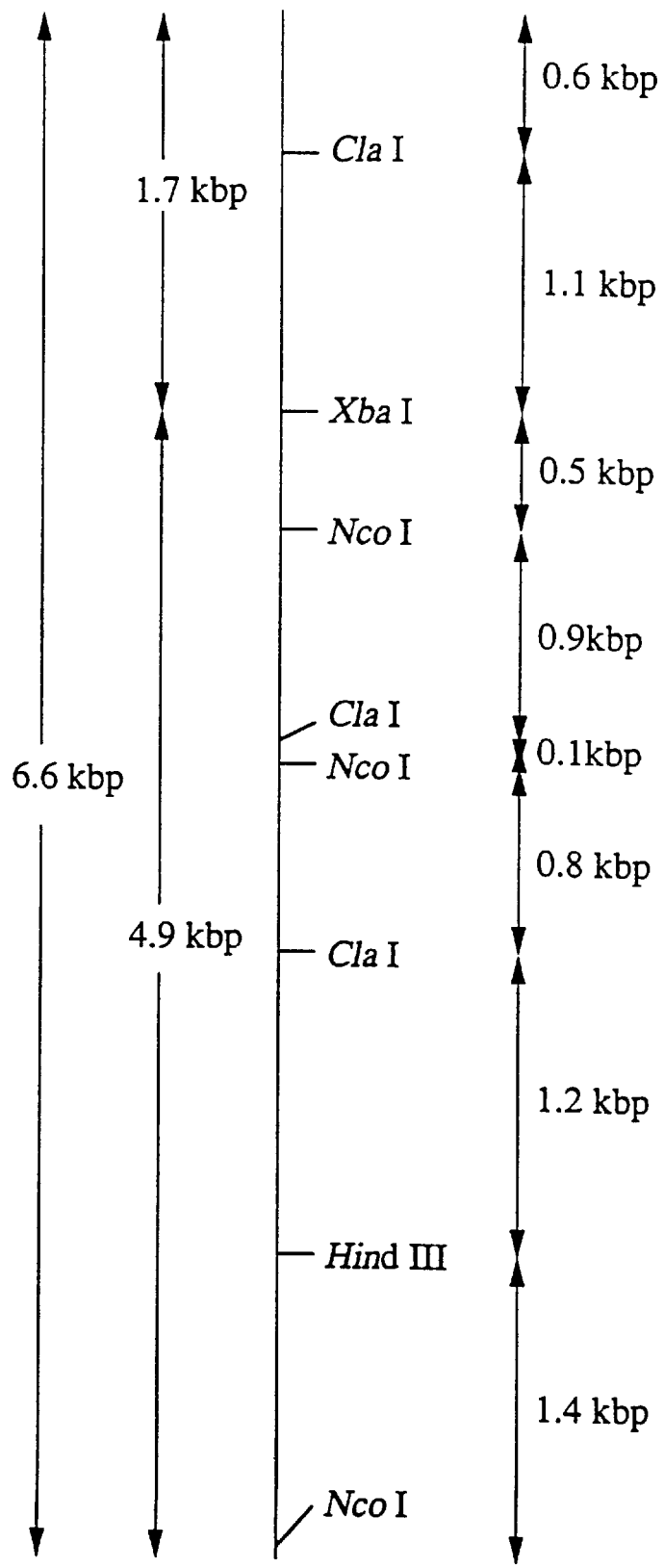
FIG. 14 is a restriction map of the fragment inserted in pLXG101.

FIG. 14 illustrates the restriction map of the about 6.6 kbp inserted fragment amplified with primers IPLE-2 and IPLE-5. In the figure, the upper part in the restriction map corresponds to the nucleotide sequence of primer IPLE-5 and the lower part corresponds to the nucleotide sequence of primer IPLE-2.

Moreover, complete digestion of pLXG101, pLXG102, pLXG103, pLXG106, pLXG109, and pLXG110 with restriction enzyme Xba I, followed by agarose electrophoresis, revealed formation of two bands around about 4.9 kpb for pLXG101, pLXG102, pLXG103, and pLXG110 as well as two bands at about 8.1 kbp and at about 1.7 kbp for pLXG106 and pLXG109. This observation indicated that PCR-amplified DNA fragments were inserted in the reverse directions for three plasmids of pLXG101, pLXG102, pLXG103, and pLXG110 and for two plasmids of pLXG106 and pLXG109. In addition, it was revealed from the results on PCR using TAKARA LA PCR Kit (TAKARA SHUZO Co., Ltd.), which was carried out, with these plasmids used as templates, by using M13 Primer M4 (TAKARA SHUZO Co., Ltd.) and primer IPLE-1 (SEQ ID NO 49), that the about 4.9 kbp DNA fragment contained the tomato EXT gene promoter region, among the DNA fragments of about 4.9 kbp and about 1.7 kbp which were separated upon complete digestion of the inserted fragment with restriction enzyme Xba I.

Then, pLXG106 was subjected to complete digestion with restriction enzyme Xba I, followed by ethanol precipitation. The ethanol-precipitated DNA was mixed with 268 µl of distilled water, 30 µl of a 10×ligation buffer solution, and 3 µl of T4DNA Ligase (TAKARA SHUZO Co., Ltd.) and then underwent self-ligation by reaction at 16° C. overnight. The resulting plasmids were transformed into E. coli JM109.

Of the obtained colonies, plasmids were extracted from 4 colonies and named as pLXG601, pLXG602, pLXG603, and pLXG604, respectively. Double digestion of these pLXG601, pLXG602, pLXG603, and pLXG604 with restriction enzymes EcoR I-Pst I, followed by agarose electrophoresis, revealed that the about 4.9 kbp inserted fragment existed in all of these plasmids.

Furthermore, since the above-mentioned restriction map (FIG. 14) has indicated the existence of one Hind III site in the about 4.9 kbp inserted fragment, pLXG106 was subjected to complete digestion with restriction enzyme Hind III, followed by addition of 268 µl of distilled water, 30 µl of a 10×ligation buffer solution, and 3 µl of T4DNA Ligase (TAKARA SHUZO Co., Ltd.) to the ethanol-precipitated DNA and then self-ligation by reaction at 16° C. overnight. The resulting plasmids were transformed into E. coli JM109.

Of the obtained colonies, plasmids were extracted from 6 colonies and named as pLXP101, pLXP102, pLXP103, pLXP106, pLXP109, and pLXP111, respectively. Double digestion of these pLXP101, pLXP102, pLXP103, pLXP106, pLXP109, and pLXP111 with restriction enzymes EcoR I-Pst I, followed by agarose electrophoresis, revealed that the about 1.4-kbp-inserted fragment existed in all of these plasmids.

pLXP101 was subjected to the sequence analysis of the nucleotide sequence of the inserted fragment portion according to the Sanger method using M13 Primer M4 (TAKARA SHUZO Co., Ltd.) and M13 Primer RV (TAKARA SHUZO Co., Ltd.).

Next, in order to sequence the entire region of the about 1.4-kbp-inserted fragment in pLXP101, after complete digestion of pLXP101 with restriction enzymes Kpn I and BamH I, Kilo-Sequence Deletion Kit (TAKARA SHUZO Co., Ltd.) was utilized to obtain clones that were deleted between the BamH I site and the inserted fragment side. The nucleotide sequences of inserted fragments contained in pLXP101 were determined by subjecting some selected, deleted clones of appropriate lengths to the sequence analysis of respective, inserted fragment portions according to the Sanger method using M13 Primer M4 (TAKARA SHUZO Co., Ltd.) and M13 Primer RV (TAKARA SHUZO Co., Ltd.), followed by comprehensive interpretation of there results. In addition, the about 1.4 kbp promoter region in pLXG102 and pLXG103, using the primers synthesized on the basis of the nucleotide sequence of the pLXP101-inserted fragment, was sequenced and compared, thereby inferring the sequence for the about 1.4 kbp promoter region in the upstream from the tomato EXT gene N-terminal amino acid sequence. This sequence is shown in SEQ ID NO 6 in the Sequence Listing.

EXAMPLE 17

Isolation of Tobacco EXT Gene Promoter by Inverse PCRs with EcoR I, Hind III, Nsp V, and Xba I Fragments of Tobacco Genome DNA Used as Templates About 150 mg of the tobacco BY2 culture cells (callus) was pulverized in a mortar to a powder, which was mixed with 0.5 ml of an extraction solution [15% sucrose, 50 mM Tris-HCl (pH 8.0), and 50 mM EDTA], transferred into an Eppendorf tube, and centrifuged at 500 rpm for 1 minute. The precipitate was dissolved in 300 µl of 2T-1E [20 mM Tris-HCl (pH 8.0) and 10 mM EDTA], mixed with 40 µl of 10% SDS, shaken slowly, and then treated at 70° C. for 15 minutes. The resulting solution was mixed with 225 µl of 5 M ammonium acetate, stirred, placed on ice for 30 minutes, and centrifuged at 15000 rpm for 15 minutes. After centrifugation, the supernatant was transferred into a new tube, mixed with 0.7 m21 of isopropanol, stirred, allowed to stand at room temperature for 15 minutes, and centrifuged at 15000 rpm for 15 minutes. After the supernatant was removed, the residue was mixed with ice-cold 80% ethanol and centrifuged at 15000 rpm for 15 minutes. The precipitate was dried and mixed with 100 µl of a TE buffer solution [10 mM Tris-HCl (pH: 8.0) and 1 mM EDTA], and the resulting mixture was kept at 4° C. overnight to dissolve the DNA. Analysis of 5 µl of the DNA solution by 0.4% agarose gel electrophoresis revealed that the solution contained a high molecular DNA at a concentration of about 100 ng/µl. In other words, about 10 µg of the genomic DNA was obtained from about 150 mg of the callus.

One µg of this genomic DNA was taken in separate tubes and subjected to complete digestion using restriction enzymes EcoR I, Hind III, Nsp V, and Xba I, respectively, followed by self-ligation, in the same manner as described in Example 13. With 0.1 µg of the thus-prepared cyclic genome DNA used as the template, PCR using TAKARA LA PCR Kit (TAKARA SHUZO Co., Ltd.) was carried out by using primer IPTE-3 (SEQ ID NO 51) as a sense primer and primer IPTE-4 (SEQ ID NO 52) as an antisense primer. The reaction was carried out by repeating a cycle of 94° C. (1 minute), 98° C. (20 seconds), and 67° C. (10 minutes) 30 times, finally followed by 72° C. (10 minutes). After the reaction, 5 µl of the reaction solution underwent 1% agarose gel electrophoresis, indicating that an about 1.2 kbp band was observed in the sample digested with restriction enzyme Xba I. For other samples, any amplification was not observed in this reaction. Then, with 1 µl of the above reaction solution, obtained from the sample digested with restriction enzyme Xba I, used as the template, secondary PCR using TAKARA LA PCR Kit (TAKARA SHUZO Co., Ltd.) was carried out by using primer IPTE-2 (SEQ ID NO 53) as a sense primer and primer IPTE-5 (SEQ ID NO 54) as an antisense primer. The reaction was carried out under the same conditions as described above. As a result, a DNA fragment of about 1.1 kbp was amplified. The DNA fragments obtained by the secondary PCR were recovered from the gel and then transferred into pT7Blue T-Vector (Novagen). The resulting plasmids were transformed into Nova Blue Competent Cells (Novagen).

Of the obtained colonies, 12 colonies were screened by PCR using primer IPTE-1 (SEQ ID NO 55) and primer IPTE-6 (SEQ ID NO 56), indicating that all 12 colonies were positive. Of them, plasmids were extracted from 6 colonies and named as pNXG101, pNXG102, pNXG103, pNXG104, pNXG105, and pNXG106, respectively.

Each of pNXG102, pNXG103, and pNXG104 was subjected to the sequence analysis of respective, inserted fragments according to the Sanger method using M13 Primer M4 (TAKARA SHUZO Co., Ltd.) and M13 Primer RV (TAKARA SHUZO Co., Ltd.). Comparison of these sequences with the sequence (JP 7-79778 A) of the original tobacco EXT cDNA revealed that the overlapping portions were completely identical.

Figure 15:
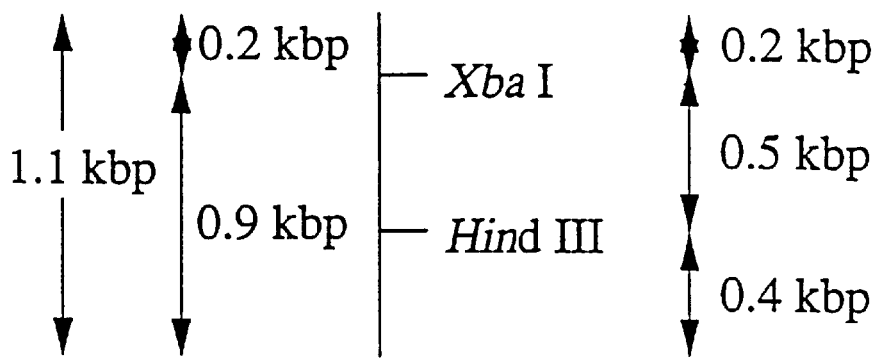
FIG. 15 is a restriction map of the fragment inserted in pNXG102.

FIG. 15 illustrates the restriction map of the about 1.1 kbp inserted fragment amplified with primers IPTE-2 and IPTE-5. In the figure, the upper part in the restriction map corresponds to the nucleotide sequence of primer IPTE-5 and the lower part corresponds to the nucleotide sequence of primer IPTE-2.

Moreover, complete digestion of pNXG101, pNXG102, pNXG103, pNXG104, pNXG105, and pNXG106 with restriction enzyme Xba I, followed by agarose electrophoresis, revealed formation of two bands at about 3.1 kbp and at about 0.9 kbp for pNXG101 as well as two bands at about 3.8 kbp and at about 0.2 kbp for pNXG102, pNXG103, pNXG104, pNXG105, and pNXG106. This observation indicated that the EXT was inserted in the reverse directions for pNXG101 and for pNXG102, pNXG103, pNXG104, pNXG105, and pNXG106. In addition, it was revealed from the results on PCR, which was carried out, with these plasmids used as templates, by using M13 Primer M4 (TAKARA SHUZO Co., Ltd.) and primer IPTE-1 (SEQ ID NO 55) or primer IPTE-6 (SEQ ID NO 56), that the about 0.9 kbp DNA fragment contained the tobacco EXT gene promoter region, among the DNA fragments of about 0.9 kbp and about 0.2 kbp which were separated upon complete digestion of the inserted fragment with restriction enzyme Xba I.

Then, pNXG103 was subjected to complete digestion with restriction enzyme Hind III, followed by ethanol precipitation. The ethanol-precipitated DNA was mixed with 268 µl of distilled water, 30 µl of a 10×ligation buffer solution, and 3 µl of T4 DNA Ligase (TAKARA SHUZO Co., Ltd.) and then underwent self-ligation by reaction at 16° C. overnight. The resulting plasmids were transformed into E. coli JM109. Plasmids were extracted from 3 colonies and named as pT-EXT-4, pT-EXT-5, and pT-EXT-6, respectively. Double digestion of these pT-EXT-4, pT-EXT-5, and pT-EXT-6 with restriction enzymes Hind III-EcoR I, followed by agarose electrophoresis, revealed that the about 0.4 kbp inserted fragment existed in all of these plasmids. These pT-EXT-4, pT-EXT-5, and pT-EXT-6 were subjected to the sequence analysis of the nucleotide sequence of the inserted fragment portion according to the Sanger method using M13 Primer M4 (TAKARA SHUZO Co., Ltd.) and T7 Promoter Primer (Novagen).

Furthermore, pNXG102 was completely digested with restriction enzymes Hind III and Xba I, and an about 0.5 kbp band was cut out by agarose gel electrophoresis for purification.

Next, this DNA fragment was ligated to the molecule obtained by double digestion of pUC18 (TAKARA SHUZO Co., Ltd.) with restriction enzymes Hind III-Xba I. The resulting plasmids were transformed into E. coli JM109.

Of the obtained colonies, plasmids were extracted from 3 colonies and named as pT-EXT-1, pT-EXT-2, and pT-EXT-3, respectively. Double digestion of these pT-EXT-1, pT-EXT-2, and pT-EXT-3 with restriction enzymes Hind III-EcoR I, followed by agarose electrophoresis, revealed that the about 0.5 kbp inserted fragment existed in all of these plasmids.

These pT-EXT-1, pT-EXT-2, and pT-EXT-3 were subjected to the sequence analysis of the nucleotide sequence of the inserted fragment portion according to the Sanger method using M13 Primer M4 (TAKARA SHUZO Co., Ltd.) and M13 Primer RV (TAKARA SHUZO Co., Ltd.).

On the basis of comprehensive interpretation of there results, the entire nucleotide sequence in the promoter region upstream from this tobacco EXT N-terminal amino acid sequence was determined. This sequence is shown by SEQ ID NO 7 in the Sequence Listing.

EXAMPLE 18

Isolation of Wheat Gene Promoter by Inverse PCRs with EcoR I, Hind III, Nsp V, and Xba I Fragments of Wheat Genome DNA Used as Templates One μg of a wheat genome DNA (Clontech) was taken in separate tubes and subjected to complete digestion using restriction enzymes EcoR I, Hind III, Nsp V, and Xba I, respectively, followed by self-ligation, in the same manner as described in Example 13. With 0.1 μg of the thus-prepared cyclic genome DNA used as the template, PCR using TAKARA LA PCR Kit (TAKARA SHUZO Co., Ltd.) was carried out by using primer KOM-1 (SEQ ID NO 57) as a sense primer and primer KOM-4 (SEQ ID NO 58) as an antisense primer in the reaction system with a total volume of 50 μl. The reaction was carried out by repeating a cycle of 94° C. (1 minute), 98° C. (20 seconds), and 67° C. (10 minutes) 30 times, finally followed by 72° C. (10 minutes). After the reaction, 5 μl of the reaction solution underwent 1% agarose gel electrophoresis, indicating that an about 4.3 kbp band and an about 3.5 kbp band were observed in the sample digested with restriction enzyme Hind III. Also, an about 5.0 kbp band was observed in the sample digested with restriction enzyme Nsp V. For other samples, any amplification was not observed in this reaction.

Then, with 1 μl of the primary PCR reaction solution, obtained from the sample digested with restriction enzyme Hind III, used as the template, nested PCR using TAKARA LA PCR Kit (TAKARA SHUZO Co., Ltd.) was carried out by using primer KOM-2 (SEQ ID NO 59) as a sense primer and primer KOM-5 (SEQ ID NO 60) as an antisense primer in the reaction system with a total volume of 50 μl. The reaction was carried out by repeating a cycle of 94° C. (1 minute), 98° C. (20 seconds), and 67° C. (10 minutes) 30 times, finally followed by 72° C. (10 minutes). After the reaction, 5 μl of the reaction solution underwent 1% agarose gel electrophoresis, indicating that only an about 3.3 kbp band was observed. Then, the resulting DNA fragment was recovered from the gel and subjected to end-blunting using DNA Blunting Kit (TAKARA SHUZO Co., Ltd.), phosphorylation of the PCR product using the 5'-Terminal-Labeling Kit MEGALABEL™ (TAKARA SHUZO Co., Ltd.) at the 5'-terminus, and then transfer into the Hinc II site of pUC119 (TAKARA SHUZO Co., Ltd.). The resulting plasmid was transformed into E. coli JM109.

Of the obtained colonies, 15 colonies were screened for plasmids containing inserted fragments of appropriate lengths by colony-picking PCR using M13 Primer M4 (TAKARA SHUZO Co., Ltd.) and M13 Primer RV (TAKARA SHUZO Co., Ltd.), indicating that 8 out of 15 colonies were positive. Of them, plasmids were extracted from these 6 colonies and named as pKOM-1, pKOM-2, pKOM-3, pKOM-4, pKOM-5, and pKOM-6, respectively.

Each of pKOM-1, pKOM-2, pKOM-3, pKOM-4, pKOM-5, and pKOM-6 was subjected to the sequence analysis of the both termini of respective, inserted fragments according to the Sanger method using M13 Primer M4 (TAKARA SHUZO Co., Ltd.) and M13 Primer RV (TAKARA SHUZO Co., Ltd.). Comparison of these sequences with the sequence [EP-0562836 A1 (1993)] of the original wheat EXT cDNA revealed that the overlapping portions were completely identical. However, 2 to 3 base substitution was detected within the sequenced range. It was conceived as in the case of tomato that this substitution involved a mistake induced by the nested PCR in the polymerase reaction.

Figure 16:
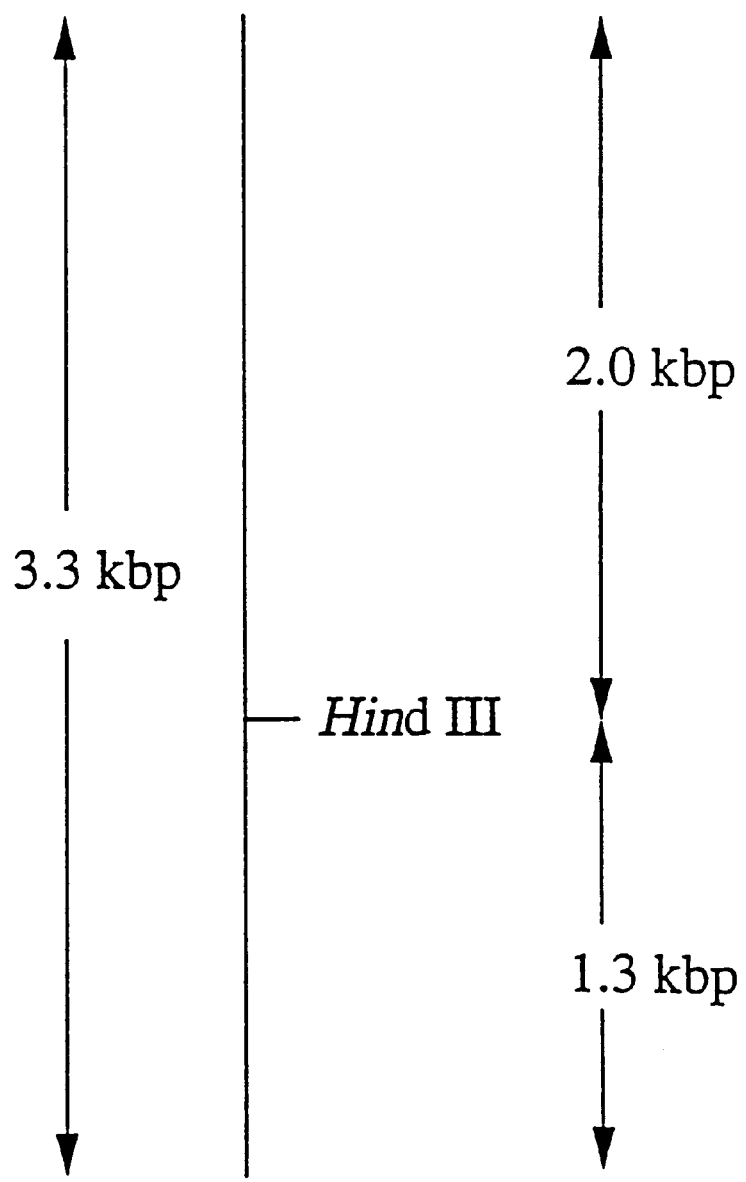
FIG. 16 is a restriction map of the fragment inserted in pKOM-1.

FIG. 16 illustrates the restriction map of the about 3.3 kbp inserted fragment amplified with primers KOM-2 and KOM-5. In the figure, the upper part in the restriction map corresponds to the nucleotide sequence of primer KOM-5 and the lower part corresponds to the nucleotide sequence of primer KOM-2.

Complete digestion of pKOM-1, pKOM-2, pKOM-3, pKOM-4, pKOM-5, and pKOM-6 with restriction enzyme Hind III, followed by agarose electrophoresis, revealed formation of two bands at about 4.2 kpb and at about 2.0 kbp for pKOM-1, pKOM-3, and pKOM-5 as well as two bands at about 4.9 kbp and at about 1.3 kbp for pKOM-2, pKOM-4, and pKOM-6. This observation indicated that the EXT was inserted in the reverse directions for the three bands of pKOM-1, pKOM-3, and pKOM-5 and for the three bands of pKOM-2, pKOM-4, and pKOM-6. In addition, it was revealed from the results on PCR, which was carried out, with these plasmids used as templates, by using primer KOM-2 (SEQ ID NO 59) and M13 Primer M4 (TAKARA SHUZO Co., Ltd.) or M13 Primer RV (TAKARA SHUZO Co., Ltd.), that the about 1.3-kbp DNA fragment contained the wheat EXT gene promoter region, among the DNA fragments of about 2.0 kbp and about 1.3 kbp which were separated upon complete digestion of the inserted fragment with restriction enzyme Hind III.

Then, pKOM-1 was completely digested with restriction enzyme Hind III and the about 1.3-kbp DNA fragment, namely a DNA fragment containing the wheat EXT gene promoter region, was subjected to purification by agarose electrophoresis, followed by self-ligation using TAKARA DNA Ligation Kit (TAKARA SHUZO Co., Ltd.). The resulting plasmids were transformed into E. coli JM109.

Figure 17:
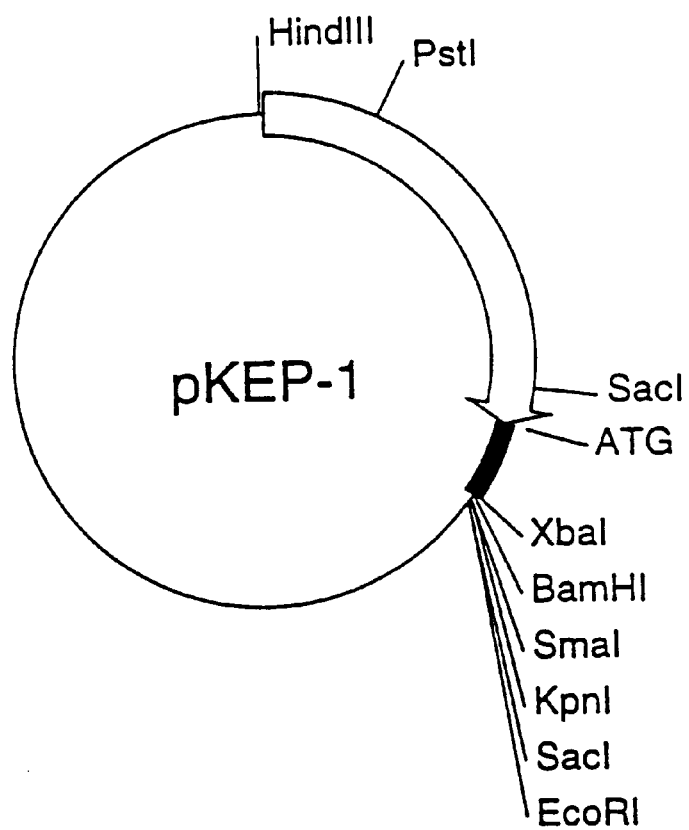
FIG. 17 is a restriction map of pKEP-1.

Of the obtained colonies, 6 colonies were examined for the size of the inserted fragment by PCR to detect an about 1.3 kbp DNA fragment. Then, plasmids were extracted from 3 colonies and named as pKEP-1, pKEP-2, and pKEP-3, respectively. Complete digestion of these pKEP-1, pKEP-2, and pKEP-3 with restriction enzymes EcoR I, Sac I, Kpn I, Sma I, BamH I, Xba I, Pst I, and Hind III, followed by agarose electrophoresis, was carried out to prepare their restriction maps. Of them, the restriction map of pKEP-1 is shown in FIG. 17.

Next, each of KEP-1, KEP-2, and KEP-3 was completely digested with restriction enzyme Sac I and the about 3.8 kbp band was subjected to purification by agarose electrophoresis, followed by self-ligation using TAKARA DNA Ligation Kit (TAKARA SHUZO Co., Ltd.). The resulting plasmids were named as pKEPS-1, pKEPS-2, and pKEPS-3.

Furthermore, each of pKEPS-1, pKEPS-2, and pKEPS-3 was subjected to double digestion with restriction enzyme EcoR I-Pst I and purification of the about 1.1 kbp band by agarose electrophoresis. Then, this DNA fragment was ligated to the molecule obtained by double digestion of pUC19 (TAKARA SHUZO Co., Ltd.) with restriction enzymes EcoR I-Pst I. The resulting plasmids were transformed into E. coli JM109.

Of the obtained colonies, 5 colonies were screened for the size of the inserted fragment of the about 1.1 kbp by PCR using M13 Primer M4 (TAKARA SHUZO Co., Ltd.) and M13 Primer RV (TAKARA SHUZO Co., Ltd.). The plasmids were extracted from positive colonies and named as pKEPEP-1, KEPPEP-2, and KEPPEP-3, respectively.

Each of these pKEP-1, pKEP-2, pKEP-3, pKEPS-1, pKEPS-2, pKEPS-3, pKEPEP-1, KEPPEP-2, and KEPPEP-3 was subjected to the sequence analysis of the nucleotide sequence of the respective, inserted fragment portion according to the Sanger method using M13 Primer M4 (TAKARA SHUZO Co., Ltd.) and M13 Primer RV (TAKARA SHUZO Co., Ltd.).

On the basis of comprehensive interpretation of there results, the entire nucleotide sequence in the promoter region upstream from this wheat EXT N-terminal amino acid sequence contained in pKEP-1 was determined. This sequence is shown by SEQ ID NO 8 in the Sequence Listing.

EXAMPLE 19

Analysis of Expression Mode for Tomato EXT Gene
(1) Preparation of Total RNA

Each of 5 g tissues collected from leaves, stems (during elongation and after elongation), and fruits [mature green fruit (of which the surface is green and a gelly substance is formed in the inside) and mature red fruit] of Arisa Craig, a tomato plant, was frozen, and pulverized using a mortar in liquid nitrogen. The pulverized tissues were mixed with 5 ml of an extraction solution [0.2 M Tris-HCl (pH: 9.0), 0.1 M NaCl, 10 mM EDTA, 0.5% SDS, and 14 mM 2-mercaptoethanol], and 5 ml of a phenol-chloroform-isoamyl alcohol (50:49:1) mixture and stirred vigorously. The resulting suspension was centrifuged to separate an aqueous layer. This procedure was repeated twice. The separated aqueous layer was mixed with a 1/10 volume of 3 M sodium acetate, cooled with ice for 20 minutes, and centrifuged. The supernatant was recovered, mixed with ethanol, and then centrifuged to obtain a precipitate. This precipitate was dissolved in 2 ml of a TE/HPRI solution [10 mM Tris-HCl, 1 mM EDTA, 5U/ml Rnase inhibitor (TAKARA SHUZO Co., Ltd.) and 1 mM dithiothreitol (DTT)], mixed with a ¼ volume of 10 M lithium chloride, cooled with ice for 2 hours, and then centrifuged. The obtained precipitate was dissolved in 0.5 ml of the TE/HPR I solution, mixed with 3 M sodium acetate and ethanol, and then centrifuged to obtain an RNA precipitate.

(2) Northern Hybridization

Each of a fragment of the tomato EXT cDNA [EP-0562836 A1 (1993)] and a cDNA fragment of tomato fruit polygalacturonase (Tomato PG) [Molecular & General Genetics, 208, 30–36 (1987)] was labeled with [α-$^{32}$P]dCTP using BcaBEST™ Labeling Kit (TAKARA SHUZO Co., Ltd.) to prepare a probe for northern hybridization, respectively. The northern hybridization was carried out in the following way according to a modification of the method described in "Molecular Cloning, A laboratory Manual", Second Edition, Chapter 7, pp. 7.39–7.52 (T. Maniatis et al., Published by Cold Spring Harbor Laboratory Press in 1989). That is to say, 2 μg of the extracted RNA was subjected to electrophoresis with formaldehyde-running agarose gel (1%), followed by northern blotting on a nylon membrane (Hybond-N$^+$) overnight. After RNA was immobilized by irradiation with a ultraviolet transilluminator (254 nm) for 3 minutes, the membrane was subjected to pre-hybridization in 25 ml of a pre-hybridization buffer solution (6×SSC, 0.1% SDS, 5×Denhardt's solution, and 100 μg/ml salmon sperm DNA) at 65° C. for 2 hours.

The $^{32}$P-labeled probe prepared by the above-mentioned method was added to 25 ml of a pre-hybridization buffer solution (6×SSC, 0.1% SDS, 5×Denhardt's solution). To this probe solution was added the membrane obtained by the pre-hybridization and hybridization was carried out at 65° C. overnight.

After the hybridization, the membrane was washed thrice with a washing solution containing 2×SSC and 0.1% SDS at 65° C. for 20 minutes. After being dried, the membrane was exposed overnight at −80° C. in a cassette in which an X-ray film (Kodak) was placed to prepare an autoradiograph.

Figure 18:
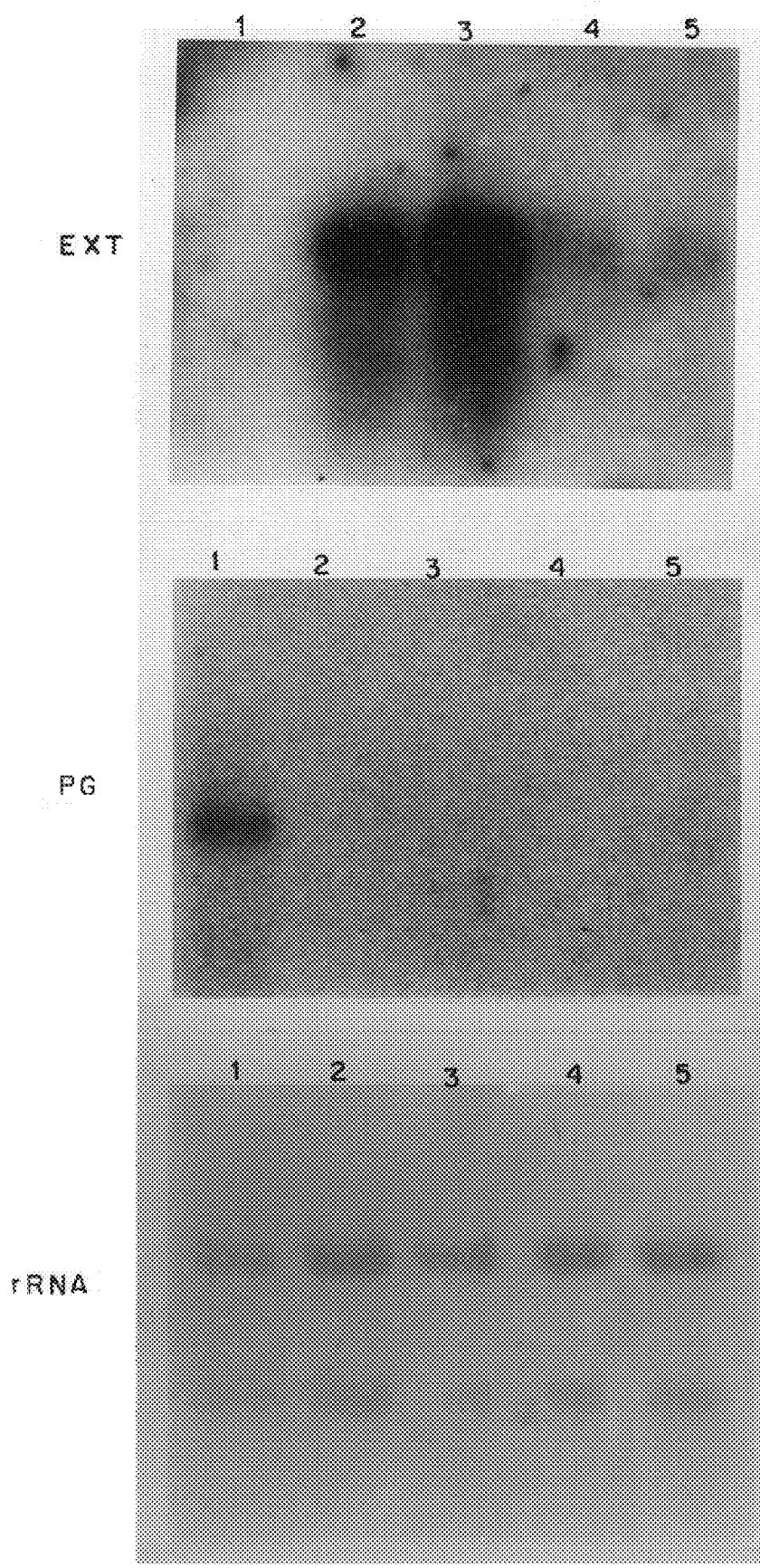
FIG. 18 illustrates an electrophoresis migration patter of northern hybridization of the plant in Example 19.

The results are shown in FIG. 18. That is to say, FIG. 18 illustrates the northern hybridization using the tomato tissues, wherein the expression of a tomato EXT mRNA was shown in the upper row, the expression of a Tomato PG mRNA was shown in the middle row, and the rRNA levels were shown in the lower row. Also in the figure, lane 1 indicates the mature red fruit, lane 2 the mature green fruit (of which the surface is green and a gelly substance is formed in the inside), lane 3 the elongating stems, lane 4 the elongated stems, and lane 5 the leaves.

As can be seen from FIG. 18, it was revealed on comparison of the expression level of the tomato EXT mRNA between each of the plant tissues that an intense expression was observed particularly in the mature green fruit and in the elongating stems. In contrast, the Tomato PG mRNA used as a control, on comparison of the expression level between each of the plant tissues, was expressed intensely in the mature red fruit.

(3) RT-PCR Using Tomato Fruits

According to the procedure as shown in Example 19 (1), total RNAs were prepared from 10 kinds of fruits in different ripening stages ranging from an immature green fruit (of which the surface is green but a gelly substance is not formed in the inside) to a mature red fruit of Arisa Craig, a tomato plant. One μg each of these total RNA was utilized for RT-PCR using TAKARA RNA PCR Kit with AMV Version 2 (TAKARA SHUZO Co., Ltd.) in the following manner to analyze the expression of the tomato EXT mRNA and Tomato PG mRNA.

Figure 19:
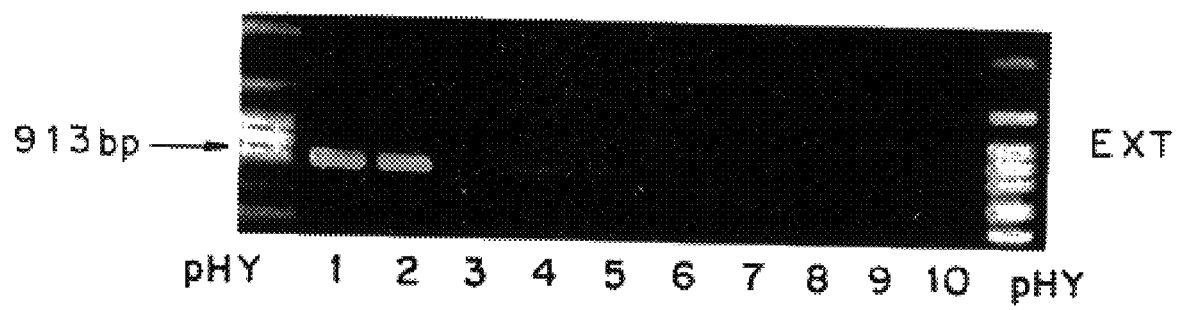
FIG. 19 illustrates an electrophoresis migration patter after RT-PCR of the plant in Example 19.
Figure 19:
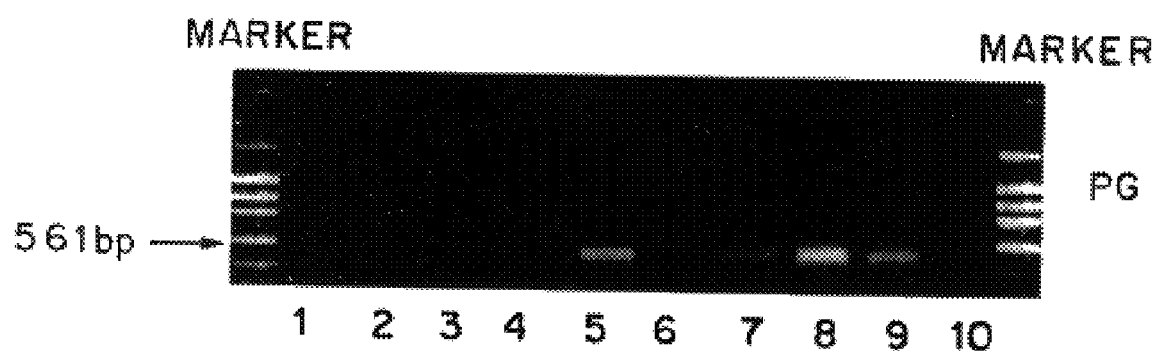

The reverse transcription reaction was carried out by using a random primer (9 mer) attached in the kit at 30° C. (1 minute), 55° C. (15 minutes), 99° C. (5 minutes) and 5° C. (5 minutes). Then, with the whole reaction solution used as the template, the PCR reaction was carried out using combinations of:
  1) primer TOM-1 (SEQ ID NO 61) and primer TOM-2 (SEQ ID NO 62), synthesized on the basis of the tomato EXT cDNA fragment [EP-0562836 A1 (1993)], and
  2) primer PG-SP3 (SEQ ID NO 63) and primer PG-AP2 (SEQ ID NO 64), synthesized on the basis of Tomato PG cDNA fragment [Molecular & General Genetics, 208, 30–36 (1987)]. The reaction was carried out by repeating 25 times a cycle at 94° C. (0.5 minute), 55° C. (1 minute), and 72° C. (1 minute). After the reaction, an aliquot of the reaction solution was subjected to 1% agarose gel electrophoresis. The results are shown in FIG. 19. That is to say, FIG. 19 illustrates the RT-PCR using the tomato tissues, wherein the expression of the tomato EXT, amplified by the primers described in 1) mentioned above, in each of the ripening stages was shown in the upper row and the expression of Tomato PG (the amplification product), amplified by the primers described in 2) mentioned above, in each of the ripening stages was shown in the lower row. Also in the figure, each lane with increasing the number indicates the increasing ripening stages for the fruit. In other words, lanes 1 and 2 correspond to the immature green fruit (of which the surface is green but a gelly substance is not formed in the inside), lanes 3 and 4 to the mature green fruit (of which the surface is green and a gelly substance is formed in the inside), lanes 5 and 6 to a turning fruit (10 to 30% of the fruit surface turns red), lanes 7 and 8 to a pink fruit (30 to 60% of the fruit surface turns red), and lanes 9 and 10 to the mature red fruit (100% of the fruit surface turns red).

As can be seen from FIG. 19, it was revealed on comparison of the expression of the tomato EXT at each ripening stages that an intense expression of the tomato EXT was induced at the immature green to mature green stages, as the amplification product (about 913 bp) was detected in lane 1 to lane 4 corresponding to these stages. On the other hand, it was revealed that the Tomato PG mRNA used as a control was expressed intensely in the turning and pink stages corresponding to lanes 5 to 9 where the amplification product (about 561 bp) was detected.

These results revealed that the tomato EXT promoter was a promoter that induces an intense gene expression particularly in growing stems and enlarging fruits (immature to mature green). That is to say, it was revealed that the gene expression was induced in each case at the site required for the reconstitution of plant cell wall xyloglucan and at the stage required for the reconstitution of plant cell wall xyloglucan.

EXAMPLE 20

Transient Assay Using Tobacco Culture Cells (1) Construction of Plasmids for Transfer First, construction of respective plasmids for the transfer was performed in order to transfer a plasmid containing a chimeric gene of a promoter region and the GUS gene into the protoplasts of tobacco BY2 culture cells by using the electroporation method.

1. Preparation of Plasmid Containing Chimeric Gene of DNA Fragment Containing Azuki Bean EXT2 Gene Promoter Region and the GUS Gene (Transcriptional Fusion)

Figure 20:
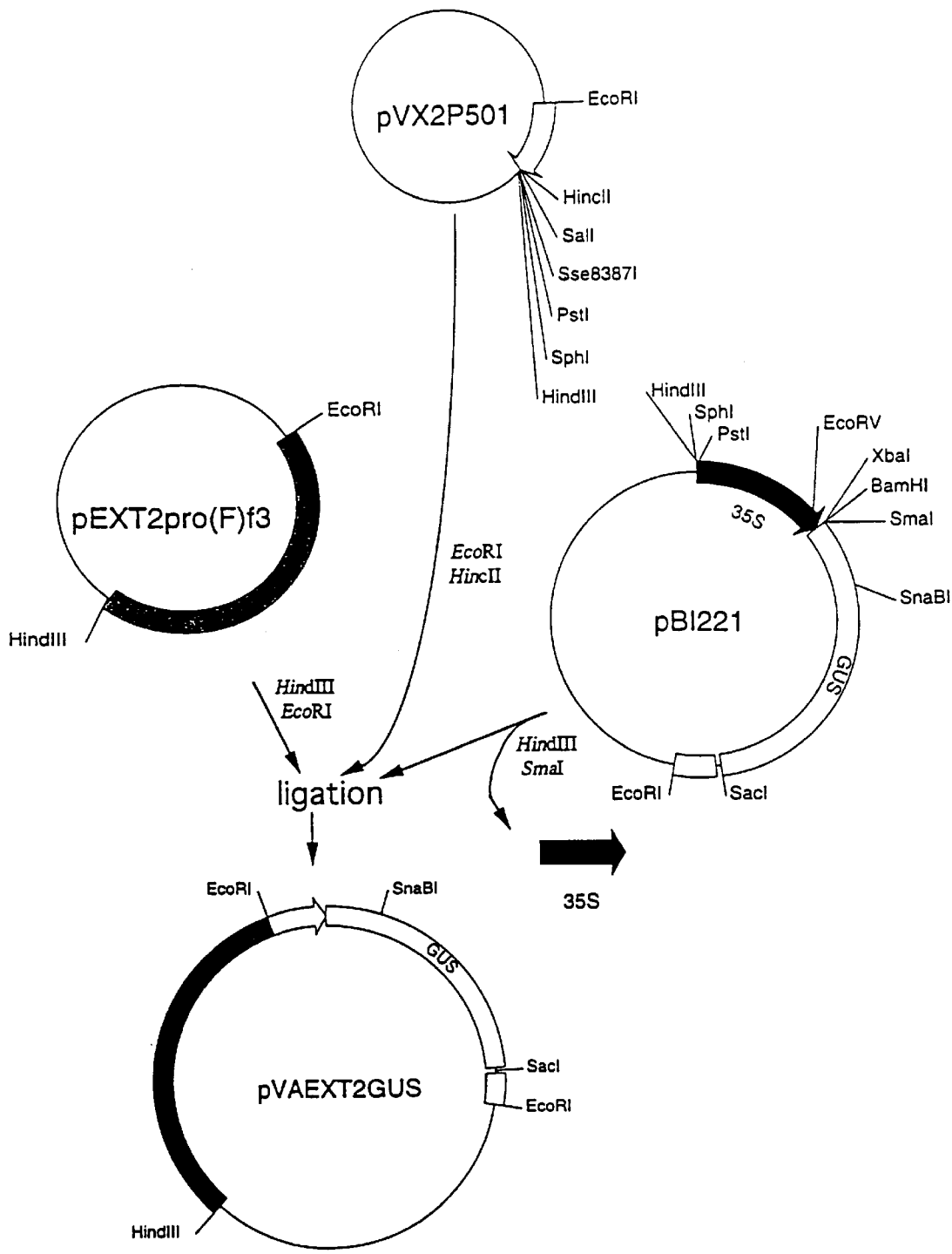
FIG. 20 is a construction diagram of pVAEXT2GUS.

A plasmid containing a chimeric gene of a DNA fragment containing the azuki bean EXT2 gene promoter region and the GUS gene was constructed as illustrated in FIG. 20. That is to say, pBI221 (Clontech) having the cauliflower mosaic virus 35S promoter, the *E. coli*-origin GUS gene, and a transcription termination sequence cassette originating from nopaline synthetase was utilized.

First, in order to remove the cauliflower mosaic virus 35S promoter region in pBI221, this plasmid was subjected to digestion with restriction enzymes Hind III and Sma I (TAKARA SHUZO Co., Ltd.), and then purification of the objective fragment other than the 35S promoter region by agarose gel electrophoresis followed by cutting-off. Next, pVX2P501 prepared in Example 13 was subjected to complete digestion with restriction enzymes EcoR I and Hinc II, and then purification of the about 0.5 kbp inserted fragment by agarose gel electrophoresis followed by cutting-off. Also, pEXT2pro(F) f3 prepared in Example 13 was subjected to complete digestion with restriction enzymes Hind III and EcoR I, and then purification of the about 2.55 kbp inserted fragment by agarose gel electrophoresis followed by cutting-off. These DNA fragments were ligated together and then transformed into *E. coli* JM 109 strain. This plasmid was named as pVAEXT2GUS and *E. coli* JM 109 strain transformed with pVAEXT2GUS was named as *Escherichia coli* JM 109/pVAEXT2GUS. This pVAEXT2GUS formed an about 3.4 kbp band by digestion with restriction enzymes Hind III and SnaB I, followed by agarose gel electrophoresis, thereby revealing that this plasmid contained the full length of the about 3.0 kbp azuki bean EXT2 gene promoter region.

2. Preparation of Plasmid Containing Chimeric Gene of DNA Fragment Containing Azuki Bean EXT3 Gene Promoter Region and the GUS Gene (Transcriptional Fusion)

Figure 21:
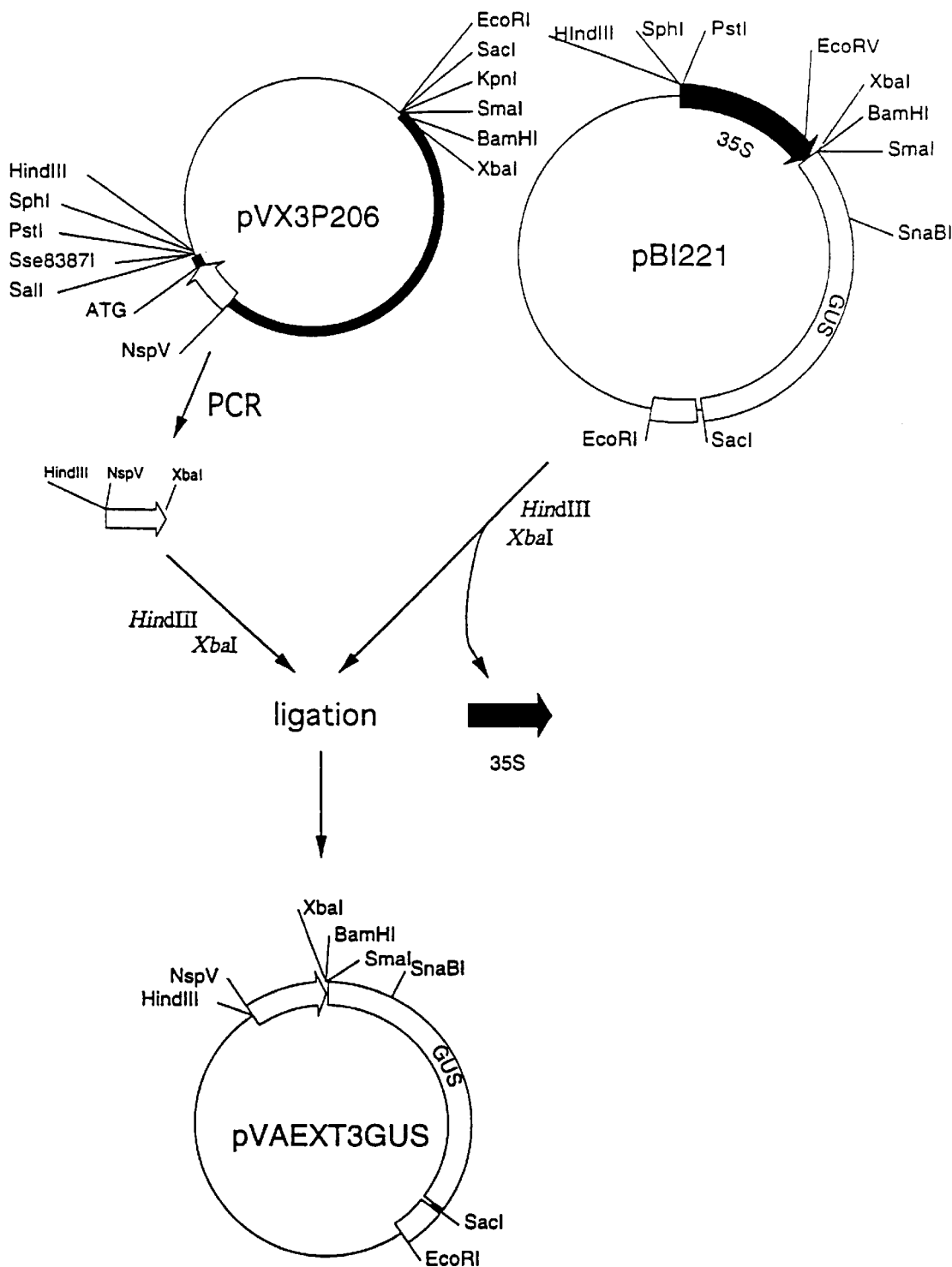
FIG. 21 is a construction diagram of pVAEXT3GUS.

A vector containing a chimeric gene of a DNA fragment containing the azuki bean EXT3 gene promoter region and the GUS gene was constructed as illustrated in FIG. 21. That is to say, pBI221 (Clontech) having the cauliflower mosaic virus 35S promoter, the *E. coli*-origin GUS gene, and a transcription termination sequence cassette originating from nopaline synthetase was utilized.

First, in order to remove the cauliflower mosaic virus 35S promoter region in pBI221, this plasmid was subjected to digestion with restriction enzymes Hind III and Xba I, and then purification of the objective fragment other than the 35S promoter region by agarose gel electrophoresis followed by cutting-off. Next, with about 0.3 μg of pVX3P206 prepared in Example 14 used as the template, PCR was carried out by using primer VX3UH (SEQ ID NO 65), which situated in a region downstream from Nsp V in the azuki bean EXT3 gene promoter region in pVX3P206, and primer VX3LX (SEQ ID NO 66), the sequence just before the translation initiation point. These primer VX3UH (SEQ ID NO 65) and primer VX3LX (SEQ ID NO 66) were synthesized so that the Xba I site and Hind III site were transferred into the both termini of the PCR product, respectively. The reaction was carried out by repeating a cycle of 94° C. (1 minute), 55° C. (1 minute), and 72° C. (2 minutes) 10 times. After the reaction, 5 μl of the reaction solution underwent 1% agarose gel electrophoresis to detect an about 0.4 kbp band in addition to the template plasmid band. Since the Xba I site and Hind III site had been transferred into primer VX3UH (SEQ ID NO 65) and primer VX3LX (SEQ ID NO 66), respectively, this about 0.4 kbp DNA fragment was subjected to purification by agarose gel electrophoresis, digestion with restriction enzymes Hind III and Xba I, ligation with the previously-purified pBI221 Hind III-Xba I DNA fragment, and then transformation into *E. coli* JM 109 strain. This plasmid was named as pVAEXT3GUS and *E. coli* JM 109 strain transformed with pVAEXT3GUS was named as *Escherichia. coli* JM 109/pVAEXT3GUS.

This pVAEXT3GUS formed an about 0.4 kbp band by digestion with restriction enzymes Hind III and Xba I, followed by agarose gel electrophoresis, thereby revealing that this plasmid contained the full length of the about 0.4 kbp azuki bean EXT3 gene promoter region.

3. Preparation of Plasmid Containing Chimeric Gene of DNA Fragment Containing Azuki Bean XRP1 Gene Promoter Region and the GUS Gene (Translational Fusion)

Figure 22:
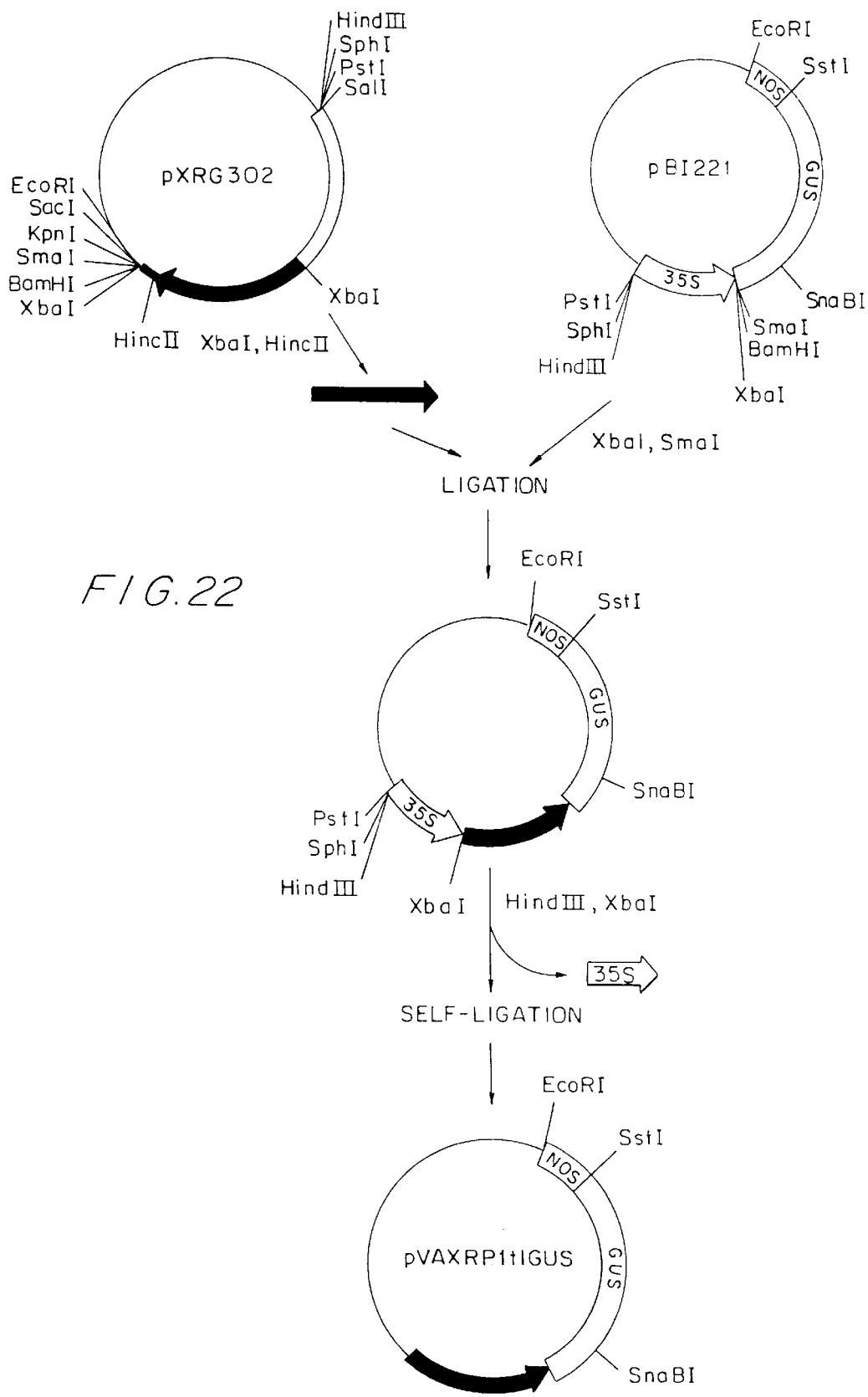
FIG. 22 is a construction diagram of pVAXRP1tlGUS.

A vector containing a translational fusion chimeric gene of a DNA fragment containing the azuki bean XRP1 gene promoter region and the GUS gene was constructed as illustrated in FIG. 22. That is to say, pBI221 (Clontech) having the cauliflower mosaic virus 35S promoter, the E. coli-origin GUS gene, and a transcription termination sequence cassette originating from nopaline synthetase was utilized.

First, pBI221 was subjected to digestion with restriction enzymes Xba I and Sma I, and then purification of the objective DNA fragment by agarose gel electrophoresis followed by cutting-off. Next, pXRG302 prepared in Example 15 was subjected to double digestion with restriction enzymes Xba I-Hinc II and then purification of the about 1.1 kbp inserted fragment by agarose gel electrophoresis followed by cutting-off. This DNA fragment was ligated to the previously-purified pBI221 DNA fragment and then transformed into E. coli JM 109 strain.

A plasmid was prepared from the colonies obtained. Next, in order to remove the cauliflower mosaic virus 35S promoter region in this plasmid, the plasmid was subjected to digestion with restriction enzymes Hind III and Xba I, self-ligation, and then transformation into E. coli JM 109 strain. A plasmid was purified from the colonies obtained. This plasmid was named as pVAXRP1tlGUS and E. coli JM 109 strain transformed with pVAXRP1tlGUS was named as Escherichia. coli JM 109/pVAXRP1tlGUS. PCR, which was carried out with this pVAXRP1tlGUS used as a template and by using M13 Primer M4 (TAKARA SHUZO Co., Ltd.) and M13 Primer RV (TAKARA SHUZO Co., Ltd.), followed by agarose gel electrophoresis, resulted in formation of an about 3.0 kbp band, thereby revealing that this plasmid contained the full length of the about 1.1 kbp azuki bean XRP1 gene promoter region.

Furthermore, when the nucleotide sequence of a portion upstream from the GUS-gene in pVAXRP1tlGUS up to the promoter region determined, it was confirmed that the gene originating from pBI221 (SEQ ID NO 68) was integrated after a gene encoding the azuki bean XRP1 N-terminal amino acid sequence in such a manner that GUS could be expressed so as to form the translational-fusion protein of GUS having the azuki bean XRP1 N-terminal amino acid sequence by this pVAXRP1tlGUS.

4. Preparation of Plasmid Containing Chimeric Gene of DNA Fragment Containing Tomato EXT Gene Promoter Region and the GUS Gene (Transcriptional Fusion)

Figure 23:
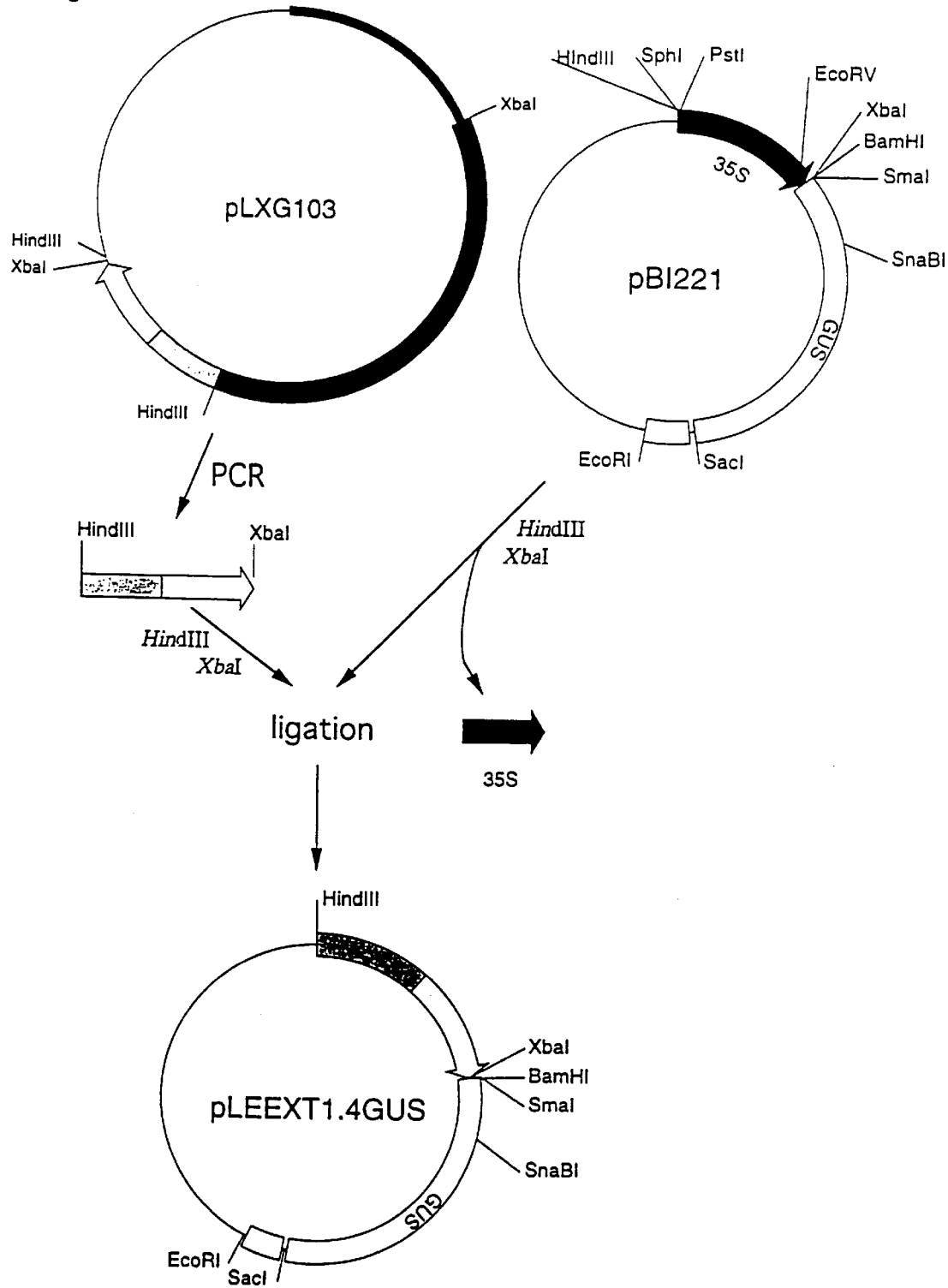
FIG. 23 is a construction diagram of pLEEXT1.4GUS.

A vector containing a chimeric gene of a DNA fragment containing the tomato EXT gene promoter region (about 1.4 kbp) and the GUS gene was constructed as illustrated in FIG. 23. That is to say, pBI221 (Clontech) having the cauliflower mosaic virus 35S promoter, the E. coli-origin GUS gene, and a transcription termination sequence cassette originating from nopaline synthetase was utilized.

First, in order to remove the cauliflower mosaic virus 35S promoter region in pBI221, this plasmid was subjected to double digestion with restriction enzymes Hind III-Xba I and then purification of the objective fragment other than the 35S promoter region by agarose gel electrophoresis followed by cutting-off. Next, with about 0.3 μg of pLXG103 used as the template, PCR was carried out by using primer LXUH1 (SEQ ID NO 69), which situated in a region downstream from Hind III site in the tomato EXT gene promoter region in pLXG103 prepared in Example 16, and primer LXLX (SEQ ID NO 70), the sequence just before the translation startpoint. These primer LXUH1 (SEQ ID NO 69) and primer LXLX (SEQ ID NO 70) were synthesized so that the Hind III site and Xba I site were added and transferred into the termini of the PCR product, respectively. The reaction was carried out by repeating a cycle of 94° C. (1 minute), 55° C. (1 minute), and 72° C. (2 minutes) 10 times. After the reaction, 5 μl of the reaction solution underwent 1% agarose gel electrophoresis to detect an about 1.4 kbp band in addition to the template plasmid band. Since the Hind III site and Xba I site had been transferred into primer LXUH1 (SEQ ID NO 69) and primer LXLX (SEQ ID NO 70), respectively, this about 1.4 kbp DNA fragment was subjected to purification by agarose gel electrophoresis, digestion with restriction enzymes Hind III and Xba I, ligation with the previously-purified pBI221 DNA fragment, and then transformation into E. coliJM 109 strain. This plasmid was named as pLEEXT1.4GUS and E. coli JM 109 strain transformed with pLEEXT1.4GUS was named as Escherichia. coli JM 109/pLEEXT1.4GUS.

This pLEEXT1.4GUS formed an about 1.4 kbp band by digestion with restriction enzymes Hind III and Xba I, followed by agarose gel electrophoresis, thereby revealing that this plasmid contained the about 1.4 kbp tomato EXT3 gene promoter region.

Figure 24:
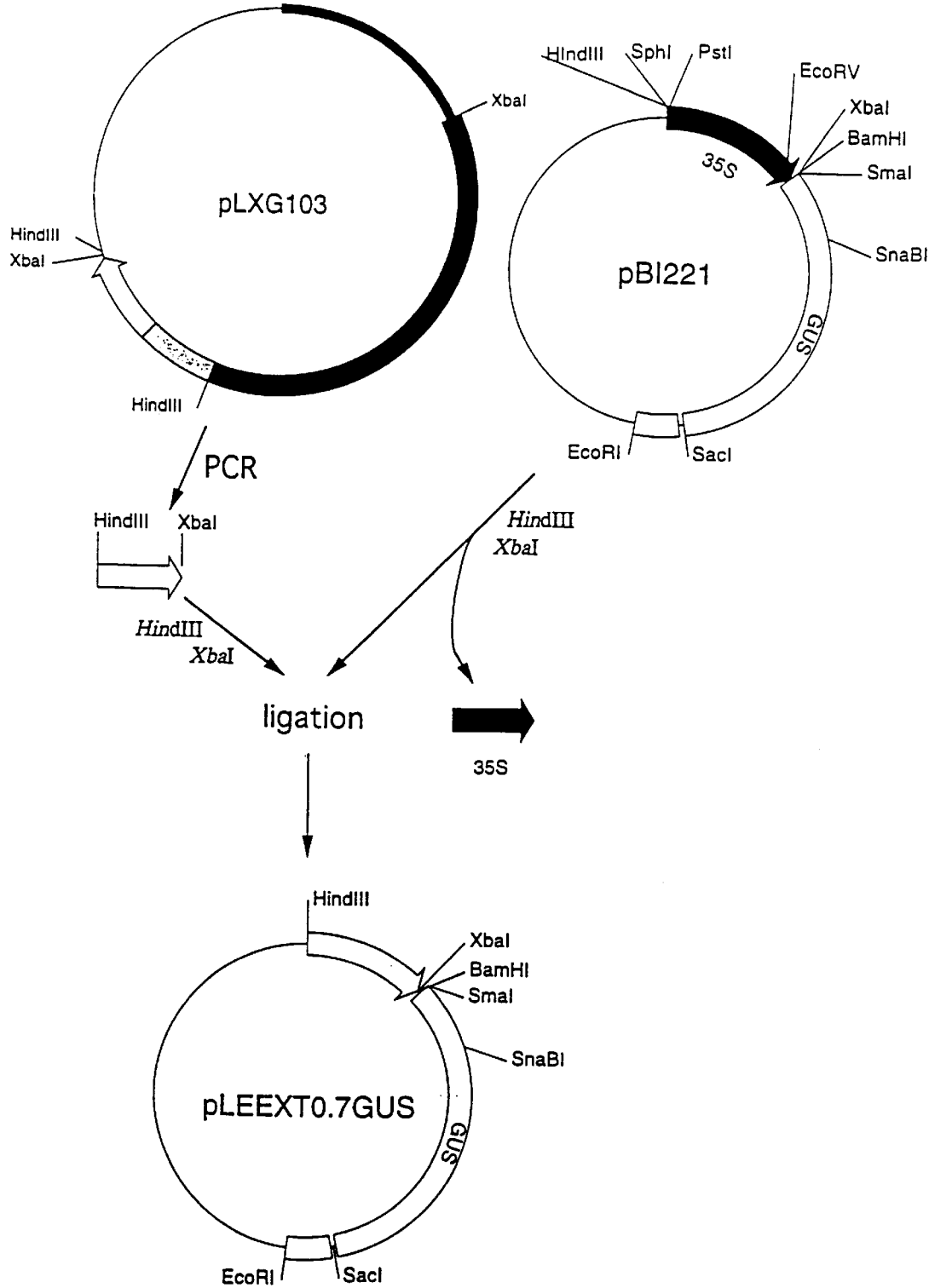
FIG. 24 is a construction diagram of pLEEXT0.7GUS.

Moreover, as shown in FIG. 24, a plasmid having a fusion gene (transcriptional fusion) with the GUS gene using only a region homologous with the tobacco EXT gene promoter region was prepared.

With about 0.3 μg of pLXG103 prepared in Example 16 used as the template, PCR was carried out by using primer LXUH2 (SEQ ID NO 71), which situated in the 5'-downstream from a region homologous with the tobacco EXT gene promoter region and the tomato EXT gene promoter region in pLXG103, and primer LXLX (SEQ ID NO 70), the sequence just before the translation startpoint. These primer LXUH2 (SEQ ID NO 71) and primer LXLX (SEQ ID NO 70) were synthesized so that the Hind III site and Xba I site were added and transferred into the both termini of the PCR product, respectively. The reaction was carried out by repeating a cycle of 94° C. (1 minute), 55° C. (1 minute), and 72° C. (2 minutes) 10 times. After the reaction, 5 μl of the reaction solution underwent 1% agarose gel electrophoresis to detect an about 0.7 kbp band in addition to the template plasmid band. Since the Hind III site and Xba I site had been transferred into primer LXUH2 (SEQ ID NO 71) and primer LXLX (SEQ ID NO 70), respectively, this about 0.7 kbp DNA fragment was subjected to purification by agarose gel electrophoresis, digestion with restriction enzymes Hind III and Xba I, ligation with the previously-purified pBI221 DNA fragment, and then transformation into E. coli JM 109 strain. This plasmid was named as pLEEXT0.7GUS and E. coli JM 109 strain transformed with pLEEXT0.7GUS was named as Escherichia. coli JM 109/pLEEXT0.7GUS.

This pLEEXT0.7GUS formed an about 0.7 kbp band by digestion with restriction enzymes Hind III and Xba I, followed by agarose gel electrophoresis, thereby revealing that this plasmid contained the about 0.7 kbp tomato EXT gene promoter region.

5. Preparation of Plasmid Containing Chimeric Gene of DNA Fragment Containing Tomato XRP Gene Promoter Region and the GUS Gene (Translational Fusion)

Figure 25:
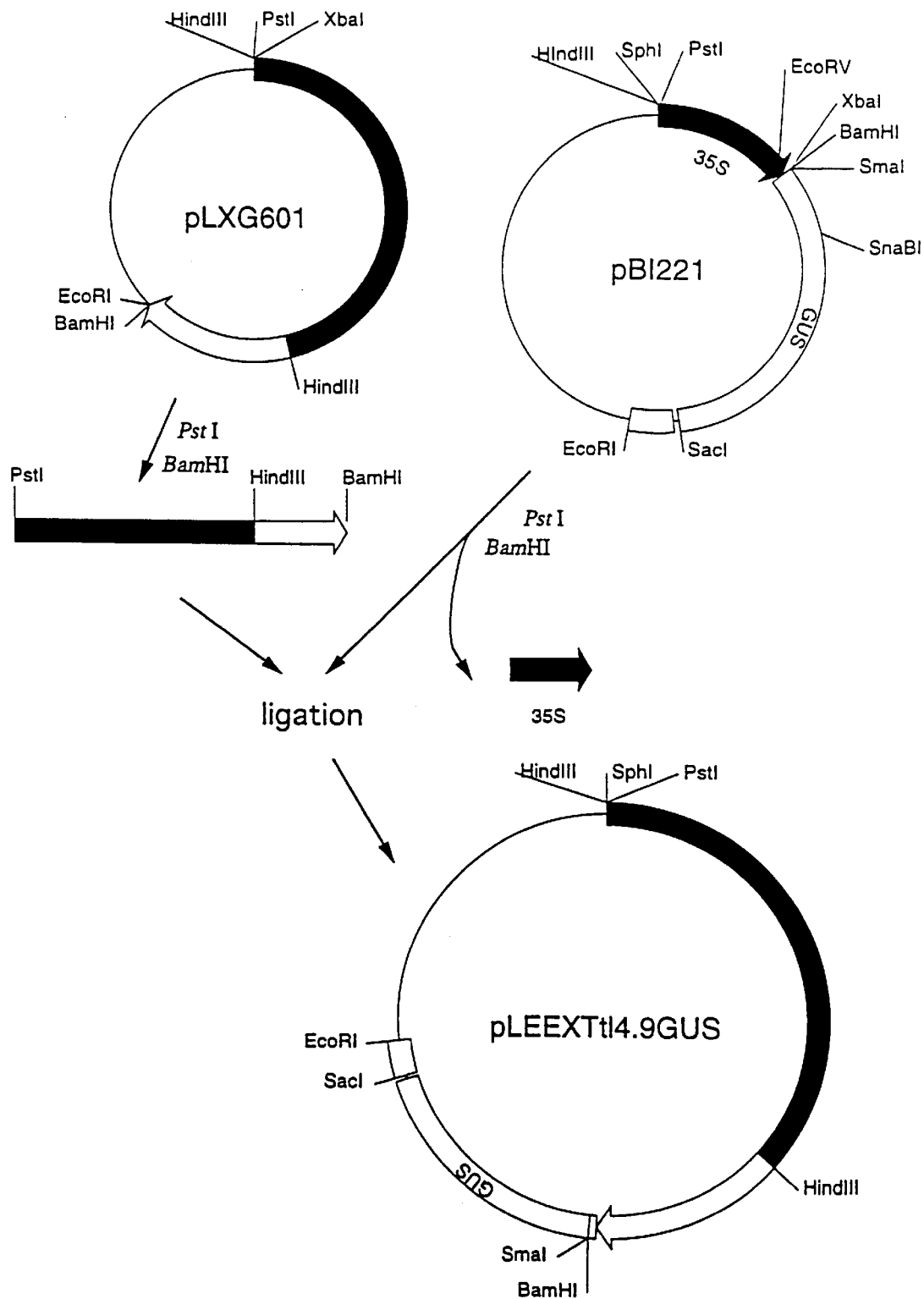
FIG. 25 is a construction diagram of pLEEXTtl4.9GUS.

A vector containing a gene (SEQ ID NO 72) encoding the tomato EXT N-terminal amino acid sequence and a translational-fusion of an about 4.9 kbp DNA fragment with the GUS gene was constructed as illustrated in FIG. 25. That is to say, pBI221 (Clontech) having the cauliflower mosaic virus 35S promoter, the E. coli-origin GUS gene, and a transcription termination sequence cassette originating from nopaline synthetase was utilized.

First, in order to remove the cauliflower mosaic virus 35S promoter region in pBI221, this plasmid was subjected to digestion with restriction enzymes Pst I and BamH I, and then purification of the objective DNA fragment other than the 35S promoter region by agarose gel electrophoresis followed by cutting-off. Next, pLXG601 prepared in Example 16 was subjected to digestion with restriction enzymes Pst I and BamH I, and then purification of the about 4.9 kbp inserted fragment by agarose gel electrophoresis followed by cutting-off. This DNA fragment was ligated to the previously-purified pBI221 DNA fragment and then transformed into *E. coli* JM 109 strain. This plasmid was named as pLEEXTtl4.9GUS and *E. coli* JM 109 strain transformed with pLEEXTtl4.9GUS was named as *Escherichia. coli* JM 109/pLEEXTtl4.9GUS. Complete digestion of this pLEEXTtl4.9GUS with restriction enzymes Pst I and BamH I, followed by agarose gel electrophoresis, resulted in formation of an about 4.9 kbp band, thereby revealing that this plasmid contained the about 4.9 kbp tomato EXT gene promoter region.

Furthermore, when the nucleotide sequence of a portion upstream from the GUS gene up to the promoter region in pLEEXTtl4.9GUS, it was confirmed that a gene originating from pBI221 (SEQ ID NO 73) was integrated after a gene encoding the tomato EXT N-terminal amino acid sequence in such a manner that GUS could be expressed so as to form the translational-fusion protein of GUS having the tomato EXT N-terminal amino acid sequence by this pLEEXTtl4.9GUS.

Figure 26:
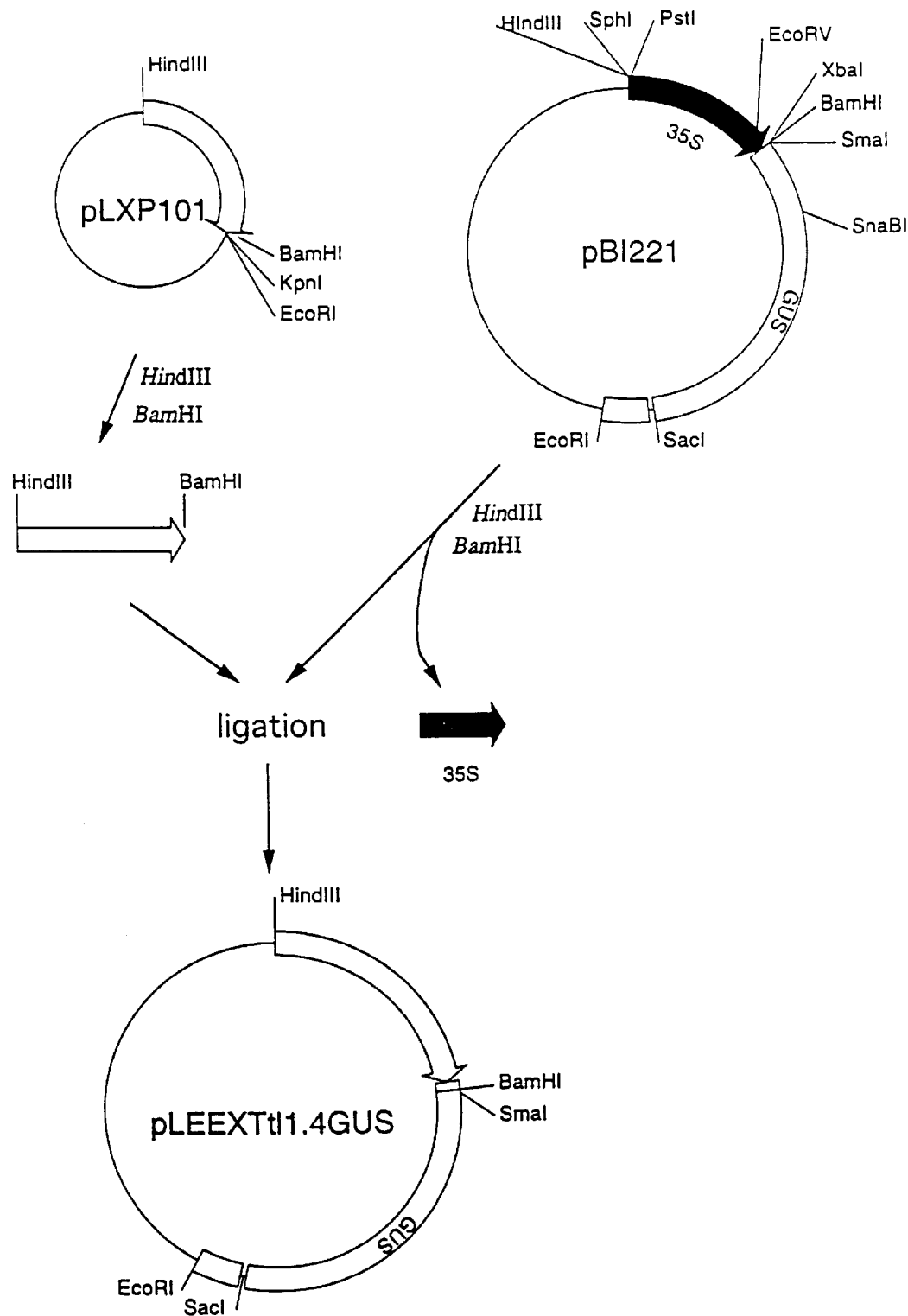
FIG. 26 is a construction diagram of pLEEXTtl1.4GUS.

Next, a vector containing a translational fusion of an about 1.4 kbp DNA fragment containing a gene (SEQ ID NO 72) encoding the tomato EXT N-terminal amino acid sequence and a promoter region with the GUS gene was constructed as illustrated in FIG. 26. That is to say, pBI221 (Clontech) having the cauliflower mosaic virus 35S promoter, the *E. coli*-origin GUS gene, and a transcription-termination sequence cassette originating from nopaline synthetase was utilized.

First, in order to remove the cauliflower mosaic virus 35S promoter region in pBI221, this plasmid was subjected to digestion with restriction enzymes Hind III and BamH I, and then purification of the objective DNA fragment other than the 35S promoter region by agarose gel electrophoresis followed by cutting-off. Next, pLXP101 prepared in Example 16 was subjected to digestion with restriction enzymes Hind III and BamH I, and then purification of the about 1.4 kbp inserted fragment by agarose gel electrophoresis followed by cutting-off. This DNA fragment was ligated to the previously-purified pBI221 DNA fragment and then transformed into *E. coli* JM 109 strain. This plasmid was named as pLEEXTtl1.4GUS and *E. coli* JM 109 strain transformed with pLEEXTtl1.4GUS was named as *Escherichia. coli* JM 109/pLEEXTtl1.4GUS.

Complete digestion of this pLEEXTtl1.4GUS with restriction enzymes Hind III and BamH I, followed by agarose gel electrophoresis, resulted in formation of an about 1.4 kbp band, thereby revealing that this plasmid contained the about 1.4 kbp tomato EXT gene promoter region.

Furthermore, when the nucleotide sequence of a portion upstream from the GUS gene up to the promoter region in pLEEXTtl1.4GUS was determined, it was confirmed that a gene originating from pBI221 (Sequence No. 73) was integrated after a gene encoding the tomato EXT N-terminal amino acid sequence is such a manner that GUS could be expressed so as to form the translational fusion protein of GUS having the tomato EXT N-terminal amino acid sequence by this pLEEXTtl1.4GUS.

6. Preparation of Plasmid Containing Chimeric Gene of DNA Fragment Containing Tobacco EXT Gene Promoter Region and the GUS Gene (Transcriptional Fusion)

Figure 27:
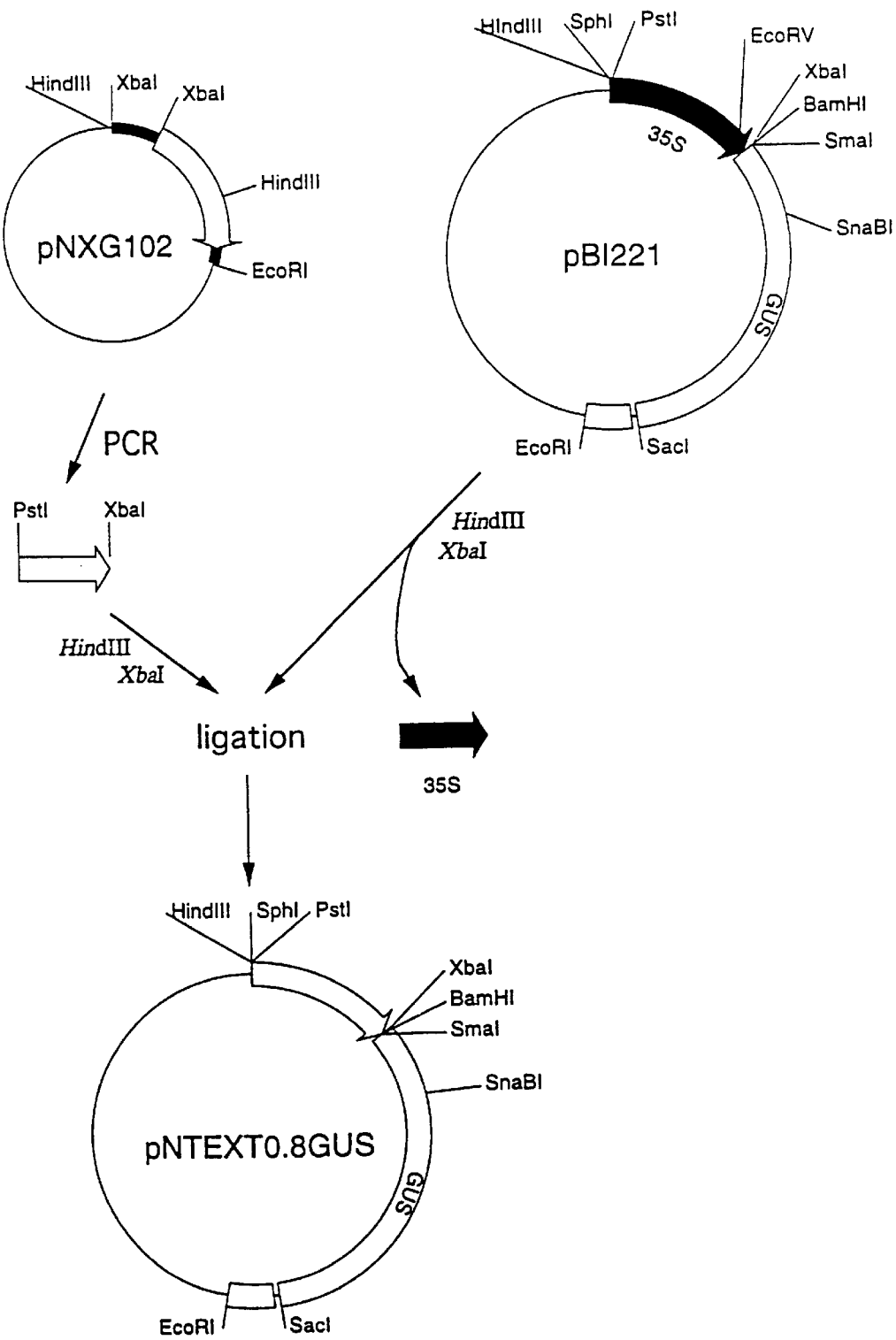
FIG. 27 is a construction diagram of pNTEXT0.8GUS.

A vector containing a chimeric gene of a DNA fragment containing the tobacco EXT gene promoter region and the GUS gene was constructed as illustrated in FIG. 27. That is to say, pBI221 (Clontech) having the cauliflower mosaic virus 35S promoter, the *E. coli*-origin GUS gene, and a transcription termination sequence cassette originating from nopaline synthetase was utilized.

First, in order to remove the cauliflower mosaic virus 35S promoter region in pBI221, this plasmid was subjected to digestion with restriction enzymes Pst I and Xba I, and then purification of the objective fragment other than the 35S promoter region by agarose gel electrophoresis followed by cutting-off. Next, with about 0.3 μg of pNXG102 prepared in Example 17 used as the template, PCR was carried out by using primer NXUP (SEQ ID NO 74), which situated in a region downstream from Hind III site in the tobacco EXT gene promoter region in pNXG102, and primer NXLX (SEQ ID NO 75), the sequence just before the translation initiation point. These primer NXUP (SEQ ID NO 74) and primer NXLX (SEQ ID NO 75) were synthesized so that the Pst I site and Xba I site were added and transferred into the both termini of the PCR product, respectively. The reaction was carried out by repeating a cycle of 94° C. (1 minute), 55° C. (1 minute), and 72° C. (2 minutes) 10 times. After the reaction, 5 μl of the reaction solution underwent 1% agarose gel electrophoresis to detect an about 0.8 kbp band in addition to the template plasmid band. Since the Pst I site and Xba I site had been transferred into primer NXUP (SEQ ID NO 74) and primer NXLX (SEQ ID NO 75), respectively, this about 0.8 kbp DNA fragment was subjected to purification by agarose gel electrophoresis, digestion with restriction enzymes Pst I and Xba I, ligation with the previously-purified pBI221 DNA fragment, and then transformation into *E. coli* JM 109 strain. This plasmid was named as pLEEXT0.8GUS and *E. coli* JM 109 strain transformed with pLEEXT0.8GUS was named as *Escherichia. coli* JM 109/pLEEXT0.8GUS.

This pLEEXT0.8GUS formed an about 0.8 kbp band by digestion with restriction enzymes Pst I and Xba I, followed by agarose gel electrophoresis, thereby revealing that this plasmid contained the about 0.8 kbp tobacco EXT gene promoter region.

7. Preparation of Plasmid Containing Chimeric Gene of DNA Fragment Containing Wheat EXT Gene Promoter Region and the GUS Gene (Transcriptional Fusion)

Figure 28:
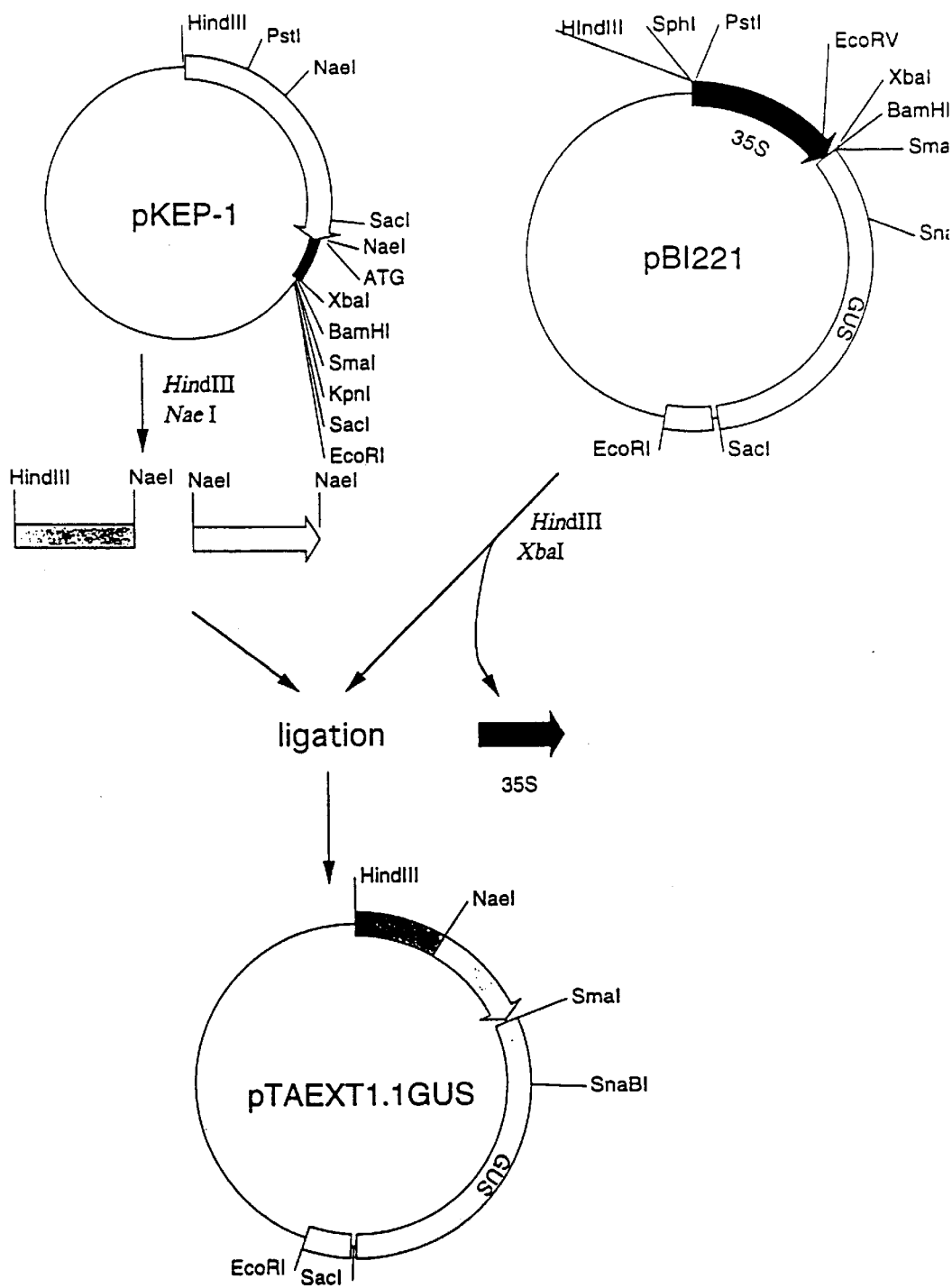
FIG. 28 is a construction diagram of pTAEXT1.1GUS.

A vector containing a chimeric gene of a DNA fragment containing the wheat EXT gene promoter region and the GUS gene was constructed as illustrated in FIG. 28. That is to say, pBI221 (Clontech) having the cauliflower mosaic virus 35S promoter, the *E. coli*-origin GUS gene, and a transcription termination sequence cassette originating from nopaline synthetase was utilized.

First, in order to remove the cauliflower mosaic virus 35S promoter region in pBI221, this plasmid was subjected to digestion with restriction enzymes Hind III and Sma I, and then purification of the objective DNA fragment other than the 35S promoter region by agarose gel electrophoresis followed by cutting-off. Next, about 2 μg of pKEP-1 prepared in Example 18 was subjected to complete digestion with restriction enzymes Hind III and Nae I, and then purification of the about 0.6 kbp and about 0.5-kbp DNA fragments by agarose gel electrophoresis followed by cutting-off.

Both of the DNA about 0.6-kbp and about 0.5-kbp fragments were ligated to the previously-purified pBI221 DNA fragment and then transformed into *E. coli* JM 109 strain. This plasmid was named as pTAEXT1.1GUS and *E. coli* JM 109 strain transformed with said plasmid was named as *Escherichia. coli* JM 109/pTAEXT1.1GUS.

Digestion of this pTAEXT1.1GUS with restriction enzymes Hind III and EcoR I, followed by agarose gel electrophoresis, resulted in formation of an about 3.3 kbp band, thereby revealing that this plasmid contained the about 1.1 kbp wheat EXT gene promoter region.

(2) Gene Transfer by Electroporation

In order to transfer each of plasmids, prepared in Example 20-1 to 20-7 as described above, into tobacco BY2 culture cells by the electroporation method, the tobacco BY2 culture cells were treated with an enzyme solution (pH: 5.5) containing 1% cellulase-ONOZUKA (Yakult Honsha Co., Ltd.), 0.1% pectolyase Y23 (SEISHIN Corporation), and 0.4 M mannitol at 30° C. for 2 hours to be converted into cell wall-free protoplasts. A suspension of the $2 \times 10^6$ protoplasts of the tobacco BY2 culture cells in an electroporation buffer solution (70 mM KCl, 5 mM YES, and 0.3 M mannitol, pH 5.8) was mixed with 3 pmol of each of plasmids, prepared in paragraphs 1 to 7 as described above, and a 10% PEG6000/electroporation buffer solution with stirring. An electric pulse (300 V, 125 $\mu$F) using Gene Pulser II (Bio-Rad Laboratories) was applied to the resulting mixture to transfer the DNA into the plant cells.

The cells were incubated in the Linsmaier-Skoog culture medium [Physiologia Plantarum, 18, 100 (1965)] containing 0.2 mg/l 2,4-D as an auxin, 1% sucrose, and 0.4 M. mannitol at 26° C. for 40 hours after the transfer. The cells were recovered and a mixture of the recovered cells in 200 $\mu$l of an extraction buffer solution [50 mM phosphate buffer (pH 7.0), 10 mM EDTA, 0.1% Triton X-100, 0.1% Sarkosyl, and 10 mM 2-mercaptoethanol] placed in an Eppendorf tube was subjected to ultra-sonication on ice for 30 seconds by using a ultrasonicator W-225 (Heatsystems-Ultrasonics) with setting the output control at 1.5 and the duty cycle at 50%. Then, a supernatant isolated by centrifugation was used for the assay of the GUS activity and the assay of the amount of protein.

(3) Measurement of Promoter Activity The reaction was carried out by adding 45 $\mu$l of the extraction buffer solution and 25 $\mu$l of a 4 mM 4-MUG substrate to each 30 $\mu$l of the above-mentioned extracts placed in a 96-well microtiter plate for fluorescence. After 5, 35, and 95 minutes, the reaction was terminated by addition of 50 $\mu$l of a reaction-termination solution (1 M $Na_2CO_3$). Then, the specific fluorescence emitted by 4-MU, the reaction product, at an excitation wavelength of 365 nm and fluorescence wavelength of 455 nm, was measured with a fluorescence plate reader [Fluoroscan II (Labosystems)].

Moreover, the protein quantity was assayed by a procedure exemplified as follows. Thus, 2, 5, 10, 15, 20, and 30 $\mu$l of a ⅕-diluted solution of the extract or an 800 $\mu$g/ml BSA standard solution (20 $\mu$l of the extract buffer solution is mixed with 80 $\mu$l of 1 mg/ml BSA) were placed in a 96-well microtiter plate and thereto were added respectively 158, 155, 150, 145, 140, and 130 $\mu$l of distilled water and 40 $\mu$l of the assay reagent in Bio-Rad Protein Assay Kit (Bio-Rad Laboratories). After being stirred slowly and then allowed to stand for 20 minutes at room temperature, the mixture was measured by a plate reader (wavelength: 590 nm) within 60 minutes to assay the protein quantity.

Figure 29:
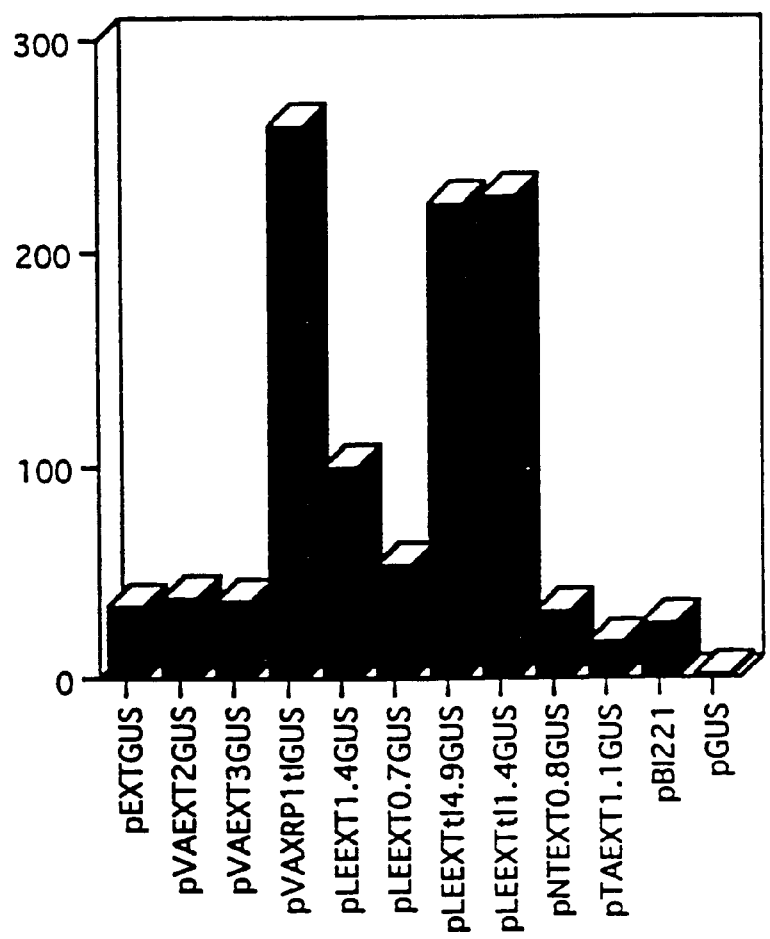
FIG. 29 is a graph illustrating the comparison of the GUS specific activities of the transformed tobacco culture cells in Example 11 and Example 20.

The GUS activity was measured in the following way. At the same time when the above assays were carried. out, the fluorescence intensities of the 4-MU standard solutions were measured and the results were plotted on a graph with the 4-MU quantity (pmol) at the x-axis and the fluorescence intensity at the y-axis. Then, the 4-MU quantity per one fluorescence unit was obtained from the slope and, further, the results on the samples were plotted on a graph with the time (minute) at the horizontal axis and the fluorescence intensity at the vertical axis to obtain the increasing rate of the fluorescence intensity and then to obtain the decomposition rate of 4-MUG equal to the GUS activity. In addition, the GUS specific activity was obtained from the amount of protein. The results are shown in FIG. 29. In other words, FIG. 29 illustrates comparison of the GUS-specific activity of the transformed tobacco BY2 culture cells, wherein the specific activity value upon the transfer of pLEEXT1.4GUS is taken as 100 for obtaining the GUS-specific activity upon the transfer of each plasmid and plotting each promoter activity on a graph, thereby enabling comparison the transfer experiments carried out 7 times in total.

In the figure, the GUS-specific activity values upon the transfer of each plasmid are indicated at the horizontal axis, with the specific activity value upon the transfer of pLEEXT1.4GUS being taken as 100, and the plasmids used in the experiments are indicated at the vertical axis. The n numbers are 2 to 7.

From these results, it was confirmed that the DNA fragment containing these EXT gene promoter regions exhibited an activity more intense than that of the cauliflower mosaic virus 35S promoter that had been said to be expressed intensely in the plants. As can be seen from this figure, it could be revealed that, particularly, the activities of the azuki bean XRP1 and tomato EXT promoters were extremely high and that the efficiency was better by the translational fusion from comparison of the tomato EXT promoters.

As described hereinabove, the present invention provides prompters of genes and family genes thereof encoding the endo-xyloglucan transferase (EXT) to be expressed in a specific manner at the site and stage required for the reconstitution of plant cell wall xyloglucan. Moreover, the present invention provides methods for cloning the promoters of the EXT genes and family genes thereof, plant transformation vectors containing the promoters of the EXT genes and family genes thereof as well as methods for preparing them, methods for regulating the expression of the promoters of the EXT genes and family genes thereof, and methods for controlling the plant morphology and plants using the promoters of the EXT genes and family genes thereof.

What is claimed is:

1. An isolated plant promoter, which in plants is natively located upstream of and controls the expression of a gene encoding a polypeptide having endo-xyloglucan transferase activity.

2. The isolated plant promoter of claim 1, wherein said gene encoding a polypeptide having endo-xyloglucan transferase activity originates in azuki bean (*Vigna angularis*).

3. The isolated plant promoter of claim 1, wherein said gene encoding a polypeptide having endo-xyloglucan transferase activity originates in tomato (*Lycopersicon esculentum*).

4. The isolated plant promoter of claim 1, wherein said gene encoding polypeptide having endo-xyloglucan transferase activity originates in tobacco (*Nicotiana tabacum*).

5. The isolated plant promoter of claim 1, wherein said gene encoding a polypeptide having endo-xyloglucan transferase activity originates in wheat (*Triticum asestivum*).

6. The isolated plant promoter of claim 1, wherein the promoter is contained in any one nucleotide sequence selected from SEQ ID NOs:1, 2, 3, 4, 5, 6, 7, and 8.

7. An isolated DNA molecule comprising the plant promoter of claim 1, which is ligated to a useful gene in a state capable of expressing the useful gene.

8. The isolated DNA molecule of claim 7, wherein the useful gene is a gene encoding a protein.

9. The isolated DNA molecule of claim 7, wherein the useful gene is a gene encoding antisense RNA.

10. The isolated DNA molecule of claim 7, wherein the useful gene is a gene encoding a decoy.

11. The isolated DNA molecule of claim 7, wherein the useful gene is a gene encoding a ribozyme.

12. A plant into which the isolated DNA molecule of claim 7 is transferred.

13. Plant cells into which the isolated DNA molecule of claim 7 is transferred.

14. A transgenic plant regenerated from plant cells into which the isolated DNA molecule of claim 7 is transferred.

15. A vector comprising the plant promoter of claim 1.

16. A vector comprising the DNA fragment of claim 7.

17. A vector of claim 15 which is a plasmid vector.

18. A vector of claim or 15 which is a viral vector.

19. A plant transformed with the vector of claim 15.

20. Plant cells transformed with the vector of claim 15.

21. A transgenic plant regenerated from the plant cells of claim 20.

22. A seed obtained from the plant of any one of claims 12, 14, 19 or 21.

23. A vector comprising the plant promoter of claim 2.

24. A vector comprising the plant promoter of claim 3.

25. A vector comprising the plant promoter of claim 4.

26. A vector comprising the plant promoter of claim 5.

27. A vector comprising the plant promoter of claim 6.

* * * * *